United States Patent
Haider et al.

(10) Patent No.: US 10,260,947 B2
(45) Date of Patent: Apr. 16, 2019

(54) SPECTROMETRIC SYSTEMS AND METHODS FOR IMPROVED FOCUS LOCALIZATION OF TIME- AND SPACE-VARYING MEASUREMENTS

(71) Applicant: Mayo Foundation for Medical Education and Research, Rochester, MN (US)

(72) Inventors: Clifton R. Haider, Rochester, MN (US); James A. Rose, Rochester, MN (US); Gary S. Delp, Rochester, MN (US); Barry K. Gilbert, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/056,214

(22) Filed: Aug. 6, 2018

(65) Prior Publication Data
US 2019/0033135 A1    Jan. 31, 2019

Related U.S. Application Data

(63) Continuation of application No. 15/643,193, filed on Jul. 6, 2017, now Pat. No. 10,072,983, which is a (Continued)

(51) Int. Cl.
*G01N 21/47* (2006.01)
*G01J 3/42* (2006.01)
(Continued)

(52) U.S. Cl.
CPC .............. *G01J 3/42* (2013.01); *A61B 5/0075* (2013.01); *A61B 5/14532* (2013.01);
(Continued)

(58) Field of Classification Search
CPC .. G01J 3/42; G01J 3/0237; A61B 5/00; A61B 5/0021; A61B 5/0026; A61B 5/0029;
(Continued)

(56) References Cited

U.S. PATENT DOCUMENTS 5,431,159 A   7/1995  Baker et al.
5,475,234 A   12/1995 Xu et al.
(Continued)

*Primary Examiner* — Jamil Ahmed
(74) *Attorney, Agent, or Firm* — Quarles & Brady LLP; Yakov Sidorin

(57) ABSTRACT

A system and method of dynamically localizing a measurement of parameter characterizing tissue sample with waves produced by spectrometric system at multiple wavelengths and detected at a fixed location of the detector of the system. The parameter is calculated based on impulse response of the sample, reference data representing characteristics of material components of the sample, and path lengths through the sample corresponding to different wavelengths. Dynamic localization is effectuated by considering different portions of a curve representing the determined parameter, and provides for the formation of a spatial map of distribution of the parameter across the sample. Additional measurement of impulse response at multiple detectors facilitates determination of change of the measured parameter across the sample as a function of time.

15 Claims, 58 Drawing Sheets

Related U.S. Application Data continuation of application No. 14/397,814, filed as application No. PCT/US2013/038623 on Apr. 29, 2013, now Pat. No. 9,739,663.

(60) Provisional application No. 61/789,565, filed on Mar. 15, 2013, provisional application No. 61/794,196, filed on Mar. 15, 2013, provisional application No. 61/794,515, filed on Mar. 15, 2013, provisional application No. 61/640,682, filed on Apr. 30, 2012.

(51) Int. Cl.
| | |
|---|---|
| *A61B 5/00* | (2006.01) |
| *G01N 21/49* | (2006.01) |
| *A61B 5/145* | (2006.01) |
| *A61B 5/1455* | (2006.01) |
| *G01J 3/02* | (2006.01) |
| *G01N 33/49* | (2006.01) |

(52) U.S. Cl.
CPC ........ *A61B 5/14552* (2013.01); *G01J 3/0237* (2013.01); *G01N 21/49* (2013.01); *G01N 33/4925* (2013.01)

(58) Field of Classification Search
CPC ... A61B 5/0075; A61B 5/0205; A61B 5/0215; A61B 5/0295; A61B 5/145; A61B 5/14532; A61B 5/14552; G01N 21/49; G01N 33/4925

See application file for complete search history.

(56) References Cited

U.S. PATENT DOCUMENTS

| | | |
|---|---|---|
| 5,556,282 A | 9/1996 | Middlebrook |
| 5,830,132 A | 11/1998 | Robinson |
| 6,529,276 B1 | 3/2003 | Myrick |
| 6,687,000 B1 | 2/2004 | White |
| 2001/0020284 A1 | 9/2001 | Tsuda et al. |
| 2002/0045811 A1 | 4/2002 | Kittrell et al. |
| 2003/0114762 A1 | 6/2003 | Balas et al. |
| 2005/0162660 A1 | 7/2005 | Chou et al. |
| 2006/0079740 A1 | 4/2006 | Silver et al. |
| 2006/0079774 A1 | 4/2006 | Silver et al. |
| 2006/0152726 A1 | 7/2006 | Larson et al. |
| 2008/0146986 A1 | 6/2008 | Riga et al. |
| 2008/0287763 A1 | 11/2008 | Hayter |
| 2008/0300494 A1* | 12/2008 | Hatib .................. A61B 5/029 600/485 |
| 2009/0117571 A1 | 5/2009 | Solanski et al. |
| 2009/0124867 A1 | 5/2009 | Hirsh et al. |
| 2009/0194705 A1 | 8/2009 | Kiesel et al. |
| 2011/0190624 A1 | 8/2011 | Cinbis et al. |
| 2011/0301882 A1 | 12/2011 | Anderson |

* cited by examiner

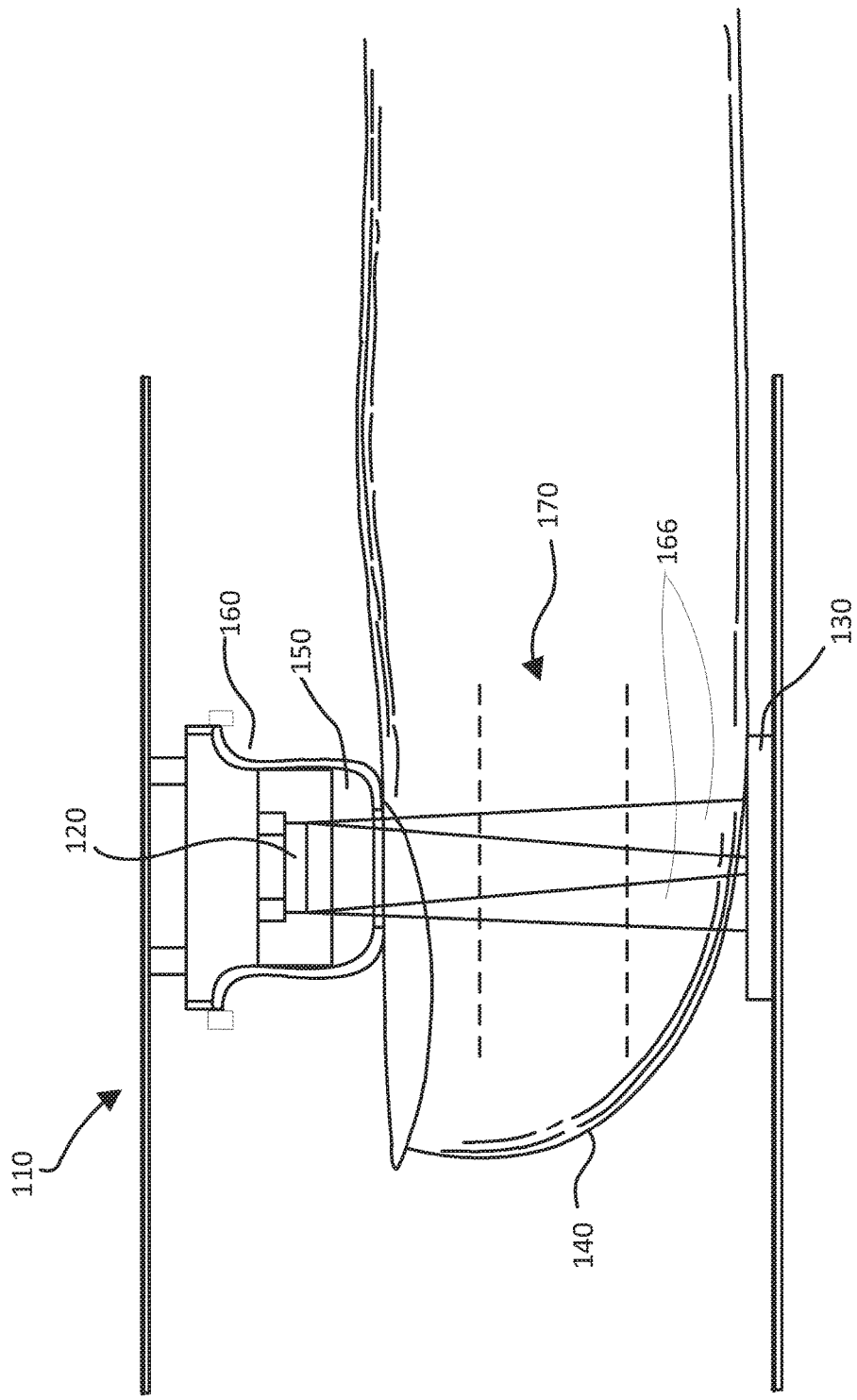

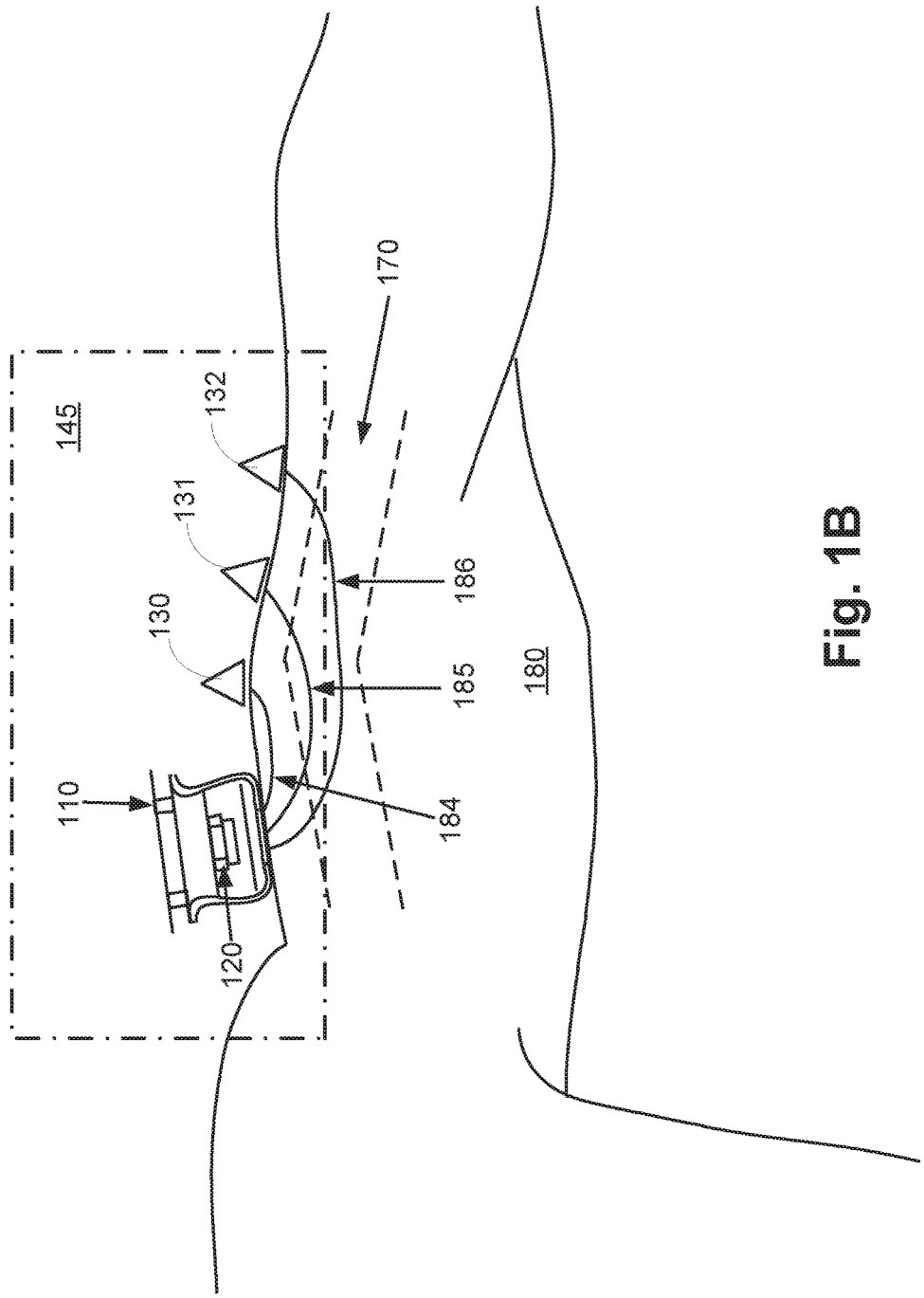

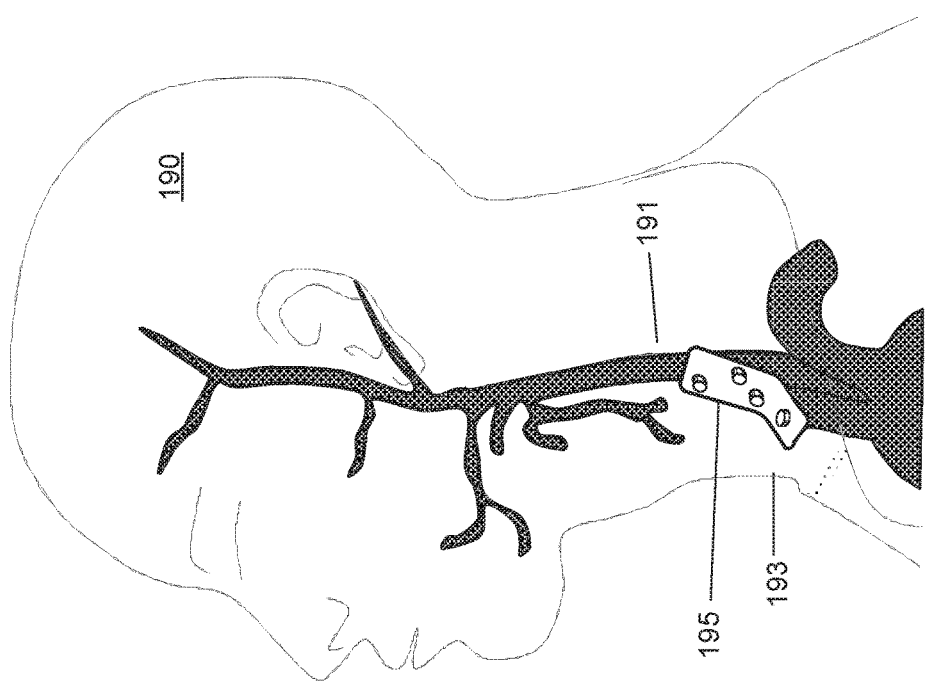
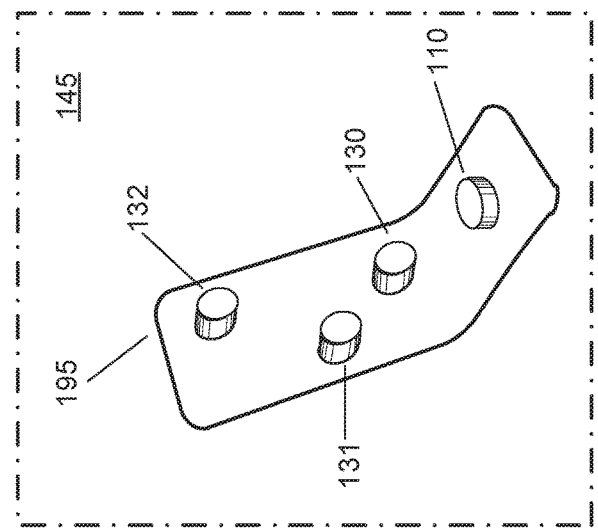
Fig. 1C

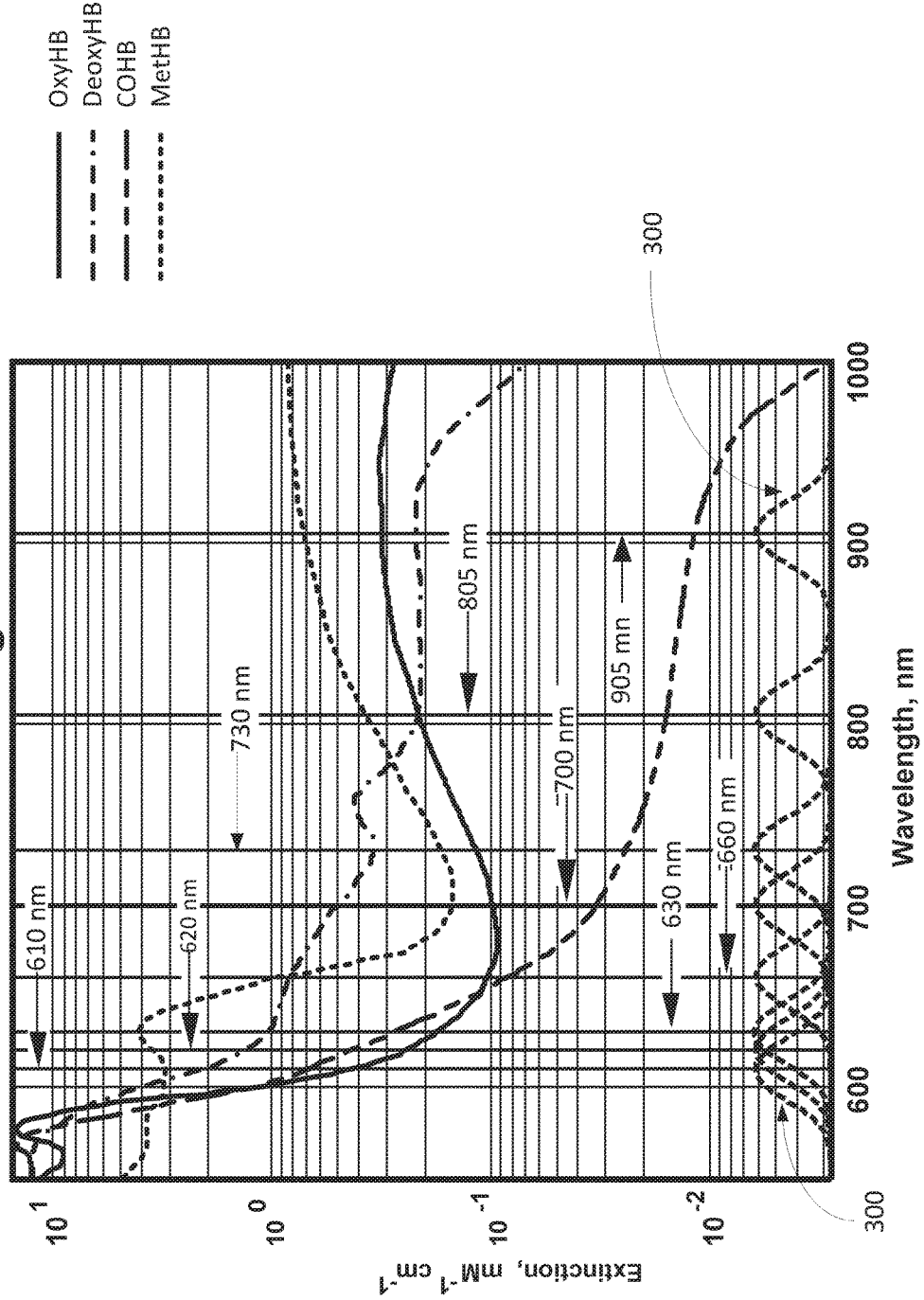

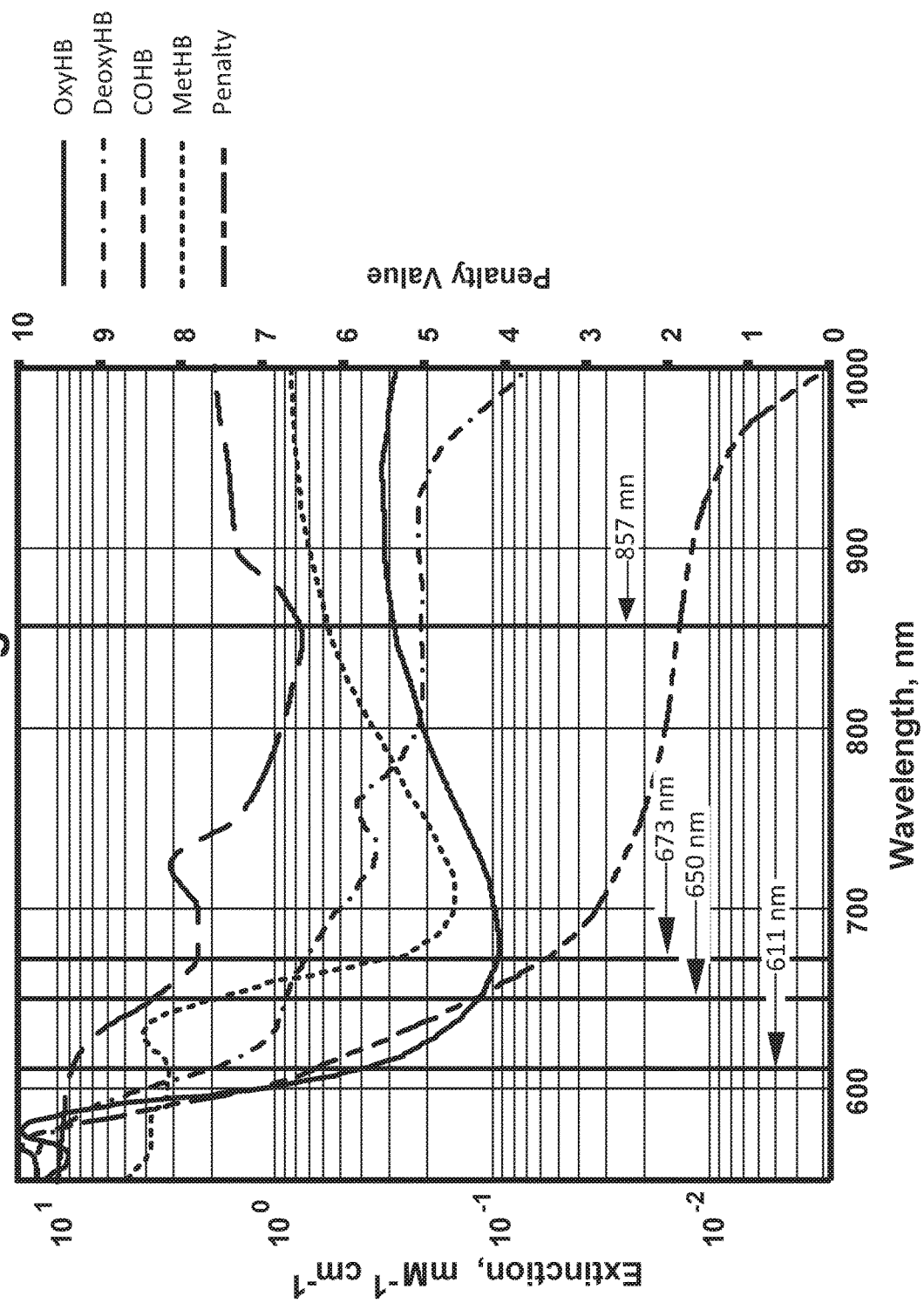

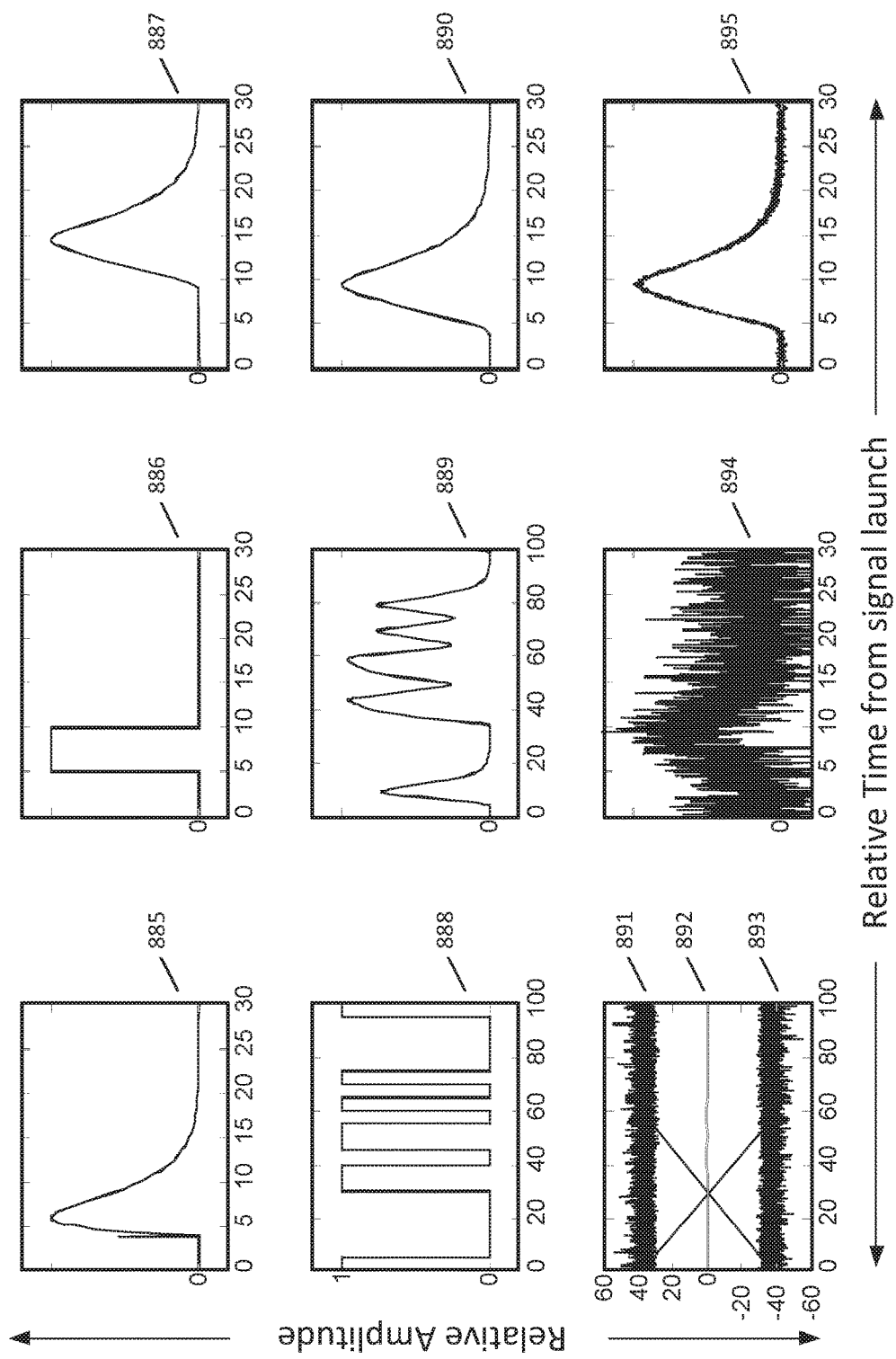

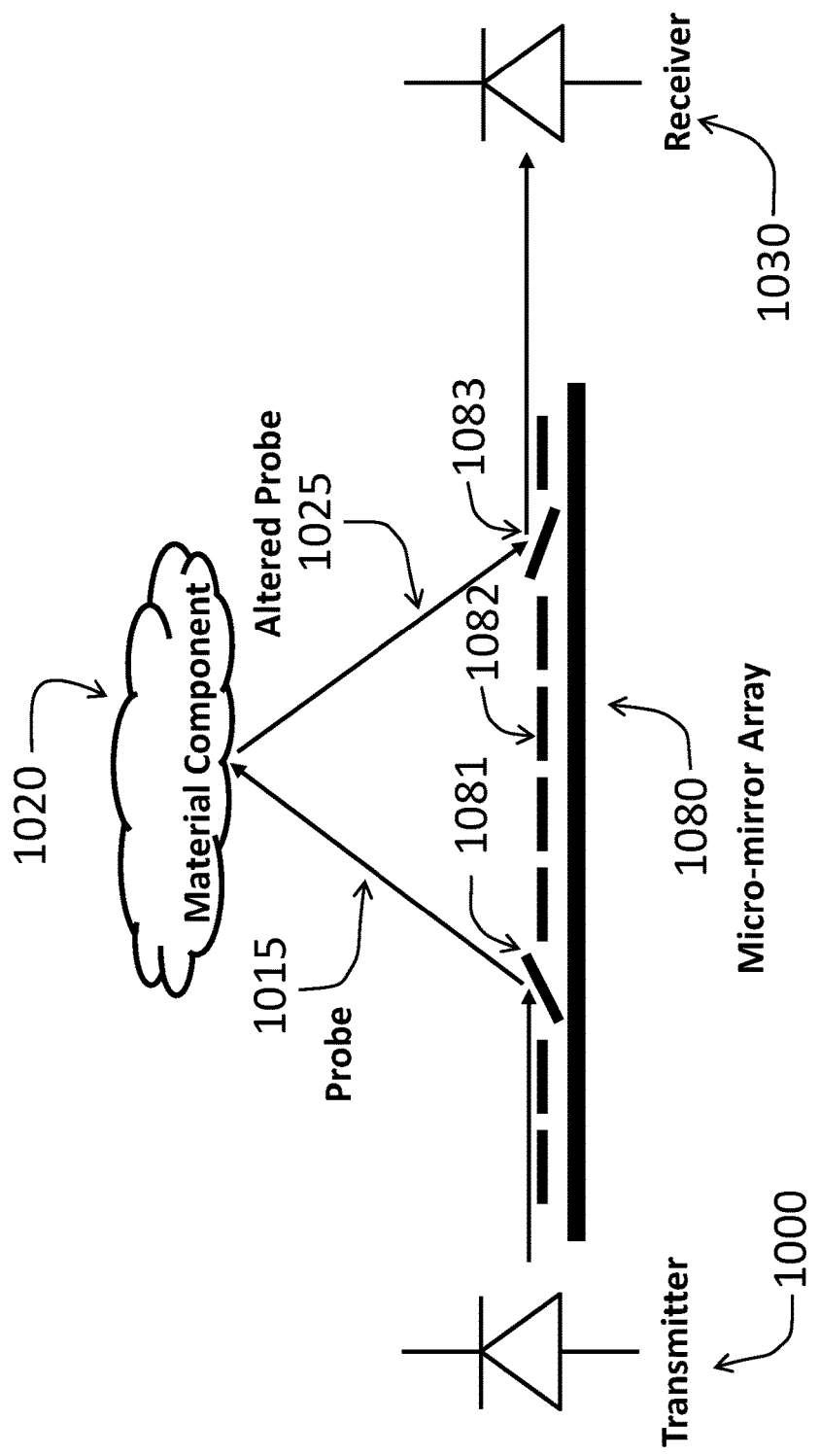

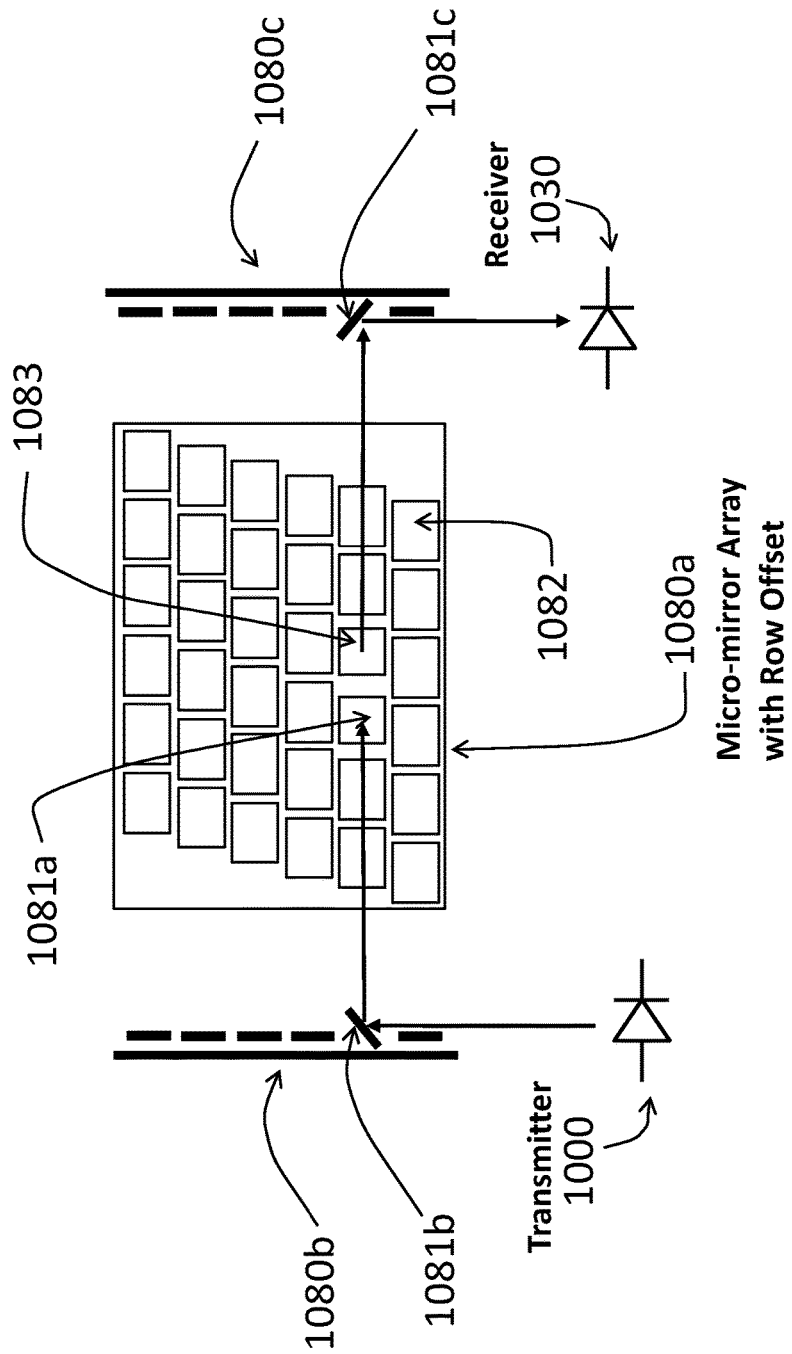

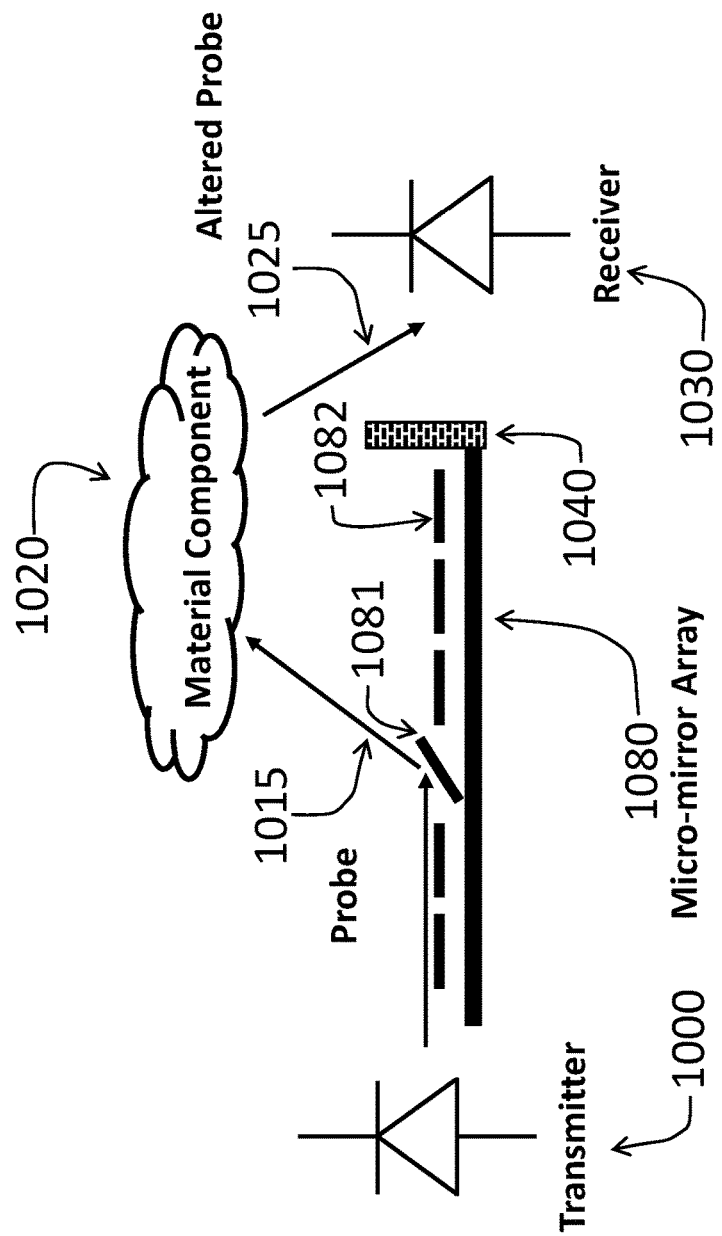

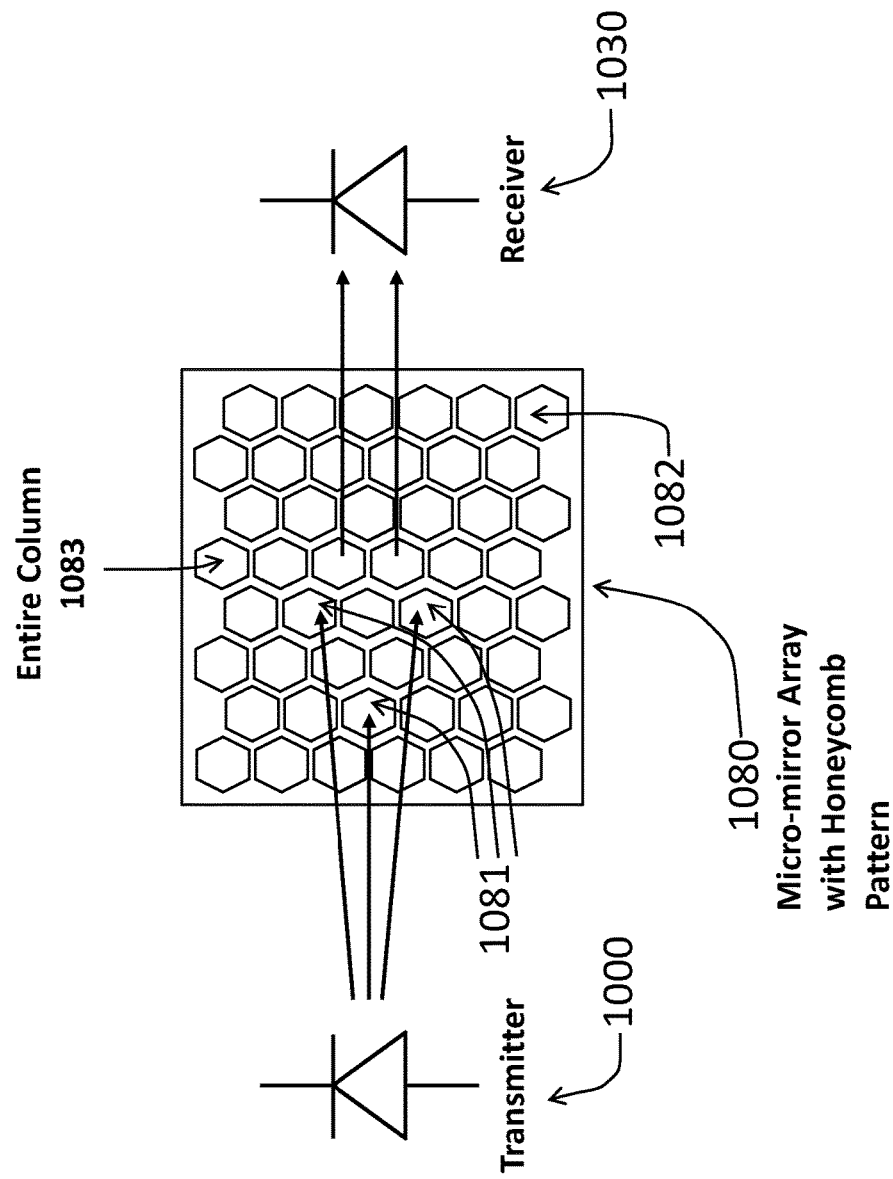

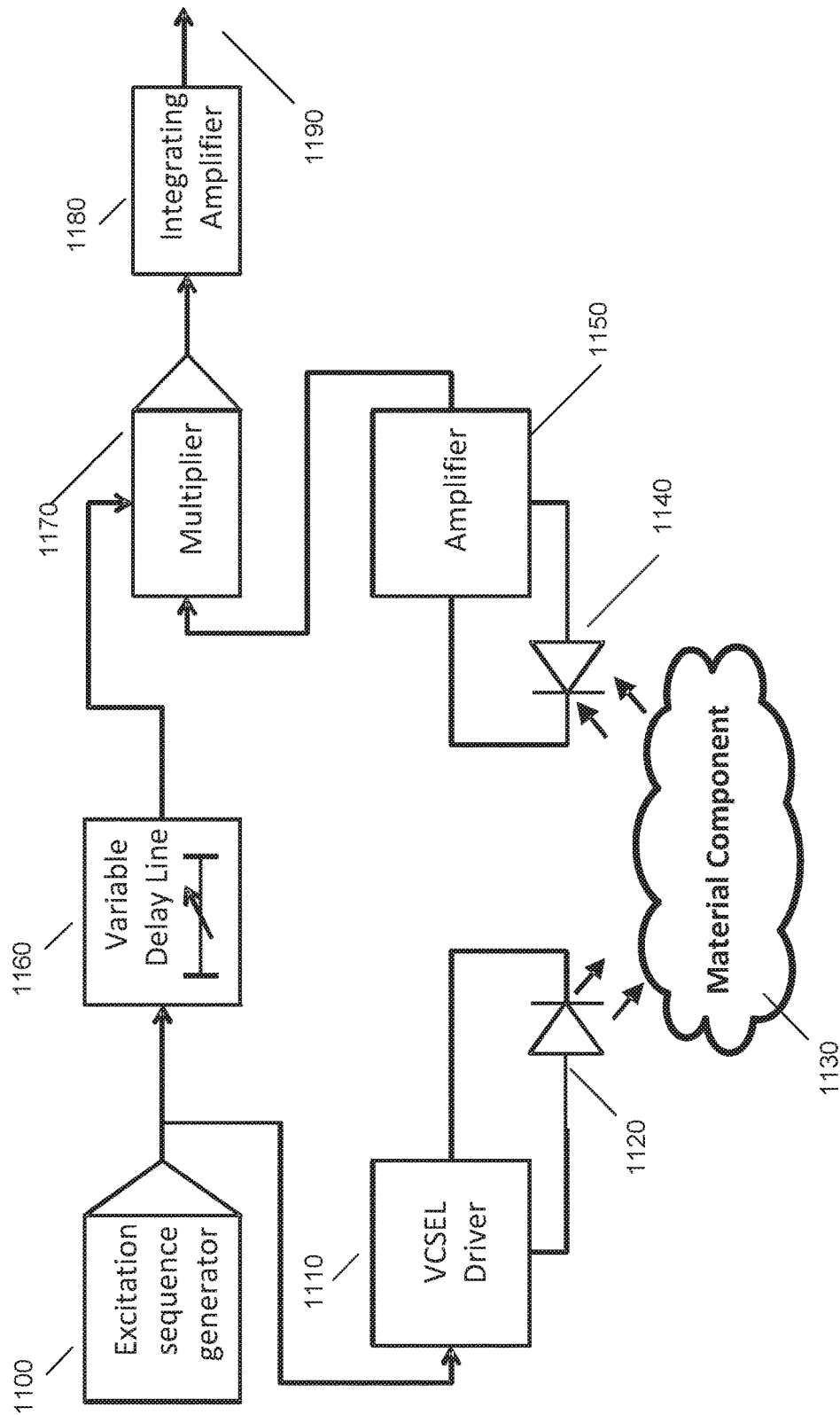

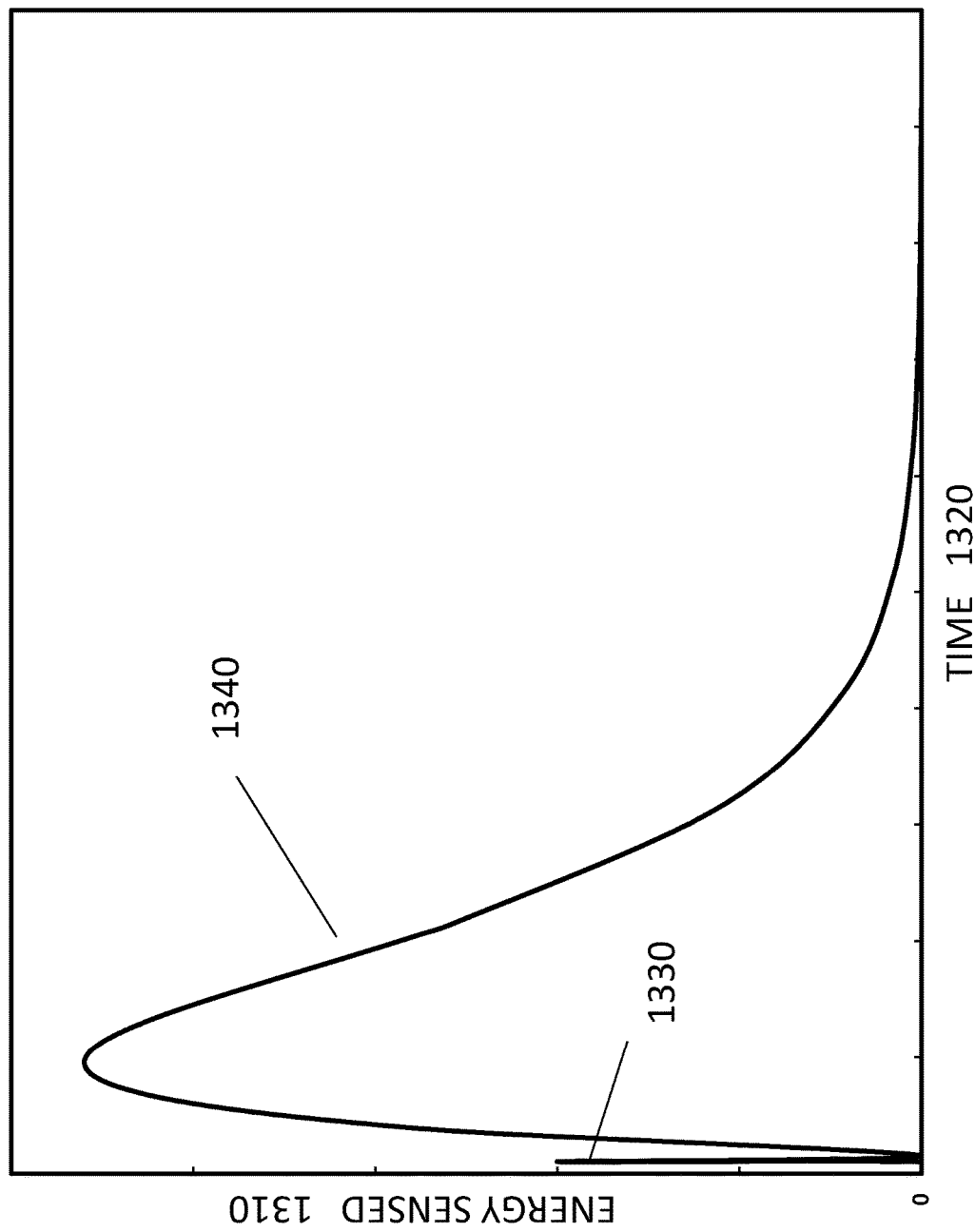

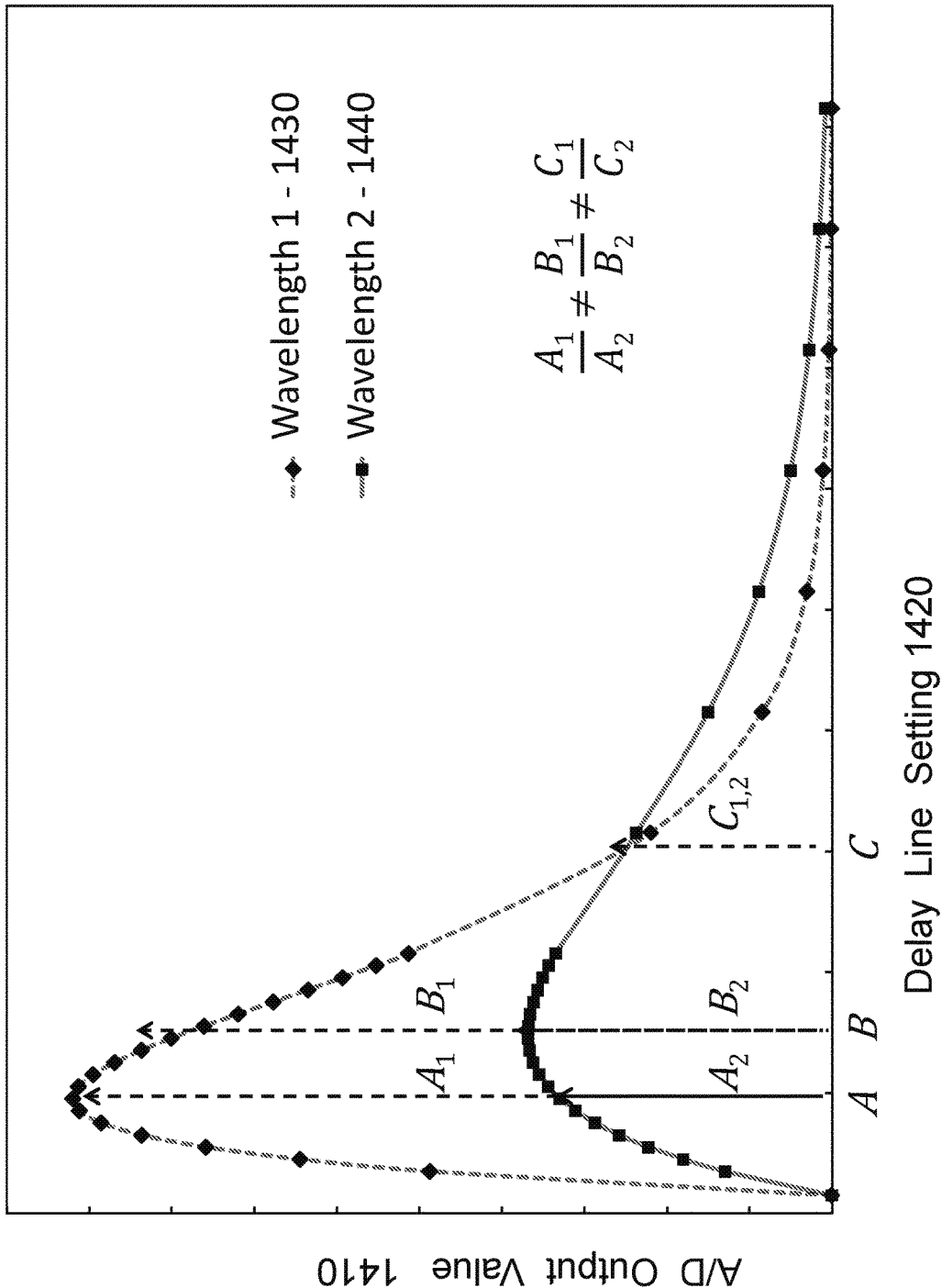

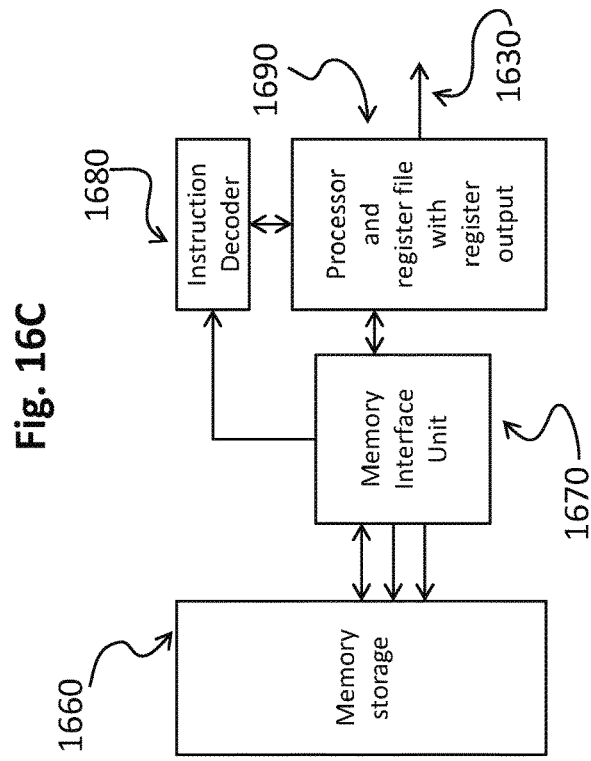
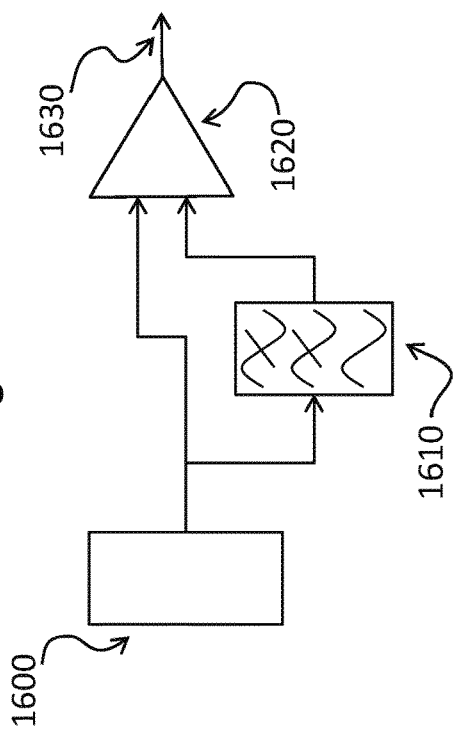
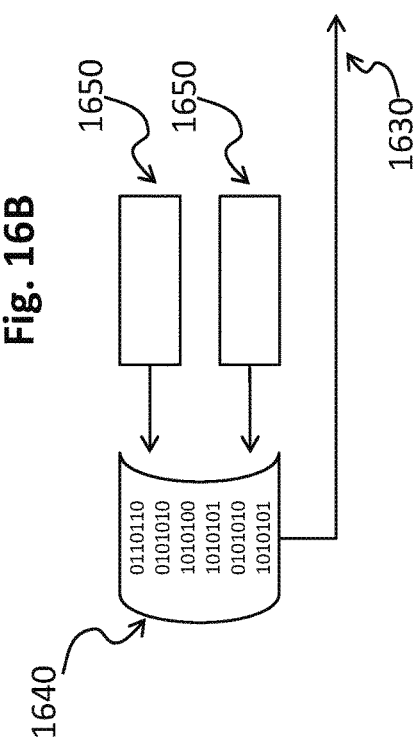

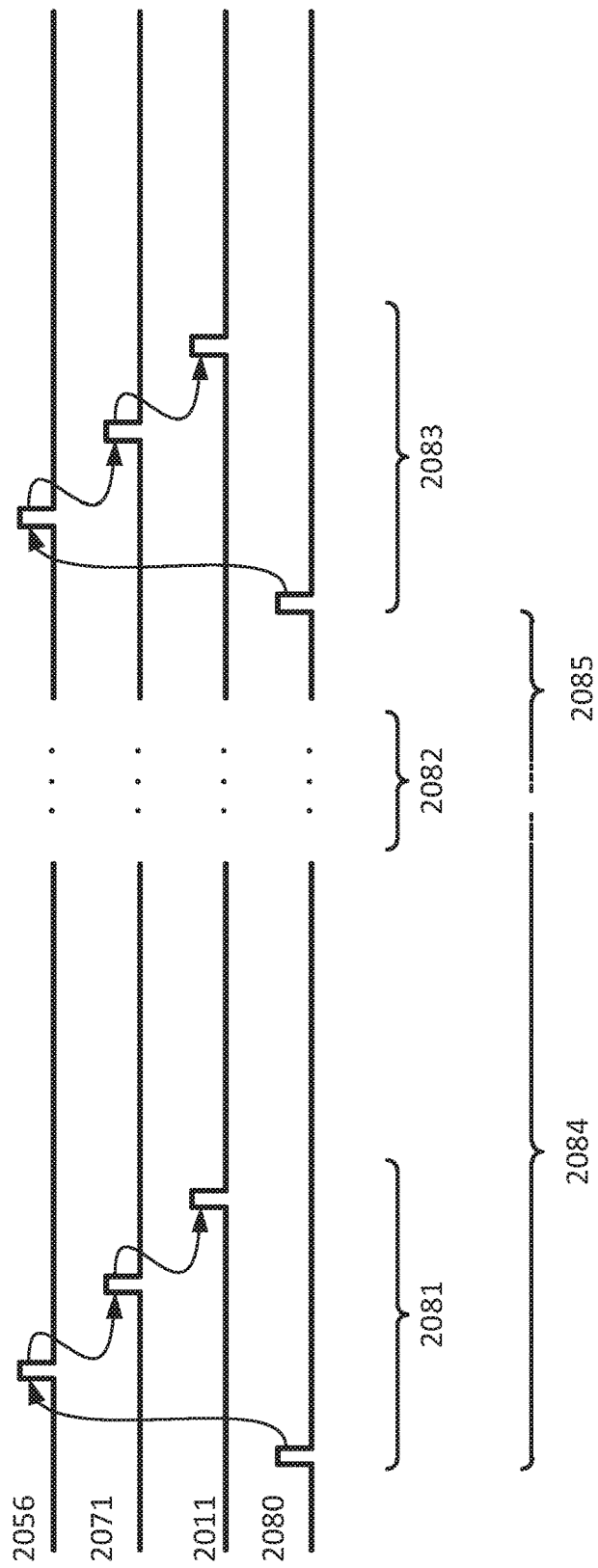

SPECTROMETRIC SYSTEMS AND METHODS FOR IMPROVED FOCUS LOCALIZATION OF TIME- AND SPACE-VARYING MEASUREMENTS

CROSS-REFERENCE TO RELATED APPLICATIONS

This patent application is a continuation from the U.S. patent application Ser. No. 15/643,193 filed on Jul. 6, 2017 and published as US 2017/0322084, which is a continuation from the U.S. patent application Ser. No. 14/397,814 filed on Oct. 29, 2014 and published as U.S. 2015/0109617, which is a national stage entry of International Patent Application No. PCT/US2013/038623 filed on Apr. 29, 2013, which, in turn, claims the benefit of and priority from U.S. provisional patent application Ser. Nos. 61/640,682, filed on Apr. 30, 2012; 61/789,565, filed on Mar. 15, 2013; 61/794,196, filed on Mar. 15, 2013; and 61/794,515, filed on Mar. 15, 2013. The disclosure of each of the abovementioned patent applications is incorporated herein by reference in its entirety.

TECHNICAL FIELD

The present invention relates to spectroscopic systems and methods of transmitting and receiving two or more concurrent signals and systems and methods enabling improved measurement focus localization of time- and space-varying spectrometer measurements, with additional uses for volume and volume variation measurements and challenge based property measurements.

BACKGROUND OF THE INVENTION

The assessment of arterial blood and tissue oxygen saturation has been shown to be critical for monitoring, diagnosing, and treating acute cardiovascular deficiencies, for example, but not limited to, low blood oxygen saturation due to chronic obstructive pulmonary disease (COPD), or in extreme cases, exsanguinations. Further, the time line over which physiological changes occur is indicative of underlying cardiovascular deterioration. While techniques exist that allow qualitative monitoring of the level of arterial blood and tissue oxygen saturation, the current medical practice appears to lack a tool for quantitative monitoring of deteriorating cardiovascular status from the initial cardiovascular event or acute trauma through arrival at a medical facility.

Spectroscopy was originally the study of the interaction between radiation and matter as a function of wavelength ("$\lambda$"). Historically, spectroscopy referred to the use of visible light dispersed according to its wavelength, e.g. by a prism.

Later the concept of spectroscopy was expanded greatly to comprise any measurement of a quantity as a function of either wavelength or frequency. Thus, it also can refer to a response to an alternating field or varying frequency ("$\nu$"). A further extension of the scope of the definition added energy ("E") as a variable, once the very close relationship "E"="h$\nu$" for photons was realized ("h" is Planck's constant). A plot or measurement of the response of a material or structure as a function of wavelength—or more commonly frequency—is referred to as a spectrum.

ISO Standard number 80601-2-61:2011 states, on page 34: "Current technology requires an adequate concentration of haemoglobin, a pulsatile change in blood flow, and light transmission through a tissue bed to approximate the in vivo haemoglobin oxygen saturation. PULSE OXIMETER EQUIPMENT is not typically capable of functioning effectively during cardiopulmonary bypass or at extreme low-flow states, and is not at present intended as a means for the measurement of blood flow or blood volume.

"Given these limitations, PULSE OXIMETER EQUIPMENT does not provide precise measurements of arterial haemoglobin saturation. The presently marketed in vivo PULSE OXIMETER EQUIPMENT is not a replacement for measurement of blood samples by in vitro optical oximeters. The values derived from pulse oximetry are not a measurement of blood or solid-tissue oxygen tension. Pulse oximetry provides no direct indication of oxygen delivery to tissue, or of tissue oxygen consumption."

Recent theoretical developments have pointed to the potential advantage of a spectroscopic device that uses multiple wavelengths of light to perform oximetry. Spectroscopic devices (including oximeters) using multiple well-chosen targeted wavelengths for operation have improved accuracy without the use of complex and/or large peripheral systems. There remains a need for a method enabling the selection of multiple optimal wavelengths for operation of a spectroscopic device configured to acquire and process data for use in quantitative cardiovascular measurements. The targeted selection of multiple wavelengths are also beneficial for optimization of the process of accurately and completely distinguishing between or among different analytes, referred to herein as analyte contrast.

Furthermore, there remains a need for improved measurement devices configured to operate to measure relative and/or absolute concentrations of material components in a sample. Conventional models appear to have ignored to incorporate the path length—and especially wavelength-based variations in the path length—of an electromagnetic wave traversing the measured sample. Incorporating this information can increase the sensitivity and accuracy of the measurements, providing a wealth of evaluation of the property of the material components of interest. Non-limiting examples of these material components are cells, proteins, hemoglobin, glucose, lipids, chromophores, water, pH, and gases such as hyperpolarized gases, carbon dioxide, carbon monoxide, and oxygen. Due to short transit times of signals through a tissue sample, and the rich information conveyed in the variations in the impulse and therefore the impulse response of the sample, the configuration of accurate and fine-grained (fine fidelity) measurement of the impulse response by a spectrometric system is not trivial but, if realized, may produce valuable results.

Given the capability to utilize the fine-grained information for more accurate measurements and assessments, there is a need for systems, methods, and apparatus that incorporate the ability to accurately measure very small signal levels and very short transit time thereby providing the details of the collective differential path lengths of the transmitted signals.

SUMMARY OF THE INVENTION

Embodiments of the invention include a method for operating a spectrometric device configured to generate electromagnetic waves (EMWs) and juxtaposed with a sample such as to measure at least one property of at least one material component of the sample using at least one of the EMWs. The method comprises: (i) in response to a first excitation sequence of pulses generated by a unit of the spectrometric device, transmitting a first EMW at a first wavelength by a transmitter associated with the spectrometric device; (ii) concurrently with transmitting the first EMW and in response to a second excitation sequence of pulses generated by the unit of the spectrometric device, transmitting a second EMW at a second wavelength by a transmitter associated with the spectrometric device; and (iii) acquiring said first and second transmitted EMWs as an aggregated input with a receiver associated with the spectrometric device. The method additionally includes the step of processing the received aggregated input with a data-processing unit associated with the spectrometric device by: (a) correlating the aggregated input with a time-controlled representation of the first excitation sequence of pulses to form a first identifier; (b) correlating the aggregated input with a time-controlled representation of the second excitation sequence of pulses to form a second identifier; and (c) calculating, based at least on first and second identifiers, the at least one property of the at least one material components of the sample.

Embodiments of the invention further provide an apparatus adapted to characterize first and second material components of a sample, which apparatus comprises two or more transmitters, each configured to concurrently transmit a respectively-corresponding electromagnetic wave (EMW) at a respectively-corresponding wavelength in response to an excitation sequence received by the two or more transmitters; a receiver adapted to receive the EMWs concurrently transmitted EMWs as an aggregated input; and a data-processing unit containing at least one correlator and structured to process the aggregated input. In such apparatus, a distinct correlator is used to quantify each EMW-component of the aggregated input such as to correlate the aggregated input is with a time-controlled representation of the excitation sequence to generate a data sequence and to uniquely quantify the generated data sequence for each EMW-component of the aggregated signal.

Embodiments additionally provide a system for measuring concentrations of first and second material components in a sample. The system includes a transmitter enabled to transmit a sequence of pulses in response to an excitation sequence received by the system; a receiver enabled to receive at least some of the transmitted sequence of pulses; and a device configured to quantify data representing the received pulses. The device contains a computational unit configured to (a) correlate the received pulses with the sequence of pulses; (b) aggregate multiple received pulses to quantify a magnitude of data representing pulses received over time; and (c) determine at least one value representing at least one of the first and second material components from the quantified magnitude.

Embodiments of the invention further provide a method for monitoring characteristics of a biological sample with a spectrometric system that includes at least one transmitter and at least one receiver operably juxtaposed with the sample. The method comprises receiving, with a data-processing unit of the system, an output from the at least one receiver caused by emission (by the transmitter), of at least one electromagnetic wave at at least one corresponding wavelength, where the output represents an optical property of the tissue. The method further includes receiving, with the data-processing unit of the system, reference data representing empirically-defined spectrally-dependent characteristic of the tissue. The method additionally includes determining an impulse response of the sample, the impulse response being associated with emission of the at least one electromagnetic wave by the at least one transmitter; and determining, as a function of time, a wavelength-dependent material parameter characterizing the sample based on the determined impulse response and the reference data. The determining, as a function of time, a wavelength-dependent material parameter characterizing the sample may include determining a wavelength-dependent material parameter characterizing the sample based on the averaged wavelength-dependent path length that has been estimated with the use of the determined impulse response.

In a related embodiment, the method additionally includes sampling a curve representing the determined wavelength-dependent material parameter as a function of time to obtain values of the material parameter at sampled points in time, and forming a weighting function by calculating variance values among the values of said material parameter at sample points in time, the weighting function being defined by said variance values as a function of time. Furthermore, the method may include determining, as a function of time, a modified wavelength-dependent material parameter characterizing the sample based on (i) the computed impulse response that has been weighted by the weighting function and (ii) the reference data.

Embodiments of the invention additionally provide an optical-path adjustment apparatus for modifying an optical path between a source of light and a receiver of light. Such apparatus includes: (i) the source of light with at least one transmitter enabled to emit a corresponding beam light at at least one corresponding wavelength; (ii) the receiver of light in optical communication with the at least one transmitter; and (iii) a device including (iii-a) a first plurality of selectively reorientable reflectors disposed such that, when each of the reflectors from the first plurality is in a corresponding reference orientation, the first plurality defines a first surface; (iii-b) a second plurality of selectively reorientable reflectors disposed such that, when each of the reflectors from the second plurality is in a corresponding reference orientation, the second plurality defines a second surface that is transverse to the first surface and substantially parallel to the corresponding beam of light. The first and second pluralities are in optical communication with the at least one transmitter such as to enable the apparatus to scan the corresponding beam of light which, when a reflector of the first plurality and a reflector of the second plurality are reoriented with respect to the corresponding reference orientations, has interacted with the reflector of the first plurality after having interacted with the reflector of the second plurality.

Embodiments of the invention also provide an optical-data-collection apparatus. The apparatus includes an optical detector and a light irradiation system enabled to deliver a beam of light from a starting point to the optical detector such as to scan an object that has been positioned at an intermediate point along a direction of propagation of the beam between the starting point and the optical detector. The light irradiation system contains at least one light transmitter defining the starting point, and a plurality of spatially reorientable reflectors disposed such that, when at least three of said reflectors are in respectively corresponding reference states of orientation, the at least three of said reflector define a plane that is substantially parallel to the beam of light. In a specific embodiment, the light irradiation system enables controlling a distance traversed by the delivered beam that has scanned the object by reflecting the beam with a reflector from the plurality to redirect the beam towards the optical detector.

BRIEF DESCRIPTION OF THE DRAWINGS

FIG. 1A is a diagram schematically illustrating an embodiment of a vertical cavity surface emitting laser (VCSEL) based oximeter.

FIG. 1B is a diagram schematically illustrating an alternate embodiment of a VCSEL-based oximeter.

FIG. 1C is a sketched side view of the human head, neck, shoulders, and a portion of the arterial circulation system; as well as the sensor 145 configured to monitor closely the concentration characteristics due to the blood flow in the carotid artery of the arterial circulation system.

FIG. 3A is a graph illustrating a choice of eight operational wavelengths in a pulse oximeter of the related art employing LEDs.

FIG. 3C is a graph illustrating an optimal choice of spectrally independent bandwidths of a light-based spectroscopic device, determined with an algorithm of the invention. In addition, the graph shows the "penalty" curve (the "cost" curve, or the "figure of merit" curve) representing operational cost of employing such spectroscopic device

FIG. 8C is a set of graphs illustrating the ability of a system of the invention to receive and recover the impulse response from additive noise.

FIG. 10A is a diagram illustrating an embodiment of apparatus configured to precisely control the distance from the light-scattering material component to a receiver.

FIG. 10B is a diagram illustrating an addition to the embodiment shown in FIG. 10A that enables the precise control of the distance from the light-scattering material component to a receiver in two dimensions.

FIG. 10F shows the embodiment of FIG. 10A with an auxiliary barrier introduced in a path of light.

FIG. 10I shows a top plan view of another embodiment of the invention having a micro-mirror array with hexagonal mirrors arranged in a honeycomb fashion.

FIG. 11 is a diagram illustrating components of a spectrometric system utilizing a variable delay to recover the impulse response of a sample to an interrogating input.

FIG. 13 is a graph illustrating the form of an impulse response of an optically measured sample using an embodiment of the invention.

FIG. 14 is a graph illustrating the variation of measurement output of two wavelength sources plotted with respect to the delay value of FIG. 11.

FIG. 16A is a diagram showing an alternative implementation of an excitation sequence generator.

FIG. 16B is a diagram showing an alternative implementation of an excitation sequence generator.

FIG. 16C is a diagram showing another alternative implementation of an excitation sequence generator.

FIG. 20C is a timing diagram illustrating the control signal sequence constraints for the system operation of 20B.

DETAILED DESCRIPTION

Figure 2:
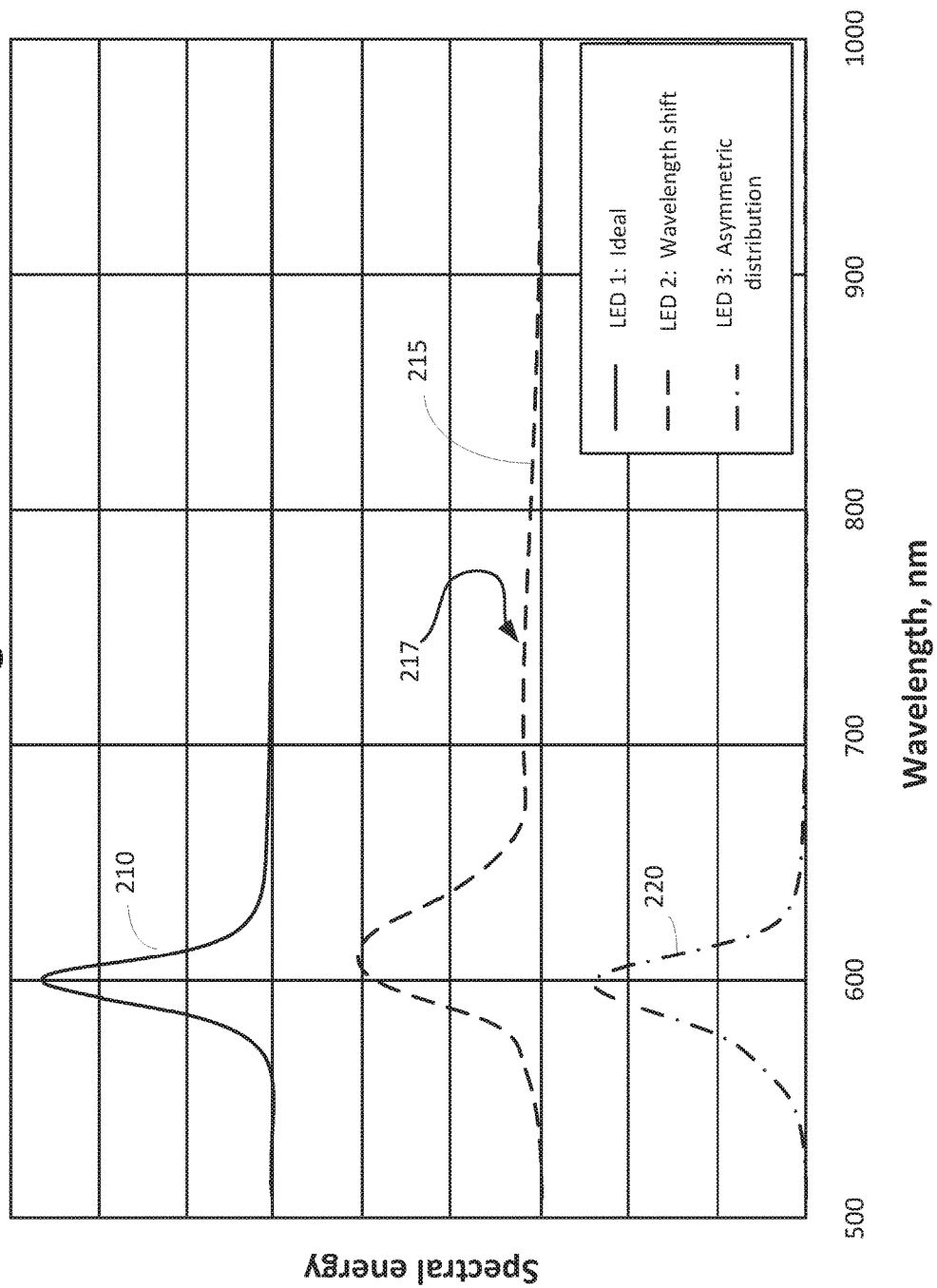
FIG. 2 is a graph illustrating the spectral energy distribution of three light emitting diodes (LEDs).

References throughout this specification to "one embodiment," "an embodiment," "a related embodiment," or similar language mean that a particular feature, structure, or characteristic described in connection with the referred to "embodiment" is included in at least one embodiment of the present invention. No portion of this disclosure, taken on its own and/or in connection with a figure, is intended to provide a complete description of all features of the invention.

In the drawings, like numbers represent the same or similar elements wherever possible. No single drawing is intended to support a complete description of all features of the invention. In other words, a given drawing is generally descriptive of only some, and generally not all, features of the invention and may, for the purposes of simplification of the drawing, contain not all elements of a particular view or all features that can be presented. The invention may possibly be practiced without one or more of the specific features of the invention. Although a particular detail of an embodiment may not be necessarily shown in each and every drawing describing such embodiment, the presence of this detail in the drawing may be implied unless the context of the description requires otherwise. The described single features, structures, or characteristics of the invention may be combined in any suitable manner in one or more further embodiments.

Moreover, if the schematic flow chart diagram is included that illustrates the processing flow, the order in which processing steps or particular methods occur may or may not strictly adhere to the order of the corresponding steps shown.

The invention as recited in claims or clauses appended to this disclosure is intended to be assessed in light of the disclosure as a whole. While the invention may be described in reference to examples of an oximeter device, it is understood that, in general the scope of the invention covers, generally, a device generating and optionally detecting electromagnetic radiation.

The assessment of arterial blood and tissue oxygen saturation has been shown to be critical for monitoring, diagnosing, and treating acute cardiovascular deficiencies, such as chronic obstructive pulmonary disease (COPD), or in extreme cases exsanguination, for example. Further, the time line over which physiological changes occur is indicative of underlying cardiovascular deterioration. While techniques exist that allow for qualitative monitoring of the level of arterial blood and tissue oxygen saturation, the current medical practice appears to lack a tool for quantitative monitoring of deteriorating cardiovascular status from the initial cardiovascular event or physical trauma through arrival at a medical facility. Recent theoretical developments have pointed to the potential advantage of multi-wavelength oximeters, as a way to improve accuracy without extremely large devices. In addition to shortcomings of the commercially available multi-wavelength techniques described above, the determination of wavelengths at which the commercial oximeters operate is somewhat arbitrary and, as proven by practical use, results in the mixing of spectral data acquired from the patient. As a result, the data processing and retrieval of vital information is unnecessarily complicated. Currently used methodologies are therefore quantitatively suboptimal.

Pulse oximetry is generally used to continuously monitor the arterial blood oxygen saturation of the patient. The "pulse" comes from the time-varying amount of arterial blood in the tissue during the cardiac cycle. Typical pulse oximetry sensors employ a photodetector and a light source producing light at two or more wavelengths to measure the light that scatters and/or is transmitted through blood-perfused tissues. Wavelength selection traditionally emphasizes sensitivity to changes in arterial oxygen saturation ($SaO_2$, $SpO_2$), with at least one of the emitted wavelengths chosen to fall within the spectral region where the absorption coefficient of oxygenated hemoglobin (i.e., $O_2Hb$), is markedly different from that of deoxygenated hemoglobin (i.e., HHb). One example of a choice commonly practiced for the multiple sources of light for pulse oximetry is to use two light-emitting diodes (LEDs), one generating light with a spectrum centered at about 660 nm and the second LED generating light with a spectrum centered at about 900 nm.

It is also possible to measure other analytes in the arterial blood, such as dyshemoglobins (i.e., MetHb and COHb), with at least one additional wavelength for each analyte.

Oximeters may employ vertical cavity surface emitting lasers (VCSELs). The beam of light emanating from a traditional edge-emitting (also known as in-plane) laser device is usually elliptical in cross section and is often astigmatic. The angle of divergence of a beam from an edge-emitting laser is significant (on the order of 30 degrees by 10 degrees) thereby reducing the efficiency of coupling into an optical fiber. In contrast, a VCSEL device uses a shaped aperture to provide a more constrained light path, which results in a beam of circular cross section and of sufficient diameter to make the beam generally less divergent, typically at about a 10 degree angle. Operational characteristics of VCSELs are not discussed here in any more detail.

FIG. 1A illustrates schematically a measurement probe module 110 in which the laser diodes are an integral part of the probe. The probe module 110 contains one or more VCSELs 120, optionally spatially configured in a predetermined pattern or array. Each of the present VCSELs 120 generates a beam of light substantially centered at a selected wavelength. The probe module 110 also contains a light detector 130 configured to receive and detect light emitted by the laser diode(s) 120. The light detector 130 may include at least one of any suitable detector component, such as a photomultiplier tube (PMT), an avalanche photodiode, and a PIN diode, for example, and in a specific case may include an array of such detectors. The probe module 110 also contains a connector (not shown) adapted to operably cooperate the probe module 110 with a cable (not shown) that interconnects the probe with a monitor (not shown). The probe module 110 is shown to be juxtaposed to the patient's perfused tissue 140 (shown as a finger, for illustration purposes only). The probe module 110 is adapted to operate in the transmission mode (with the array of laser diodes 120 on one side of the finger 140 and the light detector 130 on the other side of finger 140). Alternatively, the probe may be adapted to operate in the reflectance or backscatter mode (where the elements 120 and 130 are positioned on the same side of the perfused tissue 140). The array of laser diodes 120 may include a diffuser 150 held in place by a mount 160. The diffusion of the light output is to ensure that light portion 166 generated by the array of laser diode light emitting devices 120 is not spatially concentrated and cannot cause harmful effects if mistakenly redirected to the patient's eyes. The change in the path length of the light portions 166 as they pass through the arteriolar bed 170 is a figure of merit used for determination of the concentration of blood analytes. The close spacing of the laser diodes in the array 120 results in the plurality of light beams produced by the laser diodes traversing substantially a common path through the arteriolar bed 170, which improves the accuracy of the measurements.

Referring to FIG. 1B, the probe module 110 is juxtaposed to the patient's tissue 170 (shown as an upper arm 180, as an example only) and multiple light detectors 130 are arranged in a predetermined geometry (e.g., array (square or rectangular), triangular, and pentagon) along the same surface of the upper arm 180. Optical paths 184, 185, and 186 determined by propagation of light from the light source 120 to the light detectors 130, 131, and 132 respectively, may traverse substantially different depths of the tissue 170 and, possibly, the arteriolar bed. The light detectors can generally be positioned at predetermined distances one from another. In this case, a pulse wave propagating through the tissue 170 is separately detectable by the spatially separated light detectors 130, 131, and 132. The time differences in the pulse-based analyte composition data associated with light received by these detectors is used to determine various characteristics of the status of the patient such as, for example, cardiac stroke volume and beat-to-beat variation of cardiac stroke volume. Body locations at which the probe is placed may differ, depending on the application.

It is appreciated that sources of monochromatic light are generally desirable for use as emitters in an oximeter to avoid overlap of the spectral distributions among the emitters and to provide precise coordination of the spectral bandwidth of a given emitter with respect to the hemoglobin extinction spectral distribution curves. In particular, the full-width half-maximum (FWHM) value of an LED bandwidth typically exceeds at least several tens of nanometers. In contrast, the FWHM of a VCSEL's bandwidth is approximately 1 nm. In addition, the LEDs are typically manufactured without tight quality control of the central wavelength of the corresponding bandwidth because conventional applications of these light sources are in display technologies, not in quantitative measurement systems requires an operation at predetermined wavelength(s).

As another example, the operational variations in central wavelengths, bandwidths, and shapes of spectral curves among LEDs that in other applications may be presumed to be substantially identical, in applications such as those described below may significantly differ. To this end, FIG. 2 shows an example of spectrum 210 of an idealized LED. The curve has a symmetrical bandwidth centered at 600 nm. A second curve 215 corresponds to measurements of a nominally 600-nm-centered spectrum of an LED as manufactured. The imperfections of the LED-fabrication process result in a red shift of the central wavelength of the spectral band of the curve 215 as compared to that of the idealized curve 210, and in addition, a visibly present spectral output above 700 nm. The tail end 217 of the spectral emission curve 215 can have a measurable effect on the received signal from the perfused tissue. The magnitude and extent of the tail 217 portion of the spectral emission curve 215 is difficult to predict, measure, and account for as compared to the signal output at the nominal central wavelength. Yet another spectral curve 220 corresponding to a third LED, the spectrum of which is nominally centered at a 600 nm wavelength illustrates asymmetry of the spectral output with respect to the corresponding central wavelength. In contradistinction to LEDs, VCSELs can be manufactured with predictable and repeatable spectral outputs, both in terms of central wavelengths and bandwidths.

Another complicating factor is that the LEDs are mounted in the probe module, and are juxtaposed to the patient's skin. The LEDs are therefore subject to significant temperature fluctuations during the operation of the probe module, which may cause changes in wavelength output by the LEDs. This effect can introduce a dynamic variation across the LED array and cause a measurable source of error. Finally, another source of error is the so-called "venous prefiltering," wherein the spectral outputs of the LEDs are unevenly and unpredictably attenuated across the span of generated wavelengths by the venous and non-pulsatile arterial components of the blood. Such attenuation of light is a function of the oxygen saturation of the blood and wavelength of the light, varies from subject to subject, is temporal in nature, and varies within a given patient and across patients. The arterial blood flow is highly variable in the extremities of a patient, where the pulse oximetry readings are taken. The difference in oxygen saturation between arterial and venous components of the blood can be from as little as less than one percent to greater than twenty-five percent. With greater spectral bandwidth of the light source comes greater potential error from this source of error. Sources of errors are inherent in the LEDs as well as in the method of placing the LEDs on the patient's appendage to perform readings.

Figure 3B:
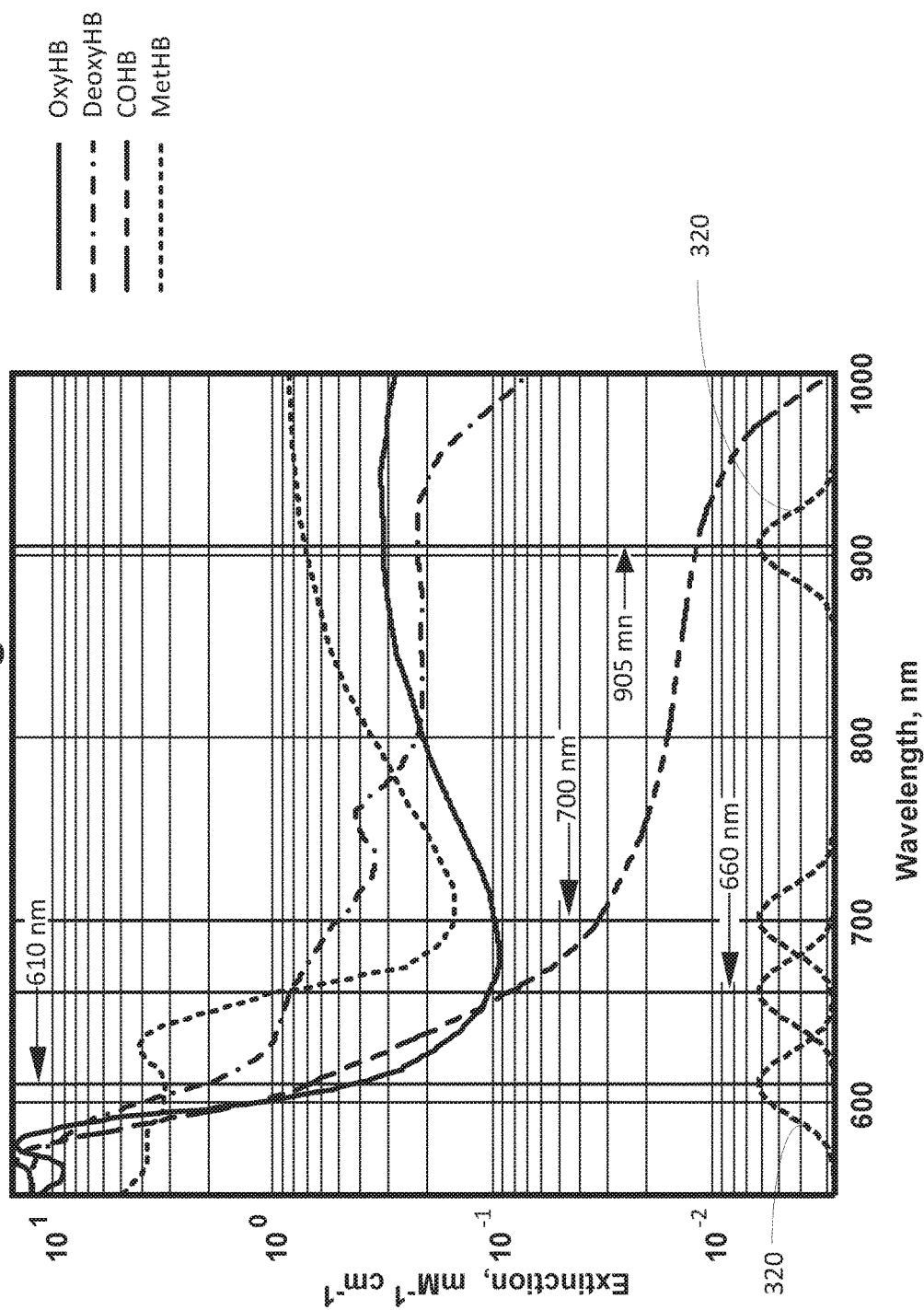
FIG. 3B is a graph illustrating a smaller number (four) of operational wavelengths for oximeters of FIG. 1A and FIG. 1B that still provide for adequate operation. The reduction of the number of the operational wavelengths is achieved with the use of an algorithm of the present invention.

Accordingly, selection of the multiple operating wavelengths, at which a source of light (or a combination of sources of light) of a pulse oximeter should operate, becomes of critical importance. To this end, FIG. 3A presents a graph showing spectral distribution curves for four blood analytes (oxyhemoglobin, OxyHb; deoxyhemoglobin, DeoxyHb; carboxyhemoglobin, COHb; and methemoglobin, MethHb) and schematic indication of eight wavelengths (610 nm, 620 nm, 630 m, 660 nm, 700 nm, 730 nm, 805 nm, and 905 nm) and eight spectral distributions (labeled, collectively, as 300) that respectively correspond to the eight LED sources employed in a commercially-available hospital oximetry system. It is appreciated that the significant spectral overlap of the LEDs' light outputs (presumably centered at 610 nm, 620 nm, 630 m, 660 nm, 700 nm, 730 nm, 805 nm, and 905 nm) results in spectral mixing of the acquired data and at best, merely contribute to signal averaging to reduce background noise. In fact, as established by the methods and algorithms discussed below, light beams at only four wavelengths chosen from the above-mentioned eight wavelengths are sufficient to acquire the practically-significant majority of data to identify and characterize multiple hemoglobin species. FIG. 3B illustrates such selection of the four spectral distributions 320 from the set 300 of FIG. 3A. Using data acquired with the use of several different light sources operating at different wavelengths allows the user to obtain a solution representing multiple biochemical species.

While specific examples describing embodiments of the invention are presented below with applications to optical spectroscopy and, more specifically, oximetry, quantitative oximetry, or pulse oximetry of blood samples, embodiments of the invention can be used with other media (for example, gas or fluid) to identify and/or measure different analytes (for example, molecules or proteins). Although the particular implementations of the algorithm of the invention are described using matrix equations, the use of continuous equations for determination of one or more analytes is also within the scope of the invention. Similarly, VCSEL(s) could be replaced with other sources of light such as, for example, edge emitting semiconductor lasers, or light emitting diodes. Moreover, embodiments of the invention can be practiced with the use of different waves, not necessarily optical waves, such as radio waves or acoustic waves, for example.

When the sample under test includes biological tissue and/or blood, the properties of the sample determined with light at wavelengths that have been selected according to an embodiment of the invention are various. These properties include, for example, concentration of a functional or dysfunctional hemoglobin; glucose; a lipid; a protein; a chromophore; a gas (such as percent of oxygen or carbon dioxide); water, and pH level. Other properties that may be measured include normal or abnormal cell count and normal or abnormal protein levels. The scope of the present invention is not limited to biological tissue or the limited properties listed. The scope of the invention also includes measuring relative levels and quantitative amounts of material components in general, as present in living as well as non-living samples.

An embodiment of the invention providing for derivative processing may also provide for example, one or more of blood oxygen saturation level, blood glucose level, blood protein level, blood lipid level, total body water, central blood volume, concentration of fluorescent biomolecules or dyes, respiratory tidal volume, cardiac stroke volume, and beat-to-beat variation of cardiac stroke volume. The sample-probing waves can be varied by including time-based variations of position, angle, intensity, phase, and wavelength of the wave-emitting source. The sample may also be modified, for example, by introducing a calibrated amount of carbon monoxide (CO) to provide quantitative measurements of one or more properties of the sample. The scope of the present invention also includes recording the measurements over time, such that the time varying nature of the concentrations can be determined. Properties derived from this collection of data include heart rate, heart rate variability, stoke volume, stoke volume variability, and similar properties.

Implementations of an algorithm according to the present invention facilitate not only optimal optical detection of various species of hemoglobin that are found in chemical equilibrium with oxygen-saturated hemoglobin (oxyhemoglobin), such as deoxyhemoglobin (the desaturated form of hemoglobin) as well as dysfunctional methemoglobin, sulfhemoglobin, and carboxyhemoglobin (the latter being related to exposure to high environmental levels of carbon monoxide), but also enablement of determination of the relative percentage of each species in blood at any given time. To this end, a set of curves representing spectral distributions of the extinction coefficients (further referred to as absorption curves) for the multiple species of hemoglobin such as those illustrated in FIG. 3A. Understandably, to resolve multiple species from the optically-acquired spectral data one has to solve a system of equations. As an example, in the case of four hemoglobin species, at least four independent equations are required. To derive these equations, at least four sets of coefficients are needed to incorporate at least four linearly independent optical measurements of the spectral characteristics of a blood sample, and therefore at least four different optical wavelengths are required. The optical wavelengths, at which meaningful hemoglobin measurements can be performed, are in the range of about 450 nm to about 1000 nm. FIG. 3C illustrates examples of the absorption curves for the species of hemoglobin (specifically, curves of spectral dependence of extinction coefficients) and identifies optical wavelengths (as shown, 611 nm, 650 nm, 673 nm, and 857 nm) that are optimal in terms of resolving the four identified hemoglobin species with the lowest noise-to-signal ratio (NSR) or, alternatively, the highest signal-to-noise ratio (SNR). It is appreciated that a choice of different absorption curves and associated wavelengths of operation for the spectrometric device will correspond to a different NSR.

Analysis of the absorption curves of four hemoglobin species (e.g., oxyhemoglobin, deoxyhemoglobin, methemoglobin, and sulfhemoglobin) shows that any given species may define a high absorption figure of merit at some narrow range of frequencies, and a much lower absorption figure of merit at a different narrow range of frequencies. In order to measure and solve for the relative or absolute quantity of all four hemoglobin species simultaneously, ideally one has to select four linearly independent equations with four unknown wavelength-variables. One method to optimize the selection of wavelengths is to make these equations as linearly independent of one another as possible in order to yield the lowest NSR for all four measurements. Therefore, the four optical wavelengths should be chosen such that the respectively corresponding absorption curves have amplitudes, at these wavelengths, that differ from one another as much as possible. The wavelengths should be chosen such that each interaction of electromagnetic radiation (EMR) or electromagnetic waves (EMWs) with the analyte is captured. If all components are transparent to the EMR or EMWs at a particular wavelength, then that EMR or EMWs have very little interaction with the sample. If any of the analytes are substantially opaque at a given wavelength, the signal level received by a detector will be difficult to measure. Improving the combination of linear independence and the interaction of the energy with the analyte is captured by improving the propagation of variance in the system of equations. This is examined below in detail (and, in particular, in reference to Eqs. (29-39)).

According to Ward Cheney and David Kincaid (*Numerical Mathematics & Computing*, 7th Ed., Brooks Cole; Apr. 27, 2012), for matrix operations it is possible to compute a "condition number" that provides a gauge of the transfer of error in the input to the output of the operation. A system with a condition number of one is said to be well conditioned, higher calculated condition numbers indicate progressively ill-conditioned systems in solving the system Ax=b. If the linear system is sensitive to perturbations in the elements of A, or to perturbations of the components of b, then this fact is reflected in A having a large condition number.

In FIG. 3A, the condition number of the eight-wavelength solution was calculated to be 30.5; in FIG. 3B, the condition number was 33.1; in FIG. 3C, with optimally chosen wavelengths, the condition number was calculated to be 19.8; the larger the condition number, the more ill-conditioned the system. Note that in FIG. 3B, the choice of wavelengths was constrained to the choice of wavelengths included in FIG. 3A. While the condition number is higher in FIG. 3B than in FIG. 3A, other figures of merit, including the propagation of error, are much improved. The condition number is used here to illustrate one potential figure of merit. Note that without the constraint of wavelength choice, the condition number of FIG. 3C is improved in comparison with that of either FIG. 3A or FIG. 3B.

According to the idea of the invention, selection of the operating wavelengths for VCSELS for use in a pulse oximeter or optical spectrometer is carried out by forming a merit (or cost) function based on a cost-function approach that is not limited to, for example, the condition of the mixing matrix or propagation of variance. Some of the constraint parameters of the cost-function may include wavelength-specific penalty coefficients according to (i) manufacturability of the VCSEL or other components; (ii) bandwidth or spectral extent of the light source output; (iii) a central wavelength about which the bandwidth is substantially centered; (iv) transition areas that result in rapidly changing accuracy with minor changes in operating center wavelength; (v) differential path length or the average path that light of different frequencies traverses in the medium $\langle \delta \rangle$; (vi) optical path length error derived from the statistical distribution of path lengths associated with, for example, physiologically relevant changes in the medium; and (vii) analyte absorption equations. According to an algorithm of the invention, the devised overall cost-function applies all of these constraints (and additional constraints that may be required) at the same time in order to optimize the process of defining the operational wavelengths for the pulse oximeter or, more generally, a spectroscope for measuring spectrally dependent properties of material components.

The "Manufacturability" constraint parameter defines how easily, or likely, a VCSEL that operates at a chosen wavelength may be manufactured. In calculating the overall cost-function, a weighting or scaling (as discussed below, for example in reference to Eq. (40)) is performed if the chosen wavelength falls outside of the manufacturability constraining limits.

The "Bandwidth" constraint parameter facilitates the simulation of hypothetical VCSELs or LEDs or even a white light source to account for variance in the desired bandwidth and to allow for the optional input of actual light source profiles in-order-to test effectiveness in separating sharp transition regions.

The "Central wavelength" constraint parameter facilitates testing the effects of manufacturing tolerances on the performance of a given light source. If a particular type of spectral distributions has a large variance in central wavelengths, this parameter can be included as a constraint to minimize the error in the solution as a function of manufactured center frequency versus the desired central frequency.

The "Transition areas" constraint parameter takes into account the realization that the selection of a wavelength may be such that, in the vicinity of that wavelength, an absorption curve associated with the operation of the oximeter is rapidly changing (thereby introducing variability into the processing of acquired data).

The "Differential Path Lengths" constraint parameter accounts for the wavelength dependency of optical scattering coefficients, meaning that the optical path length will be different for each light source. In traditional oximetry, the path lengths are assumed equal and as such are not part of the consideration. However, in cases characterized by low oxygen saturation the difference in optical path lengths can result in a poor estimation of oxygen saturation. Accordingly, the algorithm of the invention takes into account a difference in path lengths corresponding to optical data acquisition at different wavelengths.

The "Interaction" constraint parameter accounts for the wavelength dependency of differentially excessive transparency and differentially excessive opaqueness of a sample or a material component of the sample such that there is either minimal interaction of an EM wave with the sample (transparency), or minimal level of signal received by a detection unit (opaqueness).

A method to minimize error in the solution utilizes the proposed algorithm. Such method includes simulated annealing, gradient descent (also known as steepest descent), and linear programming. In addition or alternatively, constraints such as full forward and inverse models using a Monte-Carlo approach are optionally included into or, alternatively, removed from a method depending on the desired system optimization, thereby to create a comprehensive understanding of the measurement of physiological variables. For example, constraints or penalties corresponding to a particular analyte need not be included in an overall cost-function if that analyte is not present in the medium.

Accordingly, as shown in FIG. 3C, a curve labeled as "penalty" represents a particular subset of a cost function, a scaling factor incorporated into the algorithmic process according to the invention to optimize the determination of the wavelength choice. This "penalty" function represents, for example, a consideration that lasers (and, in particular, VCSELS) at some wavelengths are easier to manufacture than lasers at other wavelengths. The use of the "penalty" function, as discussed below, effectively modifies the algorithm by shifting the selection of optimal laser wavelengths to minimize the penalty function or penalty figure of merit. If the optimization algorithm is run without inclusion of the penalty curve, the optimization process arrives at optimal wavelengths that may be quite different from those chosen without consideration of the penalty curve. Because of, for example, new laser manufacturing approaches, the shape of the penalty curve may change, and results of a new optimization may be determined by exercising the algorithm with the updated/changed penalty curve. If a valid solution requires the use of a laser source the manufacture of which is particularly expensive, the algorithm selects the corresponding wavelength and a "cost" threshold determines that the solution is not feasible provided a given design budget. Additional considerations can be incorporated into the statement of the problem, including other elements beyond manufacturing constraints on the optical sources, for example, relative optical responsiveness at varying wavelengths of, or manufacturing constraints on, the selected photodetectors that comprise the optical receiver portion of the system.

The wavelength selection process used to separate two distinct elements of blood (species of hemoglobin, also referred to herein as chromophores) is generally based on an empirical observation that measurements at one or more wavelengths are required to spectrally separate one or more chromophores. This observation serves as a basis for ensuring the minimal spectral mixing of the measured optical signals representing absorption of probing light by the one or more chromophores. As the number of chromophores of interest increases, so does the minimum number of wavelengths required to solve the system of wavelength-dependent equations. It has previously been documented in the open scientific literature to be computationally intractable to define more than a couple of chromophores on a limited subset of the wavelengths of interest, making the solution suboptimal by definition. However, according to the idea of the invention, the algorithm for selection of wavelengths for an oximeter does provide an optimized solution (corresponding to laser sources operating at optimally-defined wavelengths or, alternatively, laser sources available commercially and operating at wavelengths that are close to those defined by an optimization algorithm) based at least on minimizing the pre-determined figure of merit. An example of the pre-determined figure of merit is provided by propagation of variance from the measurements to the solution. The algorithm may be used to locate near-optimal solutions, or constrained solutions, that use particular wavelengths fixed as part of the solution. This approach may be advantageously used when a given set of VCSELs at fixed wavelengths are commercially available, and new wavelengths are available only at a considerable incremental cost. The algorithm can additionally be used to identify an optimal set of wavelengths, which can then drive the process of specially designing and manufacturing VCSELs that operate at central wavelengths corresponding to the wavelengths from the optimal set.

Figure 3D:
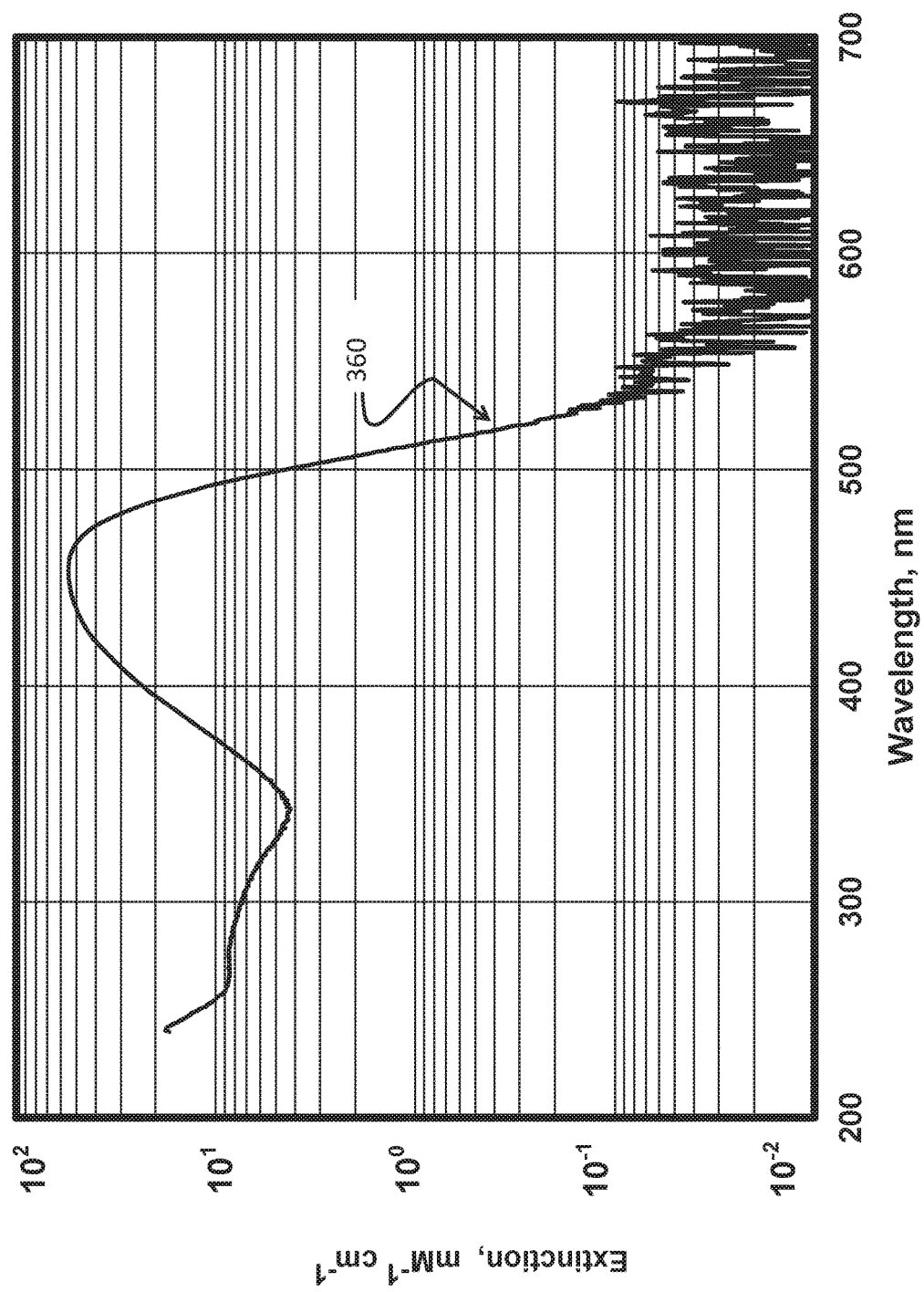
FIG. 3D is a graph illustrating the spectral distribution of the extinction coefficient characterizing Bilirubin (a possible confounding analyte) in chloroform.

When considering the choice of wavelengths at which the spectrometric device, used in a particular application, should preferably operate it is necessary to consider the material components of the sample to be measured. Some of these material components—referred to herein as potentially confounding components—are the material components of the sample the presence of which will affect the spectrum associated with the measurement(s) of the sample, the presence of which will affect at least one of the levels of the signal propagated through the sample, and the level of interaction of the signal with the sample. Such consideration requires the use of propagation of variance as opposed to the condition number. The curve 360 of FIG. 3D illustrates the optical extinction coefficients of Bilirubin in chloroform as they spectrally vary over the range from about 240 to about 700 nanometers. (Bilirubin is the yellow breakdown product of normal heme catabolism. Heme is found in hemoglobin, a principal component of red blood cells. Bilirubin is excreted in bile and urine.)

As can be empirically determined by the knee of the extinction curve 360 Bilirubin, as a material component of the measured medium, has greater extinction coefficients below 530 nm than above 530 nm. This characteristic illustrates some of the tradeoffs that are available with potentially confounding analytes. If the concentrations of the analytes are high enough to effect the measurements of the analytes of interest, then the error introduced by the range of potential concentration of the confounding analyte can be introduced as a spectrally-dependent cost of the measurement. This will lead the algorithms for determination of optimal wavelength(s) of operation of the spectroscopic device to choose wavelengths that are located in the spectral regions in which a given confounding analyte has little or no effect on the measurement. Alternatively, an additional wavelength (to account for a confounding material component of the sample) can be added to the algorithm, and the concentration of the confounding material component can be extracted from the other analyte determinations.

These two choices (providing a cost curve for interference, or adding the additional wavelength) are not mutually exclusive. It has been empirically found that if both are used as inputs to the algorithm when the additional wavelength is not needed, two of the wavelengths produced, as an output by the algorithm will be identical. Such optimization is a result of using propagation of variance as the figure of merit. As was shown in the discussion of FIGS. 3A, 3B and 3C, a smaller number of wavelengths well-chosen, based on the local optimization of a figure of merit representing operational cost of employing the device, improves the performance of the device.

Figure 4:
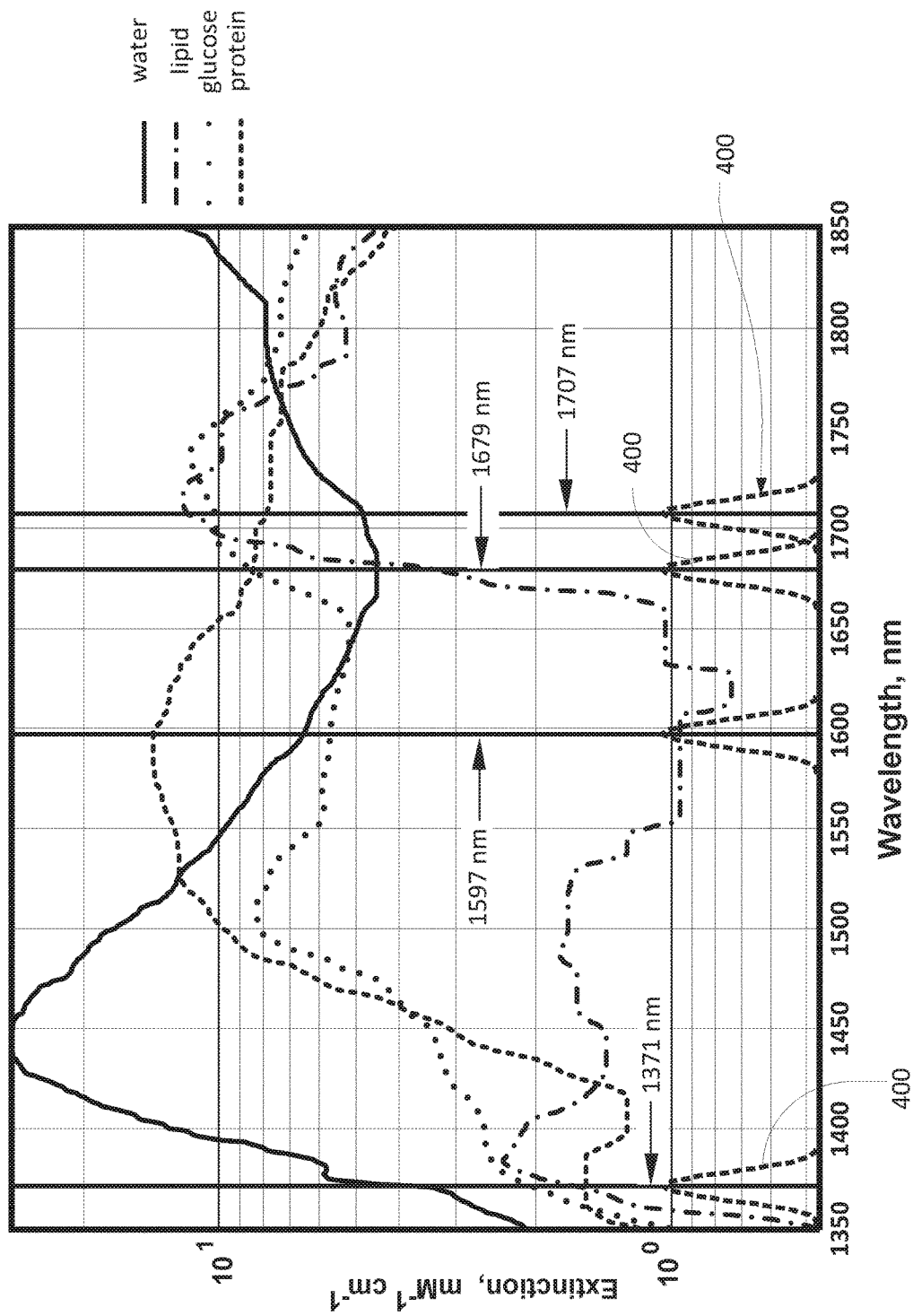
FIG. 4 is a graph illustrating an optimal choice of spectrally independent bandwidths of a light-based spectrographic measurement device, measuring glucose levels, determined with an algorithm of the invention

Optical noninvasive sensing methods facilitate detection of additional medically important, physiological and biochemical variables besides hemoglobin species. As one example, FIG. 4 offers a graph illustrating absorption curves for blood glucose, protein, and lipid in the near-IR range of 1350 nm to 1850 nm. The central wavelengths of spectral distributions 400 shown in this graph are longer than those in FIGS. 3A, 3B, and 3C because the differentiating extinction characteristics of the material components (that is, protein, lipid, and glucose) of interest exhibit themselves at longer wavelengths. An absorption curve for water is provided in FIG. 4 for comparison. It is expected, therefore, that given appropriate operating wavelengths, detection and measurements of glucose, lipids normal and abnormal proteins, as well as natural analytes, as well as manmade materials (for example certain chemical tags, markers, or dyes) in blood can be effectuated. In addition to the material components measured as shown in FIG. 4, other material components that can be measured include normal or abnormal cell counts. Finally, other concentrations such as percent of a chromophore, percent of a gas (such as oxygen or carbon dioxide), percent water, and pH level can also be measured. The above-mentioned material components are important as clinical parameters and in some cases as disease markers (for example, diabetes).

The solid vertical lines, marked with wavelength readings (such as 1371 nm, 1597 nm, 1679 nm, and 1707 nm) represent the central wavelength corresponding to four operating spectral distributions of light selected for detection of the above-mentioned species with the use of an optimization algorithm of the present invention. As the FWHM value for a VCSEL is on the order of one nm, the width of these vertical lines in the graph approximately represents the spectral distribution of VCSELs' light. The bell-shaped curves 400 (the peaks of which are substantially centered on the solid vertical lines), on the other hand, illustrate, in comparison, the broadband spectral distribution of LEDs that would be centered at the same wavelengths. The FWHM value for each LED is on the order of 50 to 100 nm or at least 50 times that of a VCSEL.

The use of these wavelengths, or a set of wavelengths determined to match the constraints described herein, that is an optimal or near optimal separation of the major material components, can be used as a non-invasive blood glucose level detector. The techniques described for multiple detectors 130 may be used.

Non-Scattering Absorbing Medium

As the light photons pass through a homogenous, lossy, nonscattering medium they are attenuated according to the attenuation coefficient $\mu_a(\lambda)$ of the bulk medium (BM) in relation to the traversed distance $\delta$, the irradiance of light changes in accordance with the Bouguer-Beer-Lambert exponential law, the probability of a photon being absorbed over a distance is $\Delta\delta$ is $\Delta\delta\mu_a(\lambda)$, and the mean free path between attenuating interactions $l_t(\lambda)$ is given by $l_t(\lambda_j)=\mu_a^{-1}(\lambda_j)$. As individual attenuating components or chromophores of the medium, denoted as $C_i$, are considered instead of the properties of a bulk medium, the properties of the bulk medium can be expressed as the summation of all N independent attenuating chromophores:

$$I(\lambda_j) = I_0(\lambda_j)\exp\left[-\sum_{i=1}^{N}\mu_a^{C_i}(\lambda_j)\delta^{C_i}\right]. \quad (1)$$

Often $\mu_a(\lambda)$ is replaced with the molar extinction or molar attenuation coefficient $\in(\lambda_j)$ [M$^{-1}$m$^{-1}$] to more easily allow formulation of the transmission of light as a function of concentration of the individual attenuating components [$C_i$] that comprise the nonscattering medium. For this substitution, for a given chromophore i, the attenuation A (in units of optical density, OD) and transmission coefficients T are related as $$A(\lambda_j) = \log_{10}\left(\frac{I_0(\lambda_j)}{I(\lambda_j)}\right) = \epsilon(\lambda_j, C_j)[C_i]\delta^{C_i}. \quad (2)$$

$$A(\lambda_j) = -\log_{10}T = -\log_{10}\left(\exp\left[-\sum_{i=1}^{N}\mu_a^{C_i}(\lambda_j)\delta^{C_i}\right]\right) = \frac{\mu_a^{C_i}(\lambda_j)\delta^{C_i}}{\ln(10)}. \quad (3)$$

Accordingly, $$\mu_a^{C_i}(\lambda_j)=\ln(10)\delta^{C_i}\in(\lambda_j,C_j)[C_i] \quad (4)$$

and $$A(\lambda_j) = \sum_{i=1}^{N}\delta^{C_i}\epsilon(\lambda_j, C_j)[C_i]. \quad (5)$$

If the optical density coefficient, A, is measured at multiple wavelengths, j=1 ... M, it is expressed in vector and matrix notations as $$A = \sum_{j=1}^{M}\sum_{i=1}^{N}\delta^{C_i}\epsilon(\lambda_j, C_j)[C_i] \quad (6)$$

and $$A=\in[C]\delta \quad (7).$$

Equation (7) can be re-written to account for bias G and noise N of the measurements, to result in $$A=\in[C]\delta+G+N \quad (8).$$

Given a known set of molar extinction coefficients, the measured values of optical density, and assuming that the non-scattering medium is homogeneous, the solution to Eq. (7) is provided by $$[C]=\in^{-1}A(\delta^{CBM})^{-1} \quad (9).$$

Scattering Non-Absorbing Medium.

In a non-absorbing medium, light intensity is reduced along a ballistic path according to the scattering coefficient $\mu_s(\lambda j)$ in relation to the distance $\delta$ traversed by the photons. The probability of a photon passing a distance $\Delta\delta$ without being scattered is $\Delta\delta\mu_s(\lambda_j)$ and, accordingly, $$I(\lambda_j) = I_0(\lambda_j)\exp\left[-\sum_{i=1}^{M}\mu_s^{C_i}(\lambda_j)\delta^{C_i}\right]. \quad (10)$$

The light scattering may be anisotropic, and the directionality of such scattering is described by the unitless factor g. With the use of a polar angle $\phi$ ($0\leq\phi\leq\pi$) and azimuthal angle $\psi$ ($0\leq\psi\leq2\pi$), g can be calculated as $$g = \frac{\int_{4\pi}p(\phi)\cos(\phi)\sin(\phi)d\phi d\psi}{\int_{4\pi}p(\phi)\sin(\phi)d\phi d\psi}. \quad (11)$$

where $p(\phi)$, which is the probability that a photon is scattered at an angle $\phi$ defined between the direction of incident light (the incident photon's unit vector) r and the scattered photon's unit vector r', is approximated by the Henyev-Greenstein function $$p(\phi) = \frac{1-g^2}{(1+g^2-2g\cos(\phi))^{3/2}} = \sum_{q=0}^{\infty}(2q+1)g^q P_q(\cos(\phi)). \quad (12)$$

The scattering data can be acquired with the use of, for example, an integrating sphere and then correlated with the results of inverse Monte-Carlo simulations. When g=1, the light is considered to be completely forward-scattered, and when g=−1, the light is considered to be completely backward-scattered.

Scattering Absorbing Medium

To account for both scattering and absorbing properties of the medium, the total coefficient of interaction between a photon and the medium can be expressed as $$\mu_t(\lambda_j)=\mu_a(\lambda_j)+\mu_s(\lambda_j) \quad (13).$$

The unitless albedo factor a is defined as $$a = \frac{\mu_a(\lambda_j)}{\mu_t(\lambda_j)}, \quad (14)$$

and the probability of scattering in such a medium is expressed as $$p(\phi) = a\frac{1-g^2}{(1+g^2-2g\cos(\phi))^{3/2}} = a\sum_{q=0}^{\infty}(2q+1)g^q P_q(\cos(\phi)). \quad (15)$$

Anisotropy of light scattering in an absorbing medium is accounted for by introducing the reduced scattering coefficient $$\mu'_s(\lambda_j) = \mu_s(\lambda_j)(1-g) \quad (16)$$

and the reduced total coefficient of interaction $$\mu'_t(\lambda_j) = \mu_a(\lambda_j) + \mu'_s(\lambda_j) \quad (17).$$

It is conventionally recognized that, as g≥0, the likelihood of forward scattering increases, thereby decreasing the apparent attenuation of light along the path of travel. This conventional view does not take into account the information about a path that an individual photon of light has taken to reach a given point and only accounts for the total flux of light, i.e., $\langle\delta\rangle \neq \delta$. Such a conventional approach, therefore, causes errors in the estimates of concentration. In particular, as $\langle\delta\rangle \gg \delta$, the concentration will be overestimated. Accordingly, the path length $\delta$ may be multiplied by a scalar constant to account for scattering and for the effective path of light $\langle\delta\rangle$ that is not accounted for by the geometrical path of light $\delta$.

Scattering medium often defines the so-called diffusion regime where it is assumed that a steady-state fluence rate, $\Phi$, of light propagating away from a continuous-wave isotropic point light source of wavelength $\lambda_j$ can be modeled as a function of radius, $\Phi(r)$, in an infinite medium using the generic diffusion equation in which the effective attenuation coefficient, is defined for the diffusion approximation:

$$\Phi(r) = \frac{3\mu'_s(\lambda_j)}{4\pi r}\exp(\mu_{eff}(\lambda_j)r). \quad (18)$$

Given these differences between the conventional model and the approach proposed here, it can be seen that information about the path length for an EM wave taken between transmitter and receiver is beneficial toward improving the accuracy of the derived properties measurements.

Oximetry: Considerations

The major chromophores of a blood sample include the functional hemoglobins oxyhemoglobin ($O_2$Hb) and deoxyhemoglobin (Hb), as well as the dysfunctional hemoglobins (i.e., dyshemoglobins or nonfunctional hemoglobins), carboxyhemoglobin (COHb), methemoglobin (MetHb), Glycosylated hemoglobin (GHb/Hb $A_{1c}$) and sulfhemoglobin (SulfHb). The total concentration of [Hb] is represented by [tHb], which is the summation of all the fractions according to $$[tHb] = [O_2Hb] + [Hb] + [COHb] + [MetHb] + [SulfHb] \quad (21).$$

The summation of functional hemoglobin is given by $$[pHb] = [O_2Hb] + [Hb] \quad (22).$$

The oxygen saturation is determined as $$S_{O_2} = \frac{[O_2Hb]}{[pHb]}, \quad (23)$$

and the oxyhemoglobin fraction is determined as $$F_{O_2Hb} = \frac{[O_2Hb]}{[tHb]}. \quad (24)$$

Two-Wavelength Isosbestic Oximetry

If it is assumed that $O_2$Hb and Hb are the only two functional hemoglobin species present in significant concentrations, then only two wavelengths are required to estimate $S_{O2}$. The two wavelengths $\lambda_1$ and $\lambda_2$ can be chosen such that for $\lambda_1$ the corresponding $\epsilon (\lambda_1, O_2Hb)$ is maximally different from $\epsilon (\lambda_1, Hb)$, and such that $\lambda_2$ is an isosbestic point, i.e. that $\epsilon (\lambda_2, O_2Hb)$ exactly equals $\epsilon(\lambda_2, Hb)$. With that, the system of two linear equations requiring a solution is $$\begin{bmatrix} A(\lambda_1) \\ A(\lambda_2) \end{bmatrix} = \begin{bmatrix} \epsilon(\lambda_1, O_2Hb) & \epsilon(\lambda_1, Hb) \\ \epsilon(\lambda_2, O_2Hb) & \epsilon(\lambda_2, Hb) \end{bmatrix} \begin{bmatrix} [O_2Hb] \\ [Hb] \end{bmatrix} [\delta^{BM}]. \quad (25)$$

It is assumed that the extinction coefficients are known and the attenuation (optical density) values have been determined empirically. Accordingly, the ratio of the optical density values at the two chosen wavelengths is $$\frac{A(\lambda_1)}{A(\lambda_2)} = \frac{\epsilon(\lambda_1, O_2Hb)[O_2Hb] - \epsilon(\lambda_1, Hb)[O_2Hb] + \epsilon(\lambda_1, Hb)[pHb]}{\epsilon(\lambda_2, O_2Hb)[pHb]}, \quad (26)$$

and the oxygen saturation ratio is determined, therefore, from $$S_{O_2} = \frac{[O_2Hb]}{[pHb]} = \frac{\frac{A(\lambda_1)}{A(\lambda_2)}\epsilon(\lambda_2, O_2Hb) - \epsilon(\lambda_1, Hb)}{\epsilon(\lambda_1, O_2Hb) - \epsilon(\lambda_1, Hb)}. \quad (27)$$

Generalized Two-Wavelength Oximetry

The derivations provided above demonstrate a solution of the system of equations when an isosbestic point is chosen for one of the $\lambda$'s. Generally, one of the primary reasons behind using an isosbestic point is the simplification of such a solution to one that does not require a large amount of computational effort. Generally, however, if the above linear equations (25) are simply viewed as an unmixing matrix of two superimposed signals with known, unique mixing coefficients $\epsilon$, any $\lambda_1$ and $\lambda_2$ can be selected to estimate the oxygen saturation value—not necessarily the isosbestic wavelength points. Indeed, for two independent wavelengths $\lambda_1$ and $\lambda_2$ (or two non-overlapping spectral bandwidths respectively centered at $\lambda_1$ and $\lambda_2$), the Eq. (7) can be re-written as $$\begin{bmatrix} A(\lambda_1) \\ A(\lambda_2) \end{bmatrix} = \begin{bmatrix} 1.0 & 0.0 \\ 0.0 & 1.0 \end{bmatrix} \begin{bmatrix} [O_2Hb] \\ [Hb] \end{bmatrix} [\delta^{BM}]. \quad (28)$$

In this case, the coefficient matrix defines mixing $\in$ factors that are mutually orthogonal and unitary. The corresponding noise amplification and propagation of variance are given as:

For noise amplification:

$$[g(\lambda_1), g(\lambda_2)] = \text{diag}[(\in^H \Psi^{-1} \in)^{-1}](\text{diag}[\in^H \Psi \in]) \quad (29a),$$

and $$[g(\lambda_1), g(\lambda_2)] = [1,1] \quad (29b).$$

For propagation of variance:

$$[\sigma(\lambda_1), \sigma(\lambda_2)] = \sqrt{\Sigma[(\in^H \in)^{-1}(\in^H)\text{var}(\text{Noise})]} \quad (30a),$$

and $$[\sigma(\lambda_1), \sigma(\lambda_2)] = [1,1] \quad (30b).$$

In contradistinction, for two spectral bandwidths that do overlap a figure of merit needs to be defined, which takes into account such spectral mixing/overlap, in order to optimally select $\lambda_1$ and $\lambda_2$ and amplitude. According to an embodiment of the invention, the choice of two wavelengths for a spectrally overlapping case includes the determination of noise amplification and/or propagation of variance techniques. For example, with numerical coefficients chosen that are not linearly independent and therefore have a condition number greater than one and that result in mixing of the information, the solution becomes more complicated because $A(\lambda_1)$ now comprises signal components from $O_2Hb$ and $Hb$. Similarly $A(\lambda_2)$ now includes signal components from $O_2Hb$ and $Hb$; whereas $A(\lambda_1)$ should contain signal components solely from $O_2Hb$, and $A(\lambda_2)$ should contain signal components solely from $Hb$. This contaminated or impure situation is thereby described as a mixing matrix or non-diagonal matrix. In the case of spectrally overlapping bandwidths corresponding to $$\begin{bmatrix} A(\lambda_1) \\ A(\lambda_2) \end{bmatrix} = \begin{bmatrix} 0.5 & 0.03 \\ 0.2 & 0.4 \end{bmatrix} \begin{bmatrix} [O_2Hb] \\ [Hb] \end{bmatrix} [\delta^{BM}], \quad (31)$$

the noise amplification is observed to increase as the mixing vectors become less orthogonal.

The propagation of variance equation should now account for the decreased orthogonality of the mixing vectors and the decreased $\epsilon$-sensitivity, not otherwise predicted with noise amplification. In the propagation of variance, any decrease in $\epsilon$ sensitivity causes an independent decrease in SNR, because there is less interaction between light and the analyte for a given source-to-detector distance associated with the data acquired at each wavelength. However, $\epsilon$, the interaction penalty, is not observed with noise amplification, and is a very important distinction between the two techniques. Because of this difference, noise amplification is the less preferred technique compared to the propagation of variance technique.

Here, for the above example, the interaction is demonstrated:

For noise amplification:

$$[g(\lambda_1), g(\lambda_2)] = \text{diag}[(\in^H \Psi^{-1} \in)^{-1}](\text{diag}[\in^H \Psi \in]) \quad (32a)$$

and $$[g(\lambda_1), g(\lambda_2)] = [1.1135, 1.1135] \quad (32b).$$

For propagation of variance:

$$[\sigma(\lambda_1), \sigma(\lambda_2)] = \sqrt{\Sigma[(\in^H \in)^{-1}(\in^H)\text{var}(\text{Noise})]} \quad (33a),$$

and $$[\sigma(\lambda_1), \sigma(\lambda_2)] = [2.0676, 2.7759] \quad (33b).$$

The above formulations do not account for the absolute wavelength-dependent c sensitivity and therefore a more general form of noise amplification and propagation of variance parameter may be needed; one skilled in the art can understand the additional constraints that apply for analytes. Unlike the noise amplification approach, the use of the propagation of variance technique for estimation of the oxygen saturation level $S_{O_2}$ depends on both the orthogonality of the c sensitivities and the relative sensitivity of $\epsilon$ at each of the wavelengths. The optimal solution occurs when the signals are substantially not mixed spectrally (which corresponds to equation (28)), resulting in two independent equations and the relative $\epsilon$ sensitivities, each of which is equal to 1. This is important because noise amplification and propagation of variance techniques provide an unbiased estimate of the optimal $\lambda j$'s that should be selected for a given set of chromophores in the experiment. One skilled in the art will observe that both of these approaches may be further adapted to the specific application.

Multiwavelength Oximetry

According to embodiments of the invention, the above-discussed methods are further extended to a case of multi-wavelength oximetry (employing more than two operating wavelengths). Another approach may include a full-matrix solution of the equation such as equation (7) by analogy with that discussed in reference to equations (31, 32a, 32b, 33a, and 33b). It is appreciated that, with the increase of the number of operational wavelengths, the overall variance is increased as well. In the example shown below, five operational wavelengths through are used for determination of only two species (oxyhemoglobin and deoxyhemoglobin):

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} 0.5 & 0.03 \\ 0.2 & 0.4 \\ 0.01 & 0.03 \\ 0.18 & 0.23 \\ 0.21 & 0.13 \end{bmatrix} \begin{bmatrix} [O_2Hb] \\ [Hb] \end{bmatrix} [\delta^{BM}]. \quad (34)$$

In this example, accordingly, for noise amplification:

$$[g(\lambda_1), g(\lambda_2)] = \text{diag}[(\in^H \Psi^{-1} \in)^{-1}](\text{diag}[\in^H \Psi \in]) \quad (35a)$$

and $$[g(\lambda_1), g(\lambda_2)] = [1.2155, 1.2155] \quad (35b).$$

For propagation of variance:

$$[\sigma(\lambda_1), \sigma(\lambda_2)] = \sqrt{\Sigma[(\in^H \in)^{-1}(\in^H)\text{var}(\text{Noise})]} \quad (36a)$$

and $$[\sigma(\lambda_1), \sigma(\lambda_2)] = [1.8787, 2.5257] \quad (36b).$$

It is important that the wavelengths selected in multi-wavelength oximetry be optimized to improve the orthogonality and analyte sensitivity of the mixing equation. Mere addition of supplementary wavelengths can have the effect of decreasing the SNR in the resulting estimate of $S_{O_2}$. Further, according to the invention, selection of additional (supplementary) wavelengths is made dependent on the number of chromophores (elements of blood) to be measured. Specifically, the multiple wavelengths selected for determination of two chromophores (such as $O_2Hb$ and Hb, for example) may be different from the same number of multiple wavelengths selected for a five-chromophore oximetry measurement. The result of selecting multiple wavelengths according to the idea of the invention allows for the detection of dyshemoglobins, for example, and for improved sensitivity of the pulse oximeter or spectrometer device without adversely affecting the noise figure in the estimates of concentration of the functional hemoglobins. In one specific example:

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} \epsilon(\lambda_1, C_1) \\ \epsilon(\lambda_2, C_2) \\ \epsilon(\lambda_3, C_3) \\ \epsilon(\lambda_4, C_4) \\ \epsilon(\lambda_5, C_5) \end{bmatrix} \begin{bmatrix} [O_2Hb] \\ [Hb] \\ [COHb] \\ [MetHb] \\ [rHb] \end{bmatrix} \begin{bmatrix} \delta^{C_1} \\ \delta^{C_2} \\ \delta^{C_3} \\ \delta^{C_4} \\ \delta^{C_5} \end{bmatrix} \quad (37a)$$

where equation 37a is derived from equation 7 for the specific example using five exemplary material components ($O_2Hb$, Hb, COHb, MetHb, and rHb) of interest. Exemplary extinction coefficients are provided yielding:

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} 0.5 & 0.03 & 0.01 & 0.01 & 0.01 \\ 0.2 & 0.4 & 0.01 & 0.01 & 0.01 \\ 0.01 & 0.03 & 0.40 & 0.07 & 0.01 \\ 0.18 & 0.23 & 0.01 & 0.60 & 0.01 \\ 0.21 & 0.13 & 0.01 & 0.07 & 0.40 \end{bmatrix} \begin{bmatrix} [O_2Hb] \\ [Hb] \\ [COHb] \\ [MetHb] \\ [rHb] \end{bmatrix} [\delta^{BM}], \quad (37b)$$

Similarly, as shown in equation 9, it is also desirable to be able to derive the concentration of the material components of interest given attenuations for each waveform transmitted. Using matrix operations on equation 37a, it is shown that the concentrations of each material component can be derived from the molar extinction coefficients $\epsilon(\lambda_i, C_i)$, attenuations $A(\lambda_i)$ of the waveforms, and the traversed distances $\delta^{Ci}$. This form of the equation is shown in equation 37c for using the distance associated with bulk media.

$$\begin{bmatrix} \epsilon(\lambda_1, C_1) \\ \epsilon(\lambda_2, C_2) \\ \epsilon(\lambda_3, C_3) \\ \epsilon(\lambda_4, C_4) \\ \epsilon(\lambda_5, C_5) \end{bmatrix} \begin{bmatrix} A(\lambda_1) \\ A(\lambda_2) \\ A(\lambda_3) \\ A(\lambda_4) \\ A(\lambda_5) \end{bmatrix} [\delta^{BM}]^{-1} = \begin{bmatrix} [O_2Hb] \\ [Hb] \\ [COHb] \\ [MetHb] \\ [rHb] \end{bmatrix}, \quad (37c)$$

equation 37d shows the same equation (37c) using the inverted exemplary extinction coefficients shown previously in equation 37b.

$$\begin{bmatrix} 2.08 & -0.12 & -0.05 & -0.02 & -0.05 \\ -1.02 & 2.60 & -0.04 & -0.02 & -0.04 \\ 0.11 & -0.08 & 2.51 & -0.29 & -0.06 \\ -0.22 & -0.95 & -0.01 & 1.69 & -0.01 \\ -0.72 & -0.61 & -0.02 & 0.27 & 2.54 \end{bmatrix} \begin{bmatrix} A(\lambda_1) \\ A(\lambda_2) \\ A(\lambda_3) \\ A(\lambda_4) \\ A(\lambda_5) \end{bmatrix} [\delta^{BM}]^{-1} = \quad (37d)$$

$$\begin{bmatrix} [O_2Hb] \\ [Hb] \\ [COHb] \\ [MetHb] \\ [rHb] \end{bmatrix},$$

Referring to equation 37b, noise should also be taken into consideration. For noise amplification:

$$[g(\lambda_1), g(\lambda_2)] = \text{diag}[(\epsilon^H \Psi^{-1} \epsilon)^{-1}](\text{diag}[\epsilon^H \Psi \epsilon]) \quad (38a),$$

and $$[g(\lambda_1), g(\lambda_2)] = [1.3546, 1.3440] \quad (38b).$$

For propagation of variance:

$$[\sigma(\lambda_1), \sigma(\lambda_2)] = \sqrt{\Sigma[(\epsilon^H \epsilon)^{-1}(\epsilon^H) \text{var}(\text{Noise})]} \quad (39a)$$

and $$[\sigma(\lambda_1), \sigma(\lambda_2)] = [2.0936, 2.7927] \quad (39b).$$

Weight Function or Parameter

It is appreciated that, given the derivation of equation (7), additional wavelength-specific penalties or weighting factors can be incorporated via a two-dimensional (2D) or vector (1D) matrix W representing a cost-function that incorporates, for example, noise penalties. When the spectral channels of the oximeter (i.e., the operational wavelengths and associated spectral bandwidths) are independent (non-overlapping), W is the identity matrix $W_I$. Alternatively the $W=W_{sep}$ matrix can include penalties associated with the wavelength separation (which relates the separation to the increased difference in δ or the differential path length factor ⟨ δ⟩ as the operational wavelengths are spaced further apart). In yet another implementation, an alternative or additional $W=W_{cost}$ weighting matrix can include penalties for the complexity or cost of manufacture of the source of light operating at a particular wavelength. Further, all or at least some of such weighting factors can be used in series to make the optimization of wavelength selection more practical. Accordingly, to incorporate a weighting function, the general matrix equation (7) can be re-written, for example, from $$[g(\lambda_1)W(\lambda_1), g(\lambda_2)W(\lambda_2)] \text{ and } [\sigma(\lambda_1)W(\lambda_1), \sigma(\lambda_2)W(\lambda_2)] \quad (40a),$$

to, $$[g(\lambda_1)W_I W_{cost}(\lambda_1), g(\lambda_2)W_I W_{cost}(\lambda_2)] \quad (40b)$$

and $$[\sigma(\lambda_1)W_I W_{cost}(\lambda_1), \sigma(\lambda_2)W_I W_{cost}(\lambda_2)] \quad (40c).$$

Pulse Oximetry

According to one implementation of the invention, the oximetry data processing method that takes into account the "pulse" nature of the pulse oximetry data-acquisition (such as, for example, (i) the presence and/or parameters of the arterial pulse wave and (ii) the temporal point-spread function or impulse response associated with the tissue being measured, including the time-ordered sampling of the effect of the transfer function of the tissue on light passing through the object) determines the temporal dependence of light attenuation by the tissue. For example, in the case when the two chosen operational wavelengths/bandwidths do not overlap, the equation (7) may expanded to explicitly include the tissue and venous component factors:

$$\begin{bmatrix} A(\lambda_1, t) \\ A(\lambda_2, t) \end{bmatrix} = \begin{bmatrix} \epsilon(\lambda_1, O_2Hb) & \epsilon(\lambda_1, Hb) & \epsilon(\lambda_2, \text{tissue}) \\ \epsilon(\lambda_2, O_2Hb) & \epsilon(\lambda_2, Hb) & \epsilon(\lambda_2, \text{tissue}) \end{bmatrix} \begin{bmatrix} [O_2Hb(t)] \\ [Hb(t)] \\ [\text{tissue}(t)] \end{bmatrix} \quad (41)$$

$$\begin{bmatrix} \delta^{O_2Hb}(t) \\ \delta^{Hb}(t) \\ \delta^{\text{tissue}}(t) \end{bmatrix}.$$

In this example, and further considering the time-derivative of the equation (41) expressed as $$\frac{d[A(t)]}{dt} = \frac{d}{dt}\begin{bmatrix} A(\lambda_1, t) \\ A(\lambda_2, t) \end{bmatrix}, \quad (42)$$

the following assumptions are made:
(i) for a given chromophore, a portion of the absorption spectrum (of such a chromophore) that remains unchanged with time is set to zero by the above time derivative;
(ii) the effective distance traveled by light is substantially the same for all chromophores and equals $\Delta\langle\delta\rangle$, or the change in distance caused by the arterial pulse, and
(iii) only two chromophores are being considered (which is an optional assumption specific only to this example).

The cancellation of the change in path length due to the arterial pulse-wave from the equation is achieved by, for example, defining a ratio of the equations (39) corresponding to two different wavelengths:

$$\frac{R_{\lambda_1}}{R_{\lambda_2}} = \frac{\frac{d[A(\lambda_1, t)]}{dt}}{\frac{d[A(\lambda_2, t)]}{dt}} = \frac{\epsilon(\lambda_1, O_2Hb)\Delta[O_2Hb] + \epsilon(\lambda_1, Hb)e[Hb]\,\Delta(\delta)}{\epsilon(\lambda_2, O_2Hb)\Delta[O_2Hb] + \epsilon(\lambda_2, Hb)e[Hb]\,\Delta(\delta)}, \quad (43a)$$

$$\Delta[pHb] = \Delta[O_2Hb] + \Delta[Hb]\Delta[pHb] = \Delta[O_2Hb] + \Delta[Hb]. \quad (43b)$$

The solution for the oxygen saturation level for pulse oximetry can be determined under these assumptions as $$S_{p,O_2} = \frac{\Delta[O_2Hb]}{\Delta[pHb]} = \frac{\frac{R_{\lambda_1}}{R_{\lambda_2}}\epsilon(\lambda_2, Hb) - \epsilon(\lambda_1, Hb)}{\epsilon(\lambda_1, O_2Hb) - \epsilon(\lambda_1, Hb) + \frac{R_{\lambda_1}}{R_{\lambda_2}}(\epsilon(\lambda_2, Hb) - \epsilon(\lambda_2, O_2Hb))}. \quad (44)$$

Given the similarity between the pulse oximetry solution (44) and the standard oximetry solution (27), one skilled in the art can appreciate that it is feasible that a wavelength selected to be optimal for standard oximetry may also be optimal for pulse oximetry.

Qualitative and Quantitative Pulse Oximetry

The major differences between qualitative pulse oximetry and quantitative oximetry are: A) pulse oximetry measures the ratio of oxyhemoglobin to deoxyhemoglobin by first assuming that the ratio of the wavelength-specific optical path lengths is unity, or alternately that a ratio factor is well known, thus removing unknown variables from the system of equations; B) pulse oximetry assumes that the wavelength-specific time-varying arterial pulse measured by the pulse oximeter is caused by increased path length of light through the arteries; C) pulse oximetry assumes that the ratio of time-varying signals at different wavelengths is related linearly, or by a low-order polynomial, to invasive blood gas measurements (i.e., by medical laboratory measurement of the oxygen saturation of a sample of blood drawn from the patient) to calibrate the device to percent saturation or to the ratio of oxyhemoglobin to the combined amount of oxyhemoglobin and deoxyhemoglobin [i.e., oxyhemoglobin/(oxyhemoglobin+deoxyhemoglobin)]; D) pulse oximetry relies on the invalid Beer-Lambert law; E) quantitative oximetry assumes that light diffuses down a concentration gradient from a source, rather than the Beer-Lambert law's known-incorrect assumption of a direct optical path without scattering between the optical source and the photo detector; F) quantitative oximetry attempts to account for the scatter in tissue which alters the optical path length from the geometric, or shortest path length assumed by the Beer-Lambert law, to the average path length which is greater than the geometric path; and G) quantitative oximetry does not rely on the arterial pulse and instead measures the absorption at specific wavelengths that directly relate to the concentration of oxyhemoglobin and deoxyhemoglobin.

In tissue, the path that light follows from the source to the detector is not directly along the minimal geometric path. Instead, the light is highly scattered, resulting in a net path length longer than the geometric path length. In addition, the net path length is wavelength specific. In algorithms of the related art, see for example, Ayogi et al (Int'l Anesthesia Res. Soc., v. 105, No. 6, December 2007), the optical path length factors for the wavelengths are assumed to be similar, allowing them to be divided out. In addition, the differential path length factor is specific to anatomy, e.g. finger versus the scalp or pinnae of the ear, while normal anatomical variation, e.g. finger thickness, makes the differential path length factor highly inaccurate. In reality requiring the path length to be the same for all wavelengths and for the placement on patients and anatomy of patients to be exactly the same is unlikely; therefore, measuring the actual optical path length for each wavelength is advantageous.

Examples of Algorithms for Solving Matrix Equations
Simulated Annealing

In one implementation, the technique referred to as simulated annealing is used to determine the optimum selection of wavelengths. Simulated annealing (SA) is a general meta-heuristic for locating a good approximation to the global optimum of a given function in a large search space. For the wavelength choice task, simulated annealing is more tractable than exhaustive enumeration. The name of the method comes from annealing in metallurgy, a technique involving heating and controlled cooling of a material to increase the size of its crystals and reduce their defects; both are attributes of the material that depend on its thermodynamic free energy. Heating and cooling the material affects both the temperature and the thermodynamic free energy. As illustrated in the flow diagram of FIG. 5, in this solution space, temperature is an analog for both the probable range of change selected in 'permute the solution' 510 between successive explorations of the solution space, and the likelihood P that that a "worse" solution will be chosen at 'evaluate choice' $P(E_{OLD}, E_{NEW}, \text{Temp})$ 515. The analog for the thermodynamic free energy of metallurgy is the figure of merit $E_{WAVESET}$ used to evaluate the choice of wavelengths. Cooling is implemented in the Simulated Annealing algorithm as a slow decrease in the probability of accepting worse solutions as the algorithm explores the solution space. Accepting worse solutions is a fundamental property of this heuristic because it avoids the traps of locally optimal solutions that are worse than the global optimum.

Figure 5:
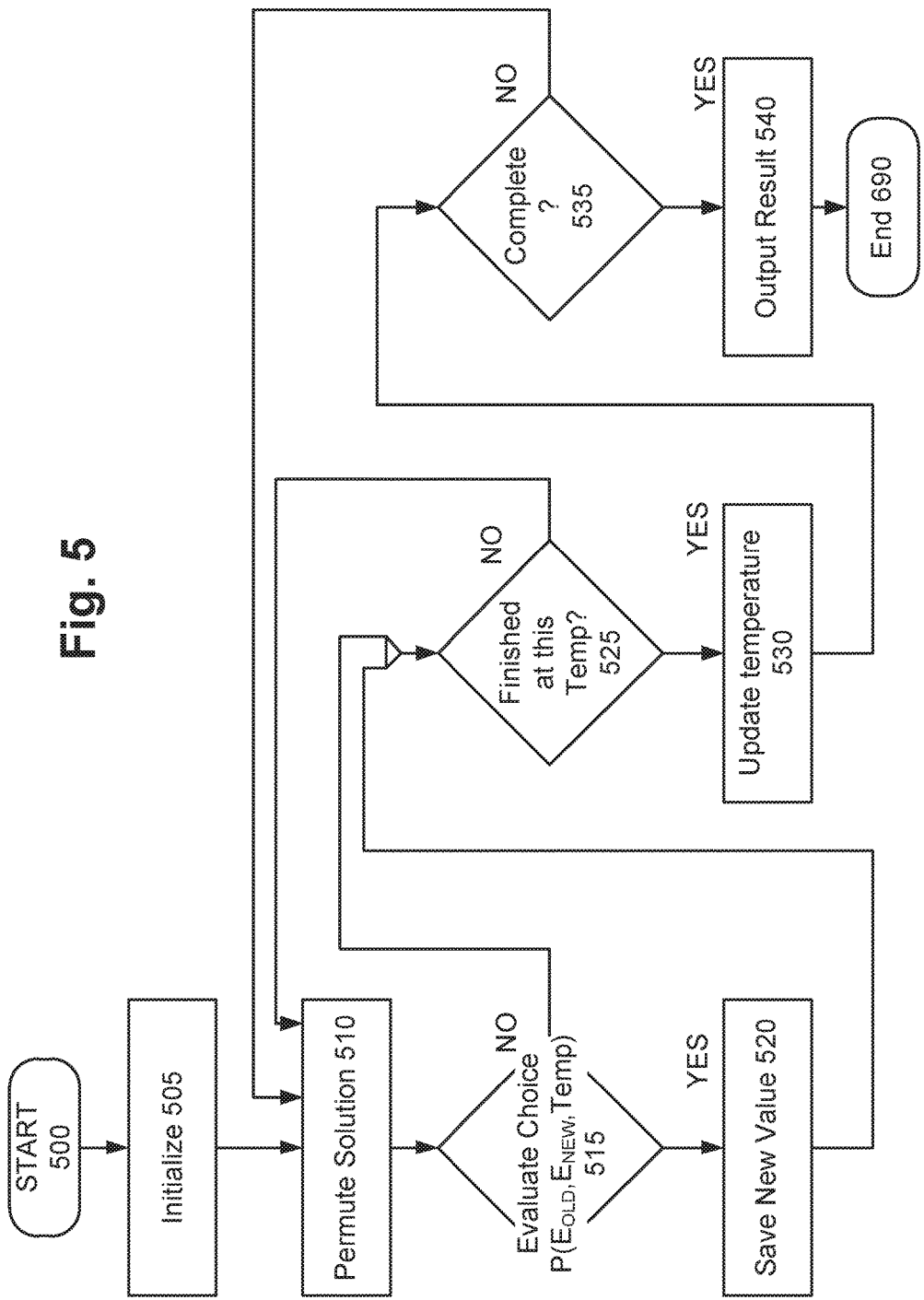
FIG. 5 is a flow chart illustrating an optimization algorithm defining a simulated annealing solution.

With reference to FIG. 5, a simulated annealing optimization algorithm initializes various data structures 505, including a starting point for the solution (selection of wavelengths), the equation to calculate the worthiness of the solution $E_{WAVESET}$, the present value of the goodness $E_{OLD}$ (Referred to here as the energy of the solution, where energy is desired to be minimized), and a setting of the current "temperature" (Temp). Additional initialization may take place without loss of generality. The chosen solution is permuted (the selection of wavelengths is updated) at random from the possible solutions. The range of permutations is governed by the use of the "temperature" of the computation, said "temperature" to be reduced over the course of successive runs such that the range of possible solutions to be examined is updated in a stepwise fashion (for example, decreased) over time, as discussed below. As each permuted solution is evaluated, 515, if the objective function, $E_{WAVESET}$, yields a better number (which occurs if the "energy" of the permuted solution state is less than the previous state), then with probability $P(E_{OLD}, E_{NEW}, Temp)$ the present state is updated to reflect the permuted state, step 520. Proceeding from this step, the evaluation to determine if permutations at this energy level have completed is performed. A number of techniques may be used for this evaluation, including but not limited to a count associated with a particular "temperature" step, or an evaluation of change over the last selected number of evaluation runs. If there are no more perturbations to be performed at this "temperature," the "temperature" is updated 530. If there are no more "temperature" selections to be performed, i.e., if the computation is complete 535, then the result is returned 540 and the algorithm finishes 545. If the evaluation 535 so determines, computation will continue at 510, producing an additional permutation at the new "temperature."

The properties of 'evaluate choice' $P(E_{OLD}, E_{NEW}, Temp)$ 515 are such that as the temperature (Temp) decreases, the likelihood of the lower of $E_{OLD}$ and $E_{NEW}$ will be chosen. As described above the objective function, $E_{WAVESET}(\lambda_1, \ldots, \lambda_N)$ is based on the wavelengths selected $(\lambda_1, \ldots, \lambda_N)$. Processing the wavelength choices through the spectrometric graphs determines the conversion matrix to be used from received signal to material composition. The matrix thus formed is evaluated for propagation of variance, and this result is weighted by the various cost functions related to the chosen wavelengths and the relation between the wavelengths. This operation produces the figure of merit for the particular choice of wavelengths. See Equations 40a-40c.

Figure 6:
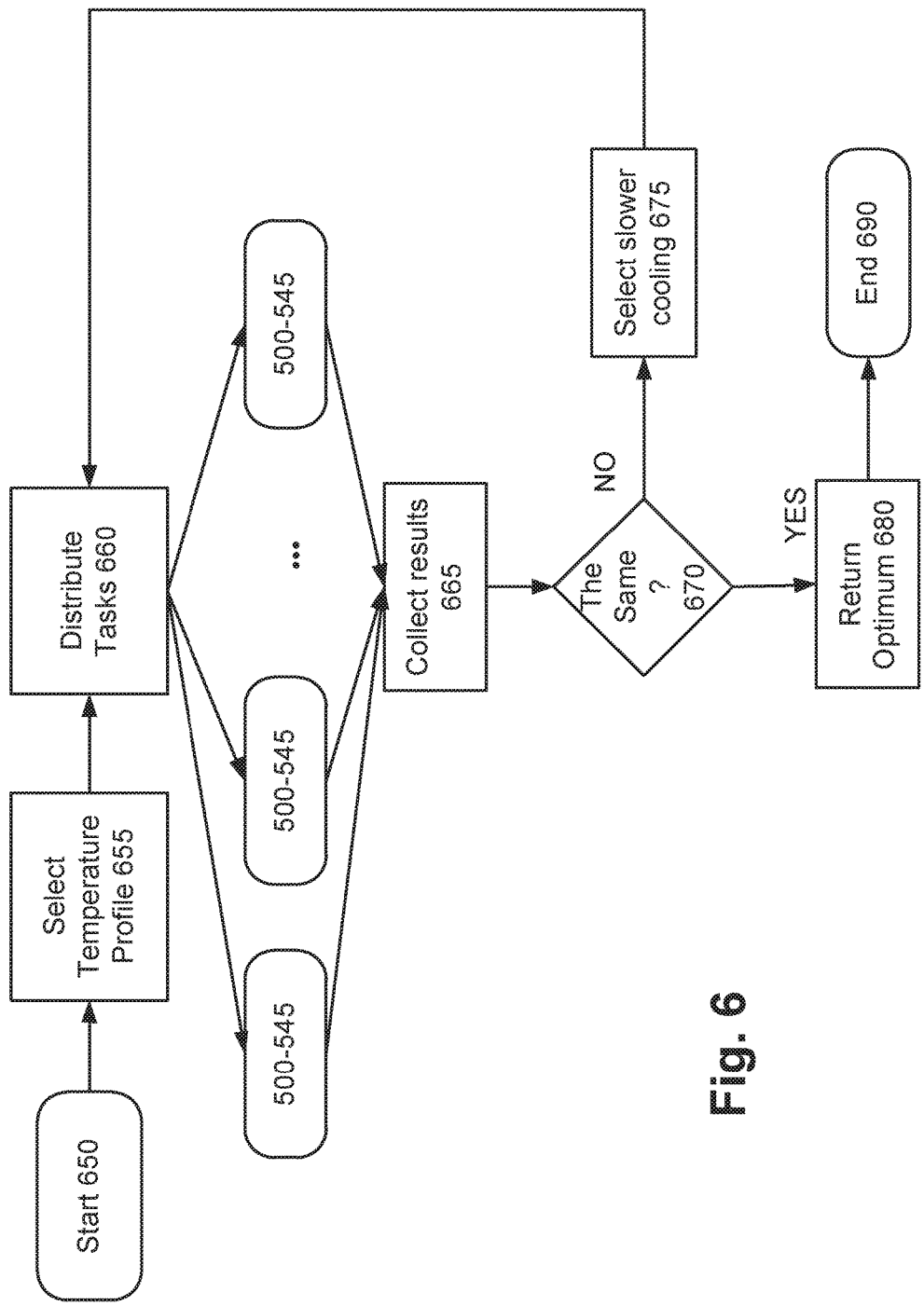
FIG. 6 is a flow chart illustrating a sequence of validation of a simulated annealing solution to the optimization algorithm incorporating the sequence of steps illustrated in FIG. 5.

With reference to FIG. 6, it is advantageous to verify that the state chosen by the simulated annealing at step 545 is the optimal choice. It has been found that the confidence in the optimality of the chosen state can be increased by performing multiple trials of the sequence illustrated in FIG. 5 (steps 500-545). The validation of the simulated annealing solution includes choosing a "temperature cooling" profile at step 655 and running multiple tasks for this "temperature profile." These tasks are distributed in step 660 and the results are collected at step 665. If results collected based on multiple runs are substantially the same, as determined at step 670, then the confidence is high that the optimal choice has been returned, 680, and the algorithm ends at step 690. If the results from multiple runs differ, based on comparison carried out at step 670, then "select slower cooling" 675 engages a slower cooling profile than had been used previously at "Distribute Tasks" 660. The operation of evaluating the tasks described in reference to steps 660-670 is repeated until the cohort of solutions converges based on comparison performed at step 670.

The choice of wavelength(s) and the weighting functions (or constraint parameters) representing partial or full operational cost of employing the device and used in the evaluation may include finite or discrete variables and continuous variables. The random perturbation of the wavelengths in the solution state can be augmented by a number of techniques, including those known in the art but not limited to gradient decent (i.e., if a change improved the result last time, make a further change in the same direction) and statistical sampling.

Additional Algorithms

Convex optimization, as described by Stephen Boyd and Lieven Vandenberghe, (in *Convex Optimization*, Cambridge University Press; Mar. 8, 2004) and linear programming as described by R. Fletcher (in *Practical Methods of Optimization*, Wiley, 1987) are two additional classes of techniques that can be used to find improved solutions to the quantified problem as stated above.

Structures, Systems, and Methods

A combination of structures, systems, and methods (collectively referred to as techniques herein) can be used to improve accuracy of the measurements in the presence of noise, to increase sensitivity of the measurement system (for example, with respect to the measurement of very small component percentages), to discriminate between different material components, and to provide and improve the ability to discern changes in the material makeup of a measured sample over time and location. The variation in the measurements to be made can come from many sources, and a combination of the techniques is needed to address the combination of the variation sources identified below.

Causes of Measurement Signal Variation and Degradation

Causes of signal variation or degradation of accuracy during a measurement include heterogeneity of the sample, the presence of confounding materials, electronic noise, non-linearity of the electronics and optics, ambient radiation, randomness, which includes variations in signal path, quantization at translation points, quantum effects of very low signal levels, fluorescence within the sample, and non-linear component interaction. Each of these is discussed below, although this list should not be considered exhaustive.

Heterogeneity of the sample. Heterogeneity of the sample being measured causes variations in measurement results depending on the paths taken by radiation through the sample. If the sample is not perfectly homogenous, then the variations in composition can be considered a noise element of the measurement. Spatial localization of the measurements, either mechanically or using fine-grained temporal characterization of the sample response, can be used to limit the noise caused by such inhomogeneity. Averaging the results over numerous measurements partially alleviates this problem, but it is often precise information on the variation over time and space that is useful diagnostically. For this reason, several of the techniques described below are beneficially employed.

Figure 7:
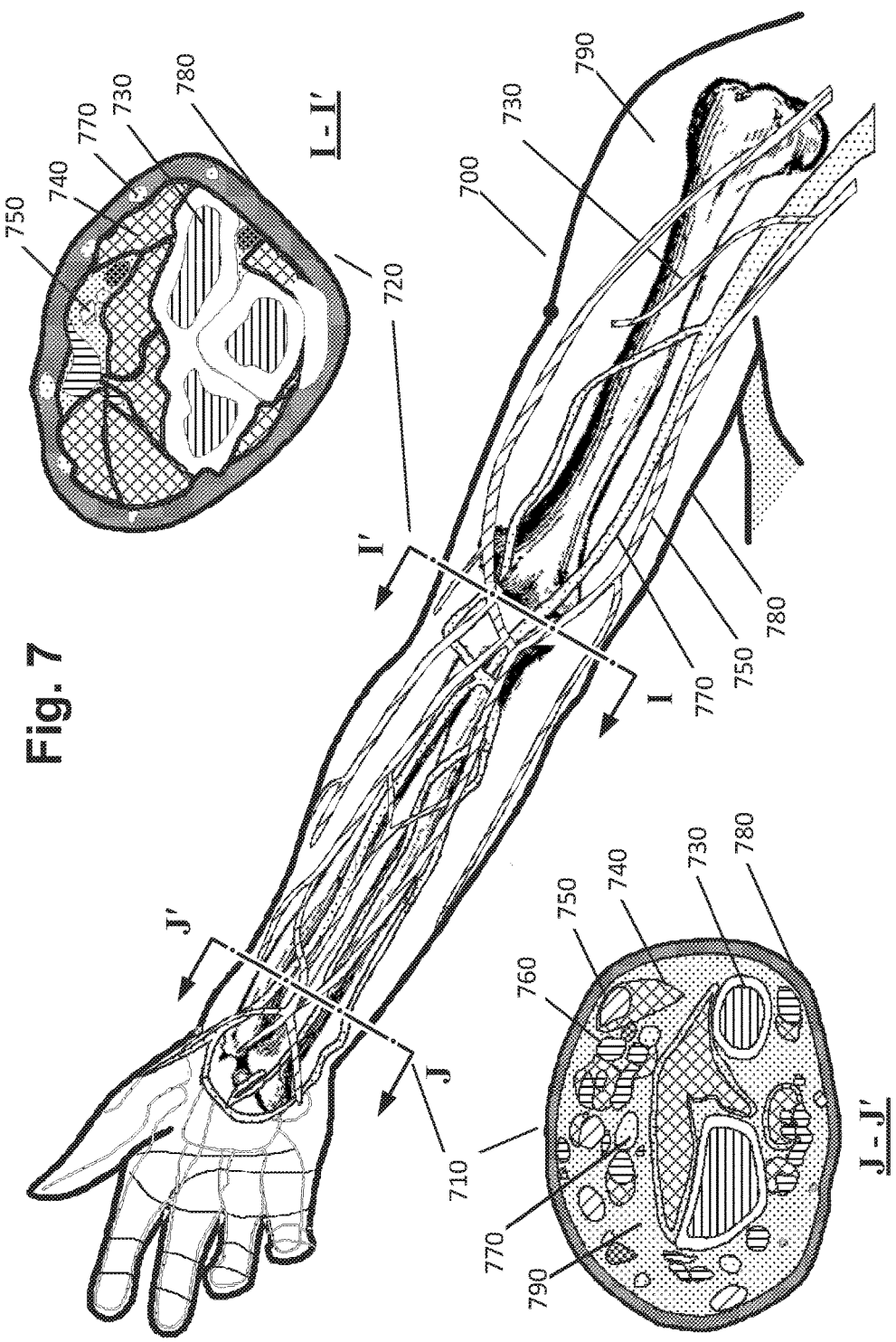
FIG. 7 is a diagram illustrating an arm with two detailed cross-sectional views.

Referring to FIG. 7, an arm 700 is schematically illustrated, with two cross-sectional views 710 (taken along the plane J-J') and 720 (taken along the plane I-I'), where 710 is a notional cross section taken close to the wrist, and 720 is a notional cross section in the vicinity of an elbow. FIG. 7 is intended to illustrate the heterogeneous makeup of the sample used when an embodiment of a spectrometric device according to the invention is juxtaposed with a human. Different parts of the sample will modify the signal differently as it passed through the sample. The bone structure 730 is also shown in the two cross-sectional views 710 and 720. The cross sectional views include muscle tissue 740, not shown in the main view for purposes of clarity. The major vein system 750 and arterial system 770 are schematically illustrated to show the variation of the tissue throughout the sample, and to show that the size of the veins and arteries varies, as does their proximity to each other. For this reason, measurements that are configured to localize the response to the tissue of interest provide a better result. Also pictured in the cross sectional views are notional locations of the tendons.

Confounding materials. While the concentration of particular material components in a tissue sample may be of interest, it will also be important to assess the potential presence of additional components of the sample that may confound the measurements of the material components of interest. A particular confounding component may vary in concentration or distribution. Potentially confounding materials are spectrometrically active, that is, their effects on the propagation of a signal at different wavelengths vary. The description of bilirubin offered in reference to FIG. 3D above provides an example of a potentially confounding material and several appropriate treatments of a potentially confounding material.

Electronic noise. An electronic system, that is designed to operate at temperatures above absolute zero, is subject to generation of thermal noise in each of the system's components. The characteristics of additional types of noise (such as Shot noise or 1/f noise, for example) depend mostly on device type and/or manufacturing quality and semiconductor defects, such as conductance fluctuations. In measurement systems, the noise is an error or undesired random disturbance of a useful information signal, introduced before or after the transmitter, detector, and decoder. The noise is a summation of unwanted or disturbing energy from natural, and sometimes, man-made sources. If noise is caused by a number of uncorrelated sources, the central limit theorem (also known as the "Law of large numbers") states that the noise exhibits a statistically "normal" or Gaussian, distribution. This means that a number of techniques (discussed below) can be used to extract very accurate measurements from below the noise floor. The quality of such extraction is dramatically improved if different causes of noise do not correlate with one another or if they are correlated, they correlate in an identifiable fashion.

Figure 8A:
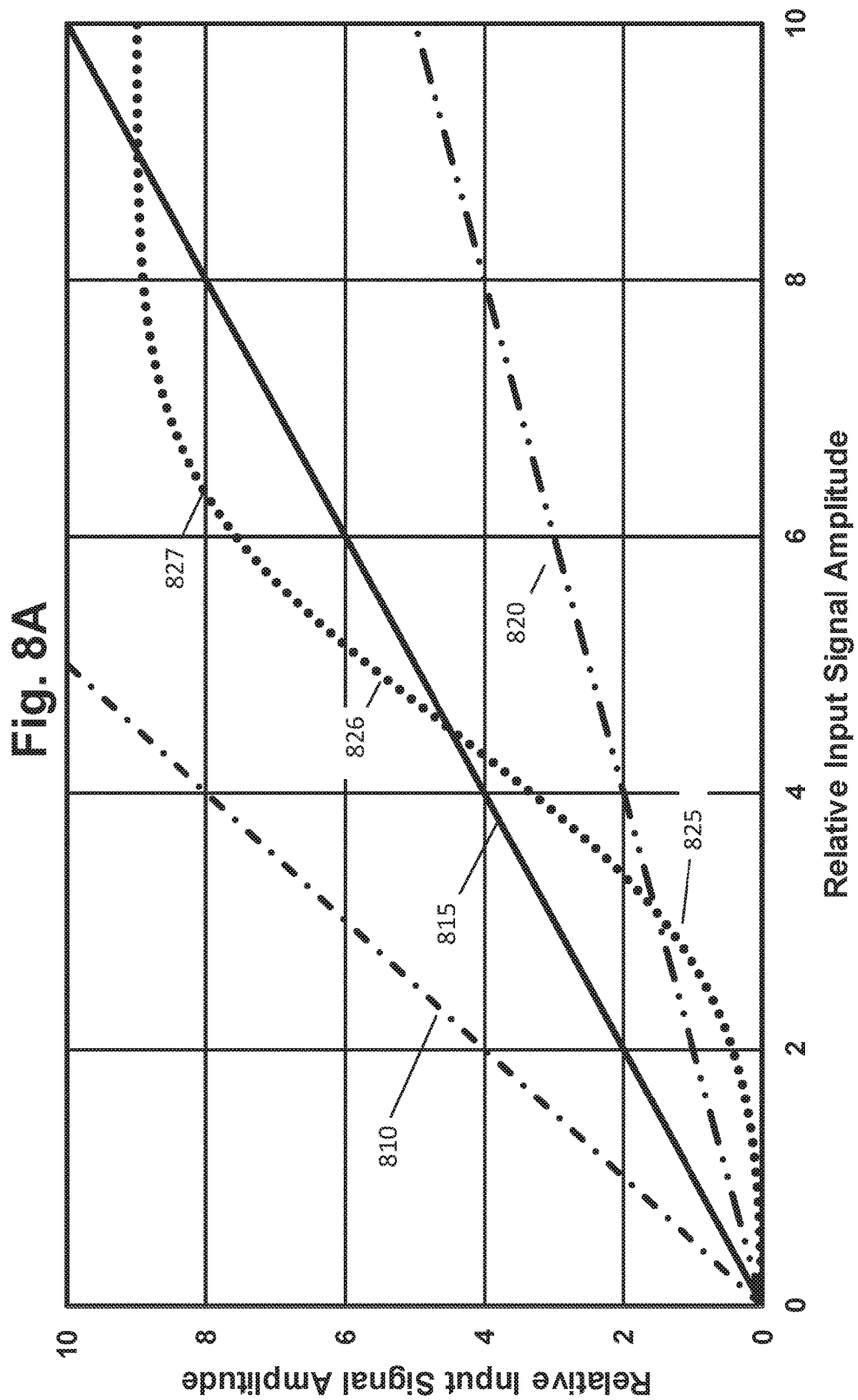
FIG. 8A is a graph illustrating linear and nonlinear transfer functions.

Non-linearity of the electronics and optics. When non-linearities are present in the measurement system, and when different measurements are carried out under different non-linearity conditions, the algorithm based on the matrix approach as discussed above, which is based on linear transformations, may produce erroneous results. Referring to FIG. 8A, in which an input signal level is compared to 4 different system output signal levels, linear signal 810 represents a linear output the value of which is two times its input value. Similarly, linear output 815 shows a one-to-one relationship with the input signal, and linear output 820 shows a one-half input level signal. The non-linear data series has a low but increasing gain region 825, a high gain region 826, and a high output but very low incremental gain region 827.

If the signal from the EMW at one wavelength encounters a stage operating in a regime similar to 825, while the EMW at a second wavelength is operating in a regime similar to 826, the relative differences in signal level at the second wavelength will be exaggerated when compared to that at the first wavelength.

Linearization before combination is important for accurate results. Calibration and compensation circuits can be used as well as calibrated range selection circuits to avoid the inaccuracies that may be caused by the non-linearities of the electronics and the optics.

Ambient radiation. There is often ambient radiation illuminating the samples being measured. Techniques to distinguish the effects of the ambient radiation from the measuring probe must be used. In addition, if the ambient radiation overloads the input of the receiver, this task becomes more difficult.

SNR improvement techniques The signal accuracy improvement techniques include the previously described improved choice of wavelength used for spectrometric measurements. The signal accuracy improvement techniques also include the techniques described below, including, but not limited to pulsing the transmitted radiation, providing variety in the on and off sequences, performing correlation between the transmitted radiation and the received signal from the sample under measurement, repetition of the measurement, using a variety of techniques to localize the portion of the sample being measured, using additional receivers, using the variations in the impulse response produced by a variety of techniques, selecting particular portions of the impulse responses according to algorithms, and using physical structures to modify the path from the transmitter to the sample and from the sample to the receiver.

The design of many communications and measurement systems must take into account the fact that the transmitted signal (in case of communications systems) or measured values (in case of many other systems) may be degraded due to distance propagation, noise in the environment, and many other factors. The "signal" that emerges at the output end of a communication path or at the detector of a measurement system can, however, be improved (that is, the SNR of the detected data can be enhanced) with the use of various statistical processing approaches. The relative strength enhancement of the received signal is referred to as "signal processing gain," or simply "processing gain," and can significantly improve the SNR of the end-to-end system.

In one embodiment, the sequence of "ones" and "zeros" of the excitation sequence is generated by an appropriate hardware component of the system operating according to an algorithm on the transmit-side of the system and, as such, is defined by and/or in the system. On the receive-side of the system, the received signal can be converted into a stream of electrical "ones" and "zeros" and then passed through a "digital cross-correlator," which conceptually moves (i.e., a sliding window relative to time) the ones and zeros past a matching, pre-stored pattern. When the two signal patterns are delivered to the post-processing unit and line up or are found to conform to one another in the post-processing unit, the "digital correlator" responds that it has found a "match" between the transmitted pattern and its pre-stored pattern, and generates a "match signal." The amplitude of the "match signal" is a measure of the "processing gain" from using the correlation approach; in general, the longer the pattern of ones and zeros, the stronger will be the amplitude of the "match signal." If the transmitted pattern is different from the pattern stored in the cross-correlator, no "match" will be reported by the system.

Figure 8B:
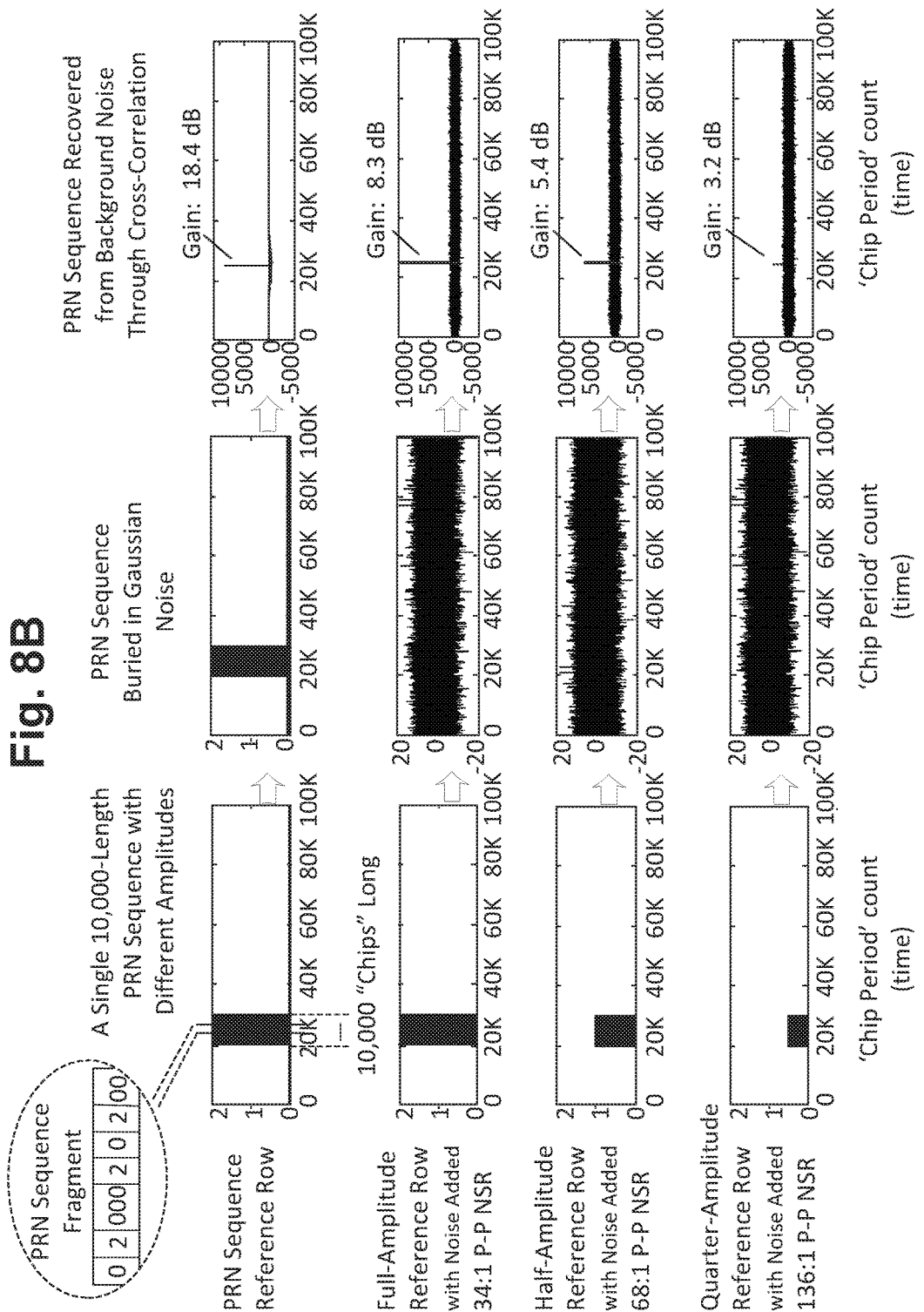
FIG. 8B is a set of graphs illustrating the ability to receive and recover the excitation sequence from additive noise.

The advantage of this approach is that the received signal can be afforded to be substantially below the "noise floor" of the signal path. With reference to FIG. 8B, it can be seen that an extended excitation sequence or signal can be constructed from an edge-rich concatenation of zero-values and two-values such that a sequence with transitions at varying intervals is produced. This excitation sequence can be buried or hidden in noise. With reference to FIG. 8B, the amplitude of the excitation sequence is attenuated such that the noise to signal ratio (NSR) reaches the level of 34:1 on the three graphs of the second row from the top, 68:1 on the graphs of the third row from the top, and 136:1 at the fourth row from the top. The four graphs in the middle column of graphs of FIG. 8B illustrate the burst of the excitation signal added with a zero-mean 4σ Gaussian noise source. The four graphs in the rightmost column show the result of performing a cross correlation of the excitation sequence signal with the noisy signal. The presence of the 10,000-bit excitation sequence signal is recovered from the noise even if the transmitted signal is buried in the background noise, at levels of $\frac{1}{34}$th, $\frac{1}{68}$th, or even $\frac{1}{136}$th of the noise level. The longer the excitation sequence, the higher will be the potential SNR of the recovered signal; a properly chosen 2000-bit excitation sequence will have a higher SNR than a 1000-bit sequence, and so on. Notably, the cross-correlator may optionally yield a measure of elapsed time as well; if there is a reference time "tick," the correlator will indicate not only how strong the recovered signal is, but when the match occurred in time. In the following paragraphs, we describe in more detail how this cross-correlation approach can be employed. For the oximetry application described, where the body-worn oximeter is to be tiny and powered by a small coin cell, the cross-correlator will beneficially be implemented as custom-designed integrated circuit.

With reference to FIG. 8C, a series of graphs of a signal amplitude over time are shown. Graph 885 represents the impulse response of a sample being measured by a spectrometric system. This impulse response is used in the rest of the illustration in FIG. 8C. Graph 886 represents the idealized single chip input pulse to the system. The term "chip time" refers to the duration between opportunities for a discrete time-quantized excitation sequence to change from one level to another. The term "chip" in this context refers to the signal during the time between two successive change opportunities. The horizontal axis of graph 886 has tick marks at chip boundaries. Specifically, because this illustration shows a spectrometric system characterized by chip duration of five time units, the tick marks are numbered at times equal to 0, 5, 10, 15, 20, 25, and 30 and the period in between each tick mark is referred to as a chip. Therefore, a single chip pulse 886 is a signal which has an amplitude at a low level, then at a chip boundary makes a transition to a high amplitude, and at the next chip boundary makes a transition to a low amplitude.

The graphs of FIG. 8C are provided for the purposes of illustration only; amplitudes are normalized where appropriate to a high level of one and a low level of zero. Given the system impulse response 885, the response of the system to a single chip pulse input 886 is represented by the graph 887. This pulse response 887 can be used as a visual reference for the waveforms represented by the graphs below, 890, 894, and 895. An implementation of the invention produces a series of chips in the form of an excitation sequence 888. Notably, the excitation sequence 888 as shown can also be represented by the sequence of binary digits: {1, 0, 0, 0, 0, 0, 1, 1, 0, 1, 1, 0, 1, 0, 1, 0, 0, 0, 0, 1}. Graph 889 represents the response, or the output, of a system with impulse response 885 and excitation sequence (input) 888. This signal is no longer a binary signal, but best thought of as an analog signal, or a continuously varying signal.

There are varieties of circuits and mathematical operations that can be used to take the excitation sequence as a baseline, and find the correlation over a time range of that baseline with the output 889. One such method is to take the dot product of the two signals to provide a correlation value at time offset zero, and the dot product of the output 889 and the excitation sequence 888 time delayed by Δt to find the value for the time Δt. Graph 890 represents the result that is the correlation of the input of the system with the output of the system. The noiseless correlation 890 is substantially identical to the pulse response 887. The graphs 887 and 890 appear different because the single chip pulse used as input to 887 starts at time 5 rather than time 0.

When noise is introduced into a measurement system, the noise becomes part of the output. When measuring the effect of the controlled input to the system, the effect of the noise must be reduced. Several techniques are illustrated in the present disclosure to allow a measurement to be more accurate—even in the presence of noise. Graph 892 represents the excitation sequence 888 on the local scale. Gaussian noise at +25 dB compared to the signal level has been added to the output signal with a nominally maximum envelope represented by the graph line 891 and a nominally minimum envelope represented by the graph line 893. Graph 894 represents the result of the correlation operation on the noisy output based on an input excitation sequence of length $2^{14}-1$, while graph 895 represents result of the correlation operation on the noisy output based on an input excitation sequence of length $2^{18}-1$.

Figure 8D:
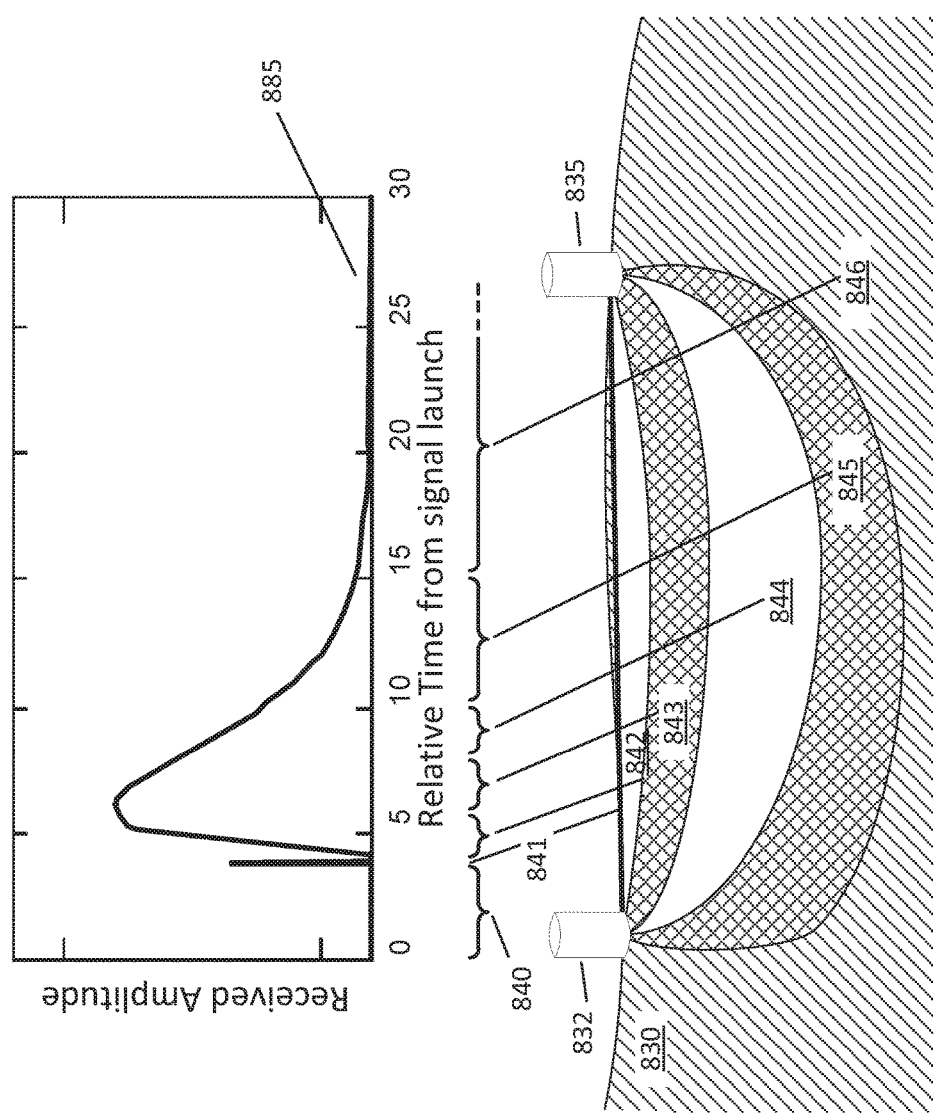
FIG. 8D is a diagram relating the impulse response graph from FIG. 8C to radiation paths through an example cross-section of a measurement sample.

With reference to FIG. 8D, graph 885 from FIG. 8C is shown in the context of an explanation of the waveform developed over time as the impulse response of a sample configured as shown. The lower part of the diagram includes a sample volume 830 juxtaposed with a transmitter 832 and a receiver 835, located a distance away. When an energy impulse is injected into the sample at time zero, there is, at time zero, no resulting output detectable at the receiver. Radiation which travels ballistically from the transmitter 832 to the receiver 835 will travel the ballistic or straight-line path 841. Until that portion of the input energy arrives at the output, as is indicated on the first interval of the graph 840, there is zero received amplitude. At time point 841, EM radiation traversing the sample along the shortest path 841 activates the receiver and causes the spike in received energy (indicated by a spike of graph 885 at about 4 units measured along the abscissa). Some radiation follows paths through the sample close to the surface, following paths that are short because they remain substantially in region 842. This radiation is responsible for the rise over time in the graph region 842. Depending on the characteristics of the sample material, with regard to diffusion, absorption, reflection, and anisotropic features of these effects, more or less of the radiation will follow short paths compared to long paths. The longer paths penetrate farther into the sample and take more time for the EM radiation to reach the receiver; and statistically, over time, much of the remaining radiation is not detectable by the receiver as it either is absorbed, or exits the sample undetected by a receiver. The successive depth of regions shown by 843, 844, 845, and the bulk of the sample 846 illustrate the probable penetration of the energy that is received in the time of graph 885 corresponding to the regions. It would be misleading to say that the correspondence is exact; it is not. However, different delays to correspond to different regimes of paths, and if the regime can be characterized, the results of these characterizations can be used to inform later measurements. Embodiments of the invention include systems that advantageously use the fine-grained ability to segregate the measurements of the delay cohorts of paths, and to perform differential characterization of these delay cohorts.

While the general use of the term 'impulse response' is the response of a system to a unit sized burst of energy injected in zero time, the embodiments herein can more accurately be described by their response to a chip-long pulse. This chip-long rectangular-shaped pulse may be longer than the duration of detectable levels of a typically conceptualized impulse response; in that case, the pulse is similar to a time-limited step function, or more simply, a pulse. Alternately, the chip-time may be considerably shorter than the detectable duration of an impulse response and the chip pulse then more closely resembles an impulse. One skilled in the art will recognize that the shape and duration of the input pulse is convolved in time with the actual impulse response and that what is received and quantified is the pulse response. Depending on the various noise reduction techniques embodied in the various systems described, the pulse response, which can be measured with significantly improved accuracy and resolution, can be usefully deconvolved to provide even finer-grained information. Although the use herein does not strictly fit mathematical interpretation of the term, when used herein, 'impulse response' encompasses the extracted response, of the system being measured, to a single chip-wide pulse of input. The data collected is quantized and limited in time; however, the term is used herein as it captures the combination of impulse, 'chip', step, and pulse response. Impulse response is additionally used describing the calculated result of combining received impulse responses from multiple $\lambda_i$'s.

As used herein, concentration is an amount of a particular material component or analyte. This may be a percentage, or when volume, for instance, is determined, an absolute value may be calculated.

An additional reason for employing lasers (VCSELs) rather than LEDs is that the VCSELs can be pulsed much faster than the LEDs, which is of value when long excitation sequences are to be transmitted, and provides for a more accurate measure of path length.

Examples of Systems for Measuring Properties of Material Components

Figure 9A:
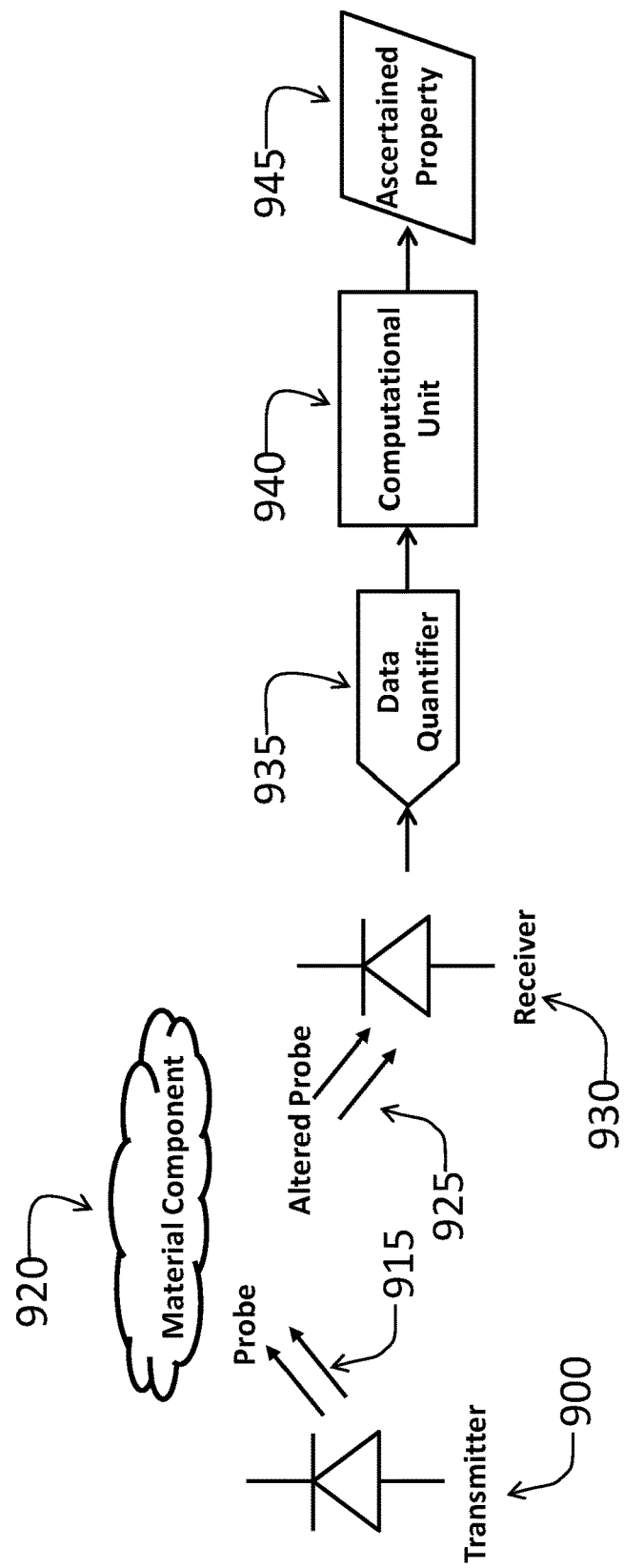
FIG. 9A is a diagram showing components of a system adapted to measure one or more properties of one or more material components.

Referring to FIG. 9A, a system to measure one or more properties of one or more material components includes a transmitter 900 that forms a probe 915 (for example, in the form of light at one or more wavelengths). The probe is directed to interact with material component 920, as a result of which the properties or characteristics of the probe are changed to reflect such interaction and to form an altered probe; the specific nature of the change depends on the properties of the analyte. The presence of the altered probe 925 is detected by the receiver 930. The data representing the altered probe 925 and acquired with the receiver 930 is quantified by the data quantifier 935, in ways described below, and the quantified data is then processed by the computational unit 940 to produce an ascertained property 945.

Figure 9B:
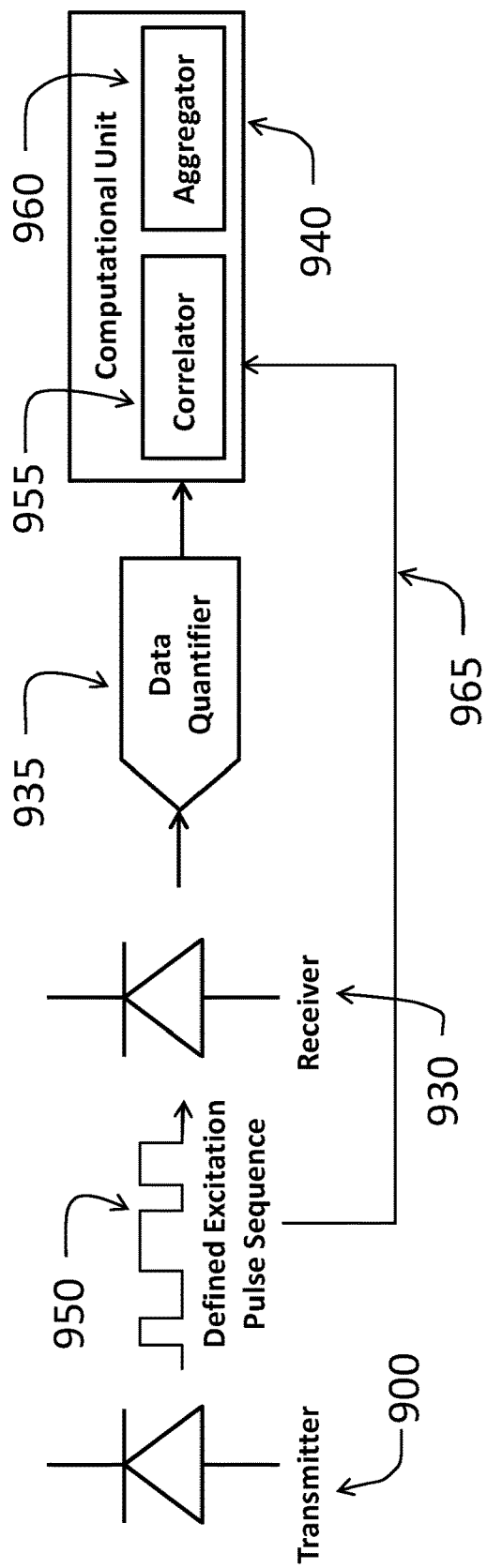
FIG. 9B is a diagram illustrating components of a system adapted to increase signal-to-noise ratio associated with measurement data obtained using a transmitter and receiver.
Figure 9C:
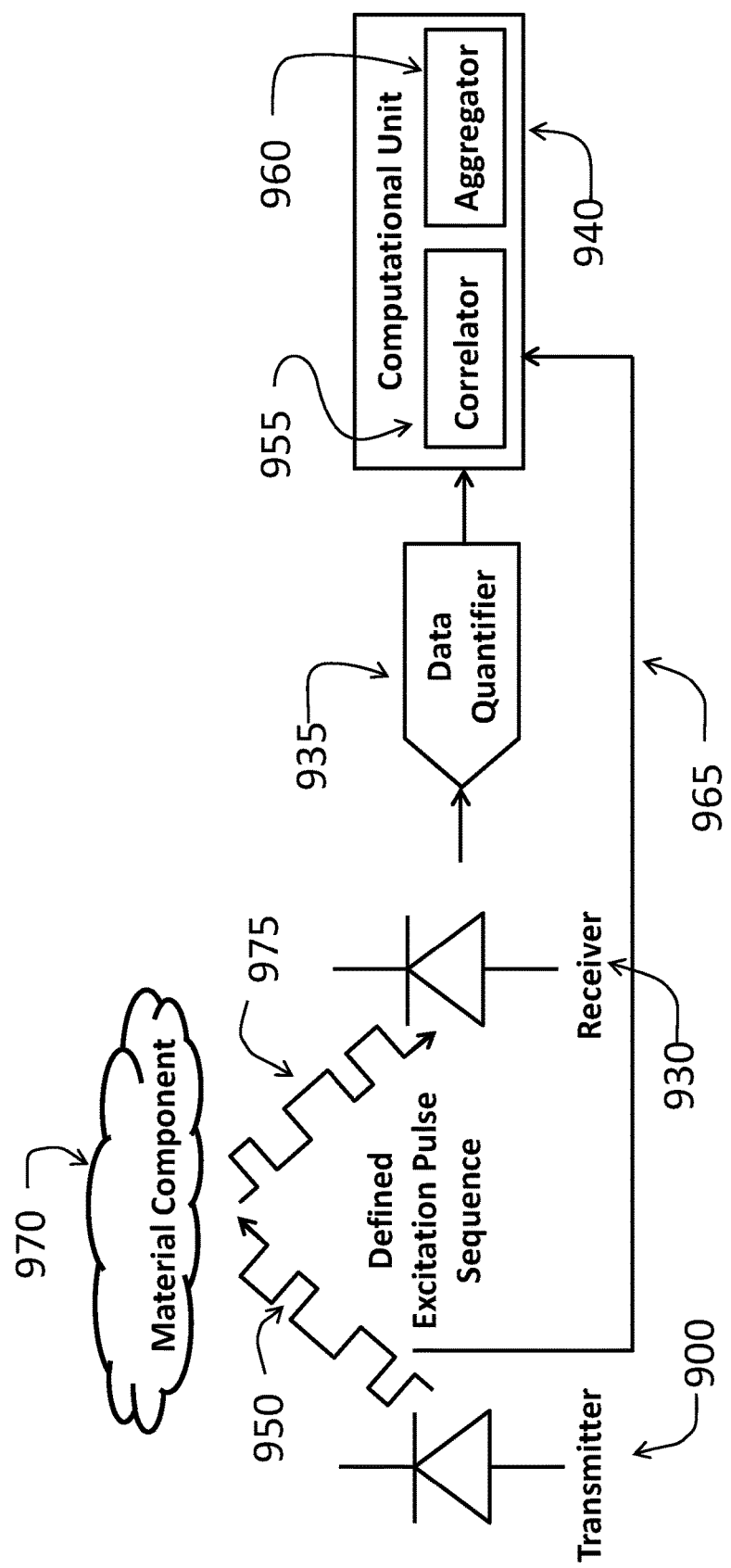
FIG. 9C is a diagram illustrating components of a system adapted to transmit and receive multiple excitation signal sequences to increase signal-to-noise ratio and/or decrease motion artifacts of associated measurements.

With reference to FIG. 9B, the system may be augmented to increase the signal-to-noise ratio from measurements obtained using a transmitter 900 and receiver 930 by having the transmitter driven with an excitation sequence generator. In this case, each of the components of light (of the probe) at different wavelengths is modulated by a corresponding, unique excitation sequence. In this embodiment, the receiver 930 feeds the signal through a data quantifier 935 to a computational unit 940 composed of at least the parts of a correlation circuit 955 and an aggregating circuit 960. In this embodiment, each correlator has as input to its operation both the received signal and the unaltered defined excitation pulse sequence 950 through a direct connection 965. The correlator can beneficially reference the excitation sequence to perform the cross correlation of the received signal with the probe. Examples of the implementation of such correlation procedures are described below. With reference to FIG. 9C, an additional system is shown, adapted to transmit and receive multiple excitation sequences to facilitate correlation thereby increasing signal-to-noise ratio and/or decreasing motion artifacts. The transmitted signal is directed to interact with the material component that may be a turbid medium or a molecular dye 970. The probe includes light at one or more wavelengths, light portions at each wavelength modulated by a corresponding unique excitation sequence. Multiple correlators can be used to provide for concurrent processing of the multiple wavelengths of the altered probe 975.

Controlling the Location of Sampling Point(s) Using Micro-Mirrors

In making measurements with light sources, it is often desirable to control within tight tolerances the location where the light makes contact with the sample to be measured. One application that makes use of such measurements is the read/write mechanism on an optical disk drive such as digital video disc (DVD) or blu-ray disc (BD). The current state of the art positions the laser using a worm drive with servo control. The advantage of such a system is the position of the laser is continuously variable with accuracy limited by the screw, the motor, and control system. However, the disadvantage is that it requires a significant amount of hardware, time delay, and energy (to move the mass) to accurately position the laser with respect to the sample location.

Another example application is Universal Product Code (UPC) scanners. In one implementation, a laser light is scanned across the UPC using a single rotating mirror. In another implementation, a laser light is scanned across the UPC using a hologram. Unlike the invention described herein, the incident angle of the light to the UPC is not controlled, nor is the distance from the light source to the sample or from the sample to the receiver.

The advantage of the invention described herein versus a worm drive is that it requires less hardware, little time, and lower energy to position the laser beam at the sample location to be measured. Related benefits are increased reliability due to simplified mechanical parts and the reduced size of the apparatus. Unlike UPC scanners, the invention described herein simultaneously controls the distance and the incident angle to the sample. Though controlling the distance and incident angle is not necessary for UPC scanners, it is necessary for other sampling applications.

With reference to FIG. 10A, the use of micro-mirrors 1080, possibly as contained in a micro-electro-mechanical system (MEMS) but not limited to such, each with controllable manipulation between at least three (tilted left 1081, non-tilted 1082, and tilted right 1083) positions allows the optical path and thereby the interaction of the probe 1015 with the material component 1020 to be altered during operation. Though the mirrors are shown in an array pattern in FIG. 10A, this is only exemplary, as other patterns are anticipated. The transmitter 1000 may be any light source such as a laser, VCSEL, or LED, but is not limited to those. The receiver 1030 may be a photodiode, PIN diode (a specific type of photodiode), photomultiplier tube, or charge coupled device (CCD)), but is not limited to those. The transmitter emits a wave parallel to the face of the micro-mirror array 1080. One or more micro-mirrors at precise locations in the micro-mirror array 1080 are moved from a non-tilted 1082 position to a tilted 1081 position that directs the probe 1015 toward the material component 1020 to be measured. In one embodiment, the altered probe 1025 is directed to the receiver 1030 by at least one micro-mirror tilted 1081 in one direction and at least one micro-mirror tilted 1083 in the opposite direction.

FIG. 10B illustrates an extension to the embodiment illustrated in FIG. 10A. In this embodiment, there are three micro-mirror arrays: 1080a, 1080b, and 1080c. Micro-mirror arrays 1080b and 1080c are 1×N mirrors in dimension. In addition, the two arrays are perpendicular to the plane of micro-mirror array 1080a. The transmitter 1000 transmits light in parallel to micro-mirror array 1080b where it is reflected off tilted mirror 1081b (1 of N possible micro-mirrors in the array) directing the light across one row of micro-mirror array 1080a and parallel to micro-mirror array 1080a. At that point, the apparatus works as shown in FIG. 10A, with the light interacting with the material component and being reflected off of micro-mirror 1083. Unlike FIG. 10A, the light is then reflected off micro-mirror 1081c in the micro-mirror array 1080c. The light reflected by micro-mirror 1081c is then received by receiver 1030. With this invention, each row on the micro-mirror array 1080a may be used to sample a two dimensional area of the material component. Micro-mirror array 1080a is shown with each row offset from the previous one (i.e., staggered rows). The staggering of the rows is only exemplary. The rows could also be one above the other and therefore not staggered.

Figure 10C:
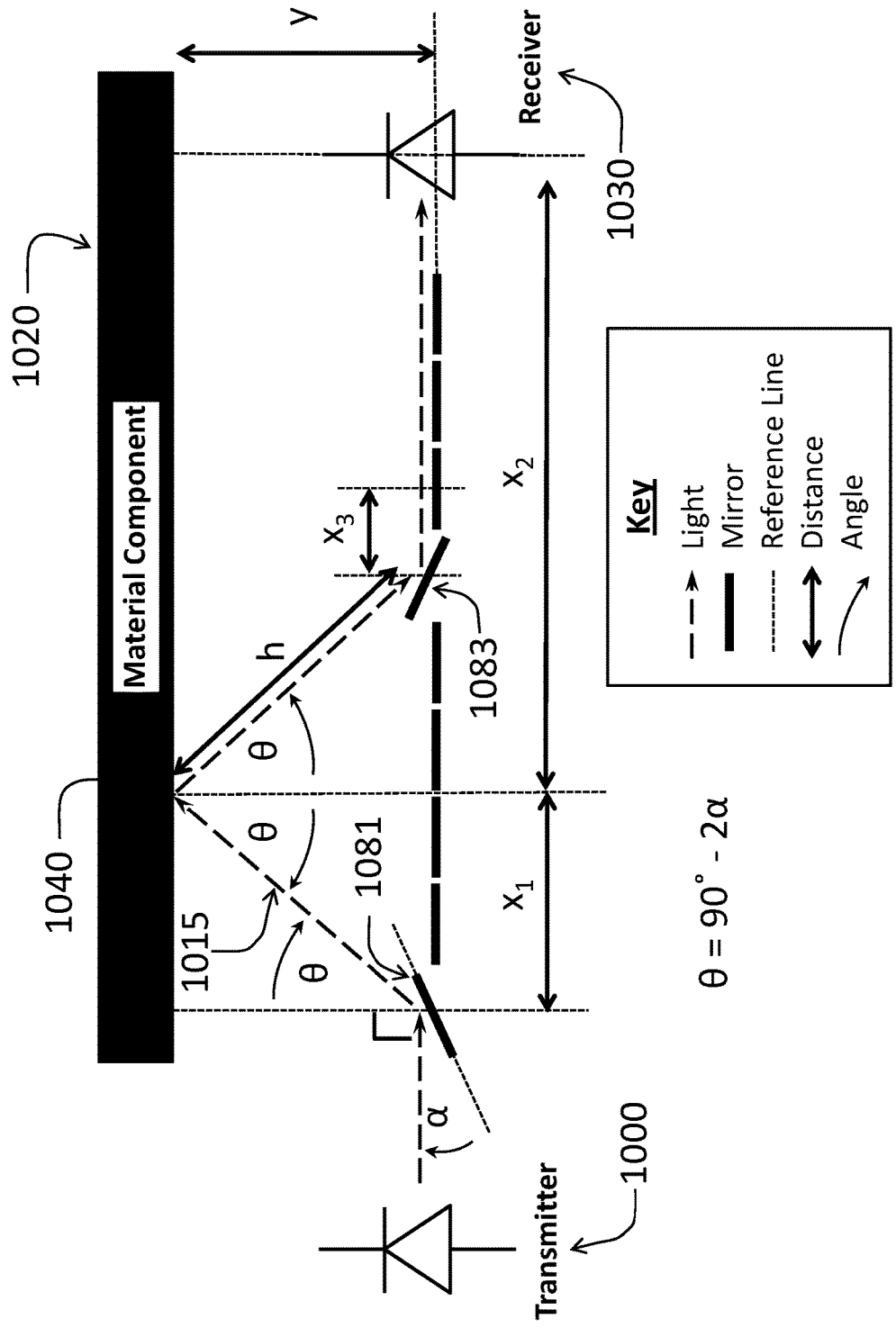
FIG. 10C is a diagram showing the basic layout of the system of FIG. 10A and the related geometrical parameters.

FIG. 10C shows the efficacy of this invention for precisely controlling the distance from a point 1040 where the light is reflected from the material component 1020 to the receiver 1030. For the example shown, two mirrors are used to control the distance and the array is one-dimensional (i.e., there is only one row of mirrors). The first mirror is tilted as shown by 1081 and the second mirror is tilted as shown by 1083. The distance (i.e., d) from the point 1040 to the receiver 1030 is shown by equation 45. Using a simplifying assumption that the material component 1020 and the micro-mirror array are parallel, then when the mirrors to the right of the two tilted mirrors are tilted, and the prior two tilted mirrors are put in non-tilted positions, then the distance is that shown in equation 46. Thus, the distance is decreased by the distance between two adjacent mirrors. The equation is generalized to equation 47 where N is the number of mirrors to the right of the positions shown in the figure. Note that this simplified equation is dependent on the material component being parallel to the micro-mirror array and the angle α (and therefore θ) being constant. One of the advantages of micro-mirrors is that the angle of tilt is repeatable and consistent from mirror to mirror.

$$d = x_2 - x_1 + h \quad (45)$$

$$d = x_2 - x_1 + h - x_3 \quad (46)$$

$$d = x_2 - x_1 + h - Nx_3 \quad (47)$$

The advantage of having an array of precisely spaced micro-mirrors is the capability of selecting with fine resolution the distance to the receiver from the "point" where the probe is scattered by the material component. By optimizing this distance, the desired point to be measured can be located and the resulting measurements improved. In addition, the material component can be scanned (by changing which one or more micro-mirrors is tilted) to quickly locate areas of the material component with the properties desired.

Other advantages include compensation for variability in the y direction (as shown in FIG. 10C). If y increases then $Nx_3$ can be increased to keep the total distance "d" constant.

Figure 10D:
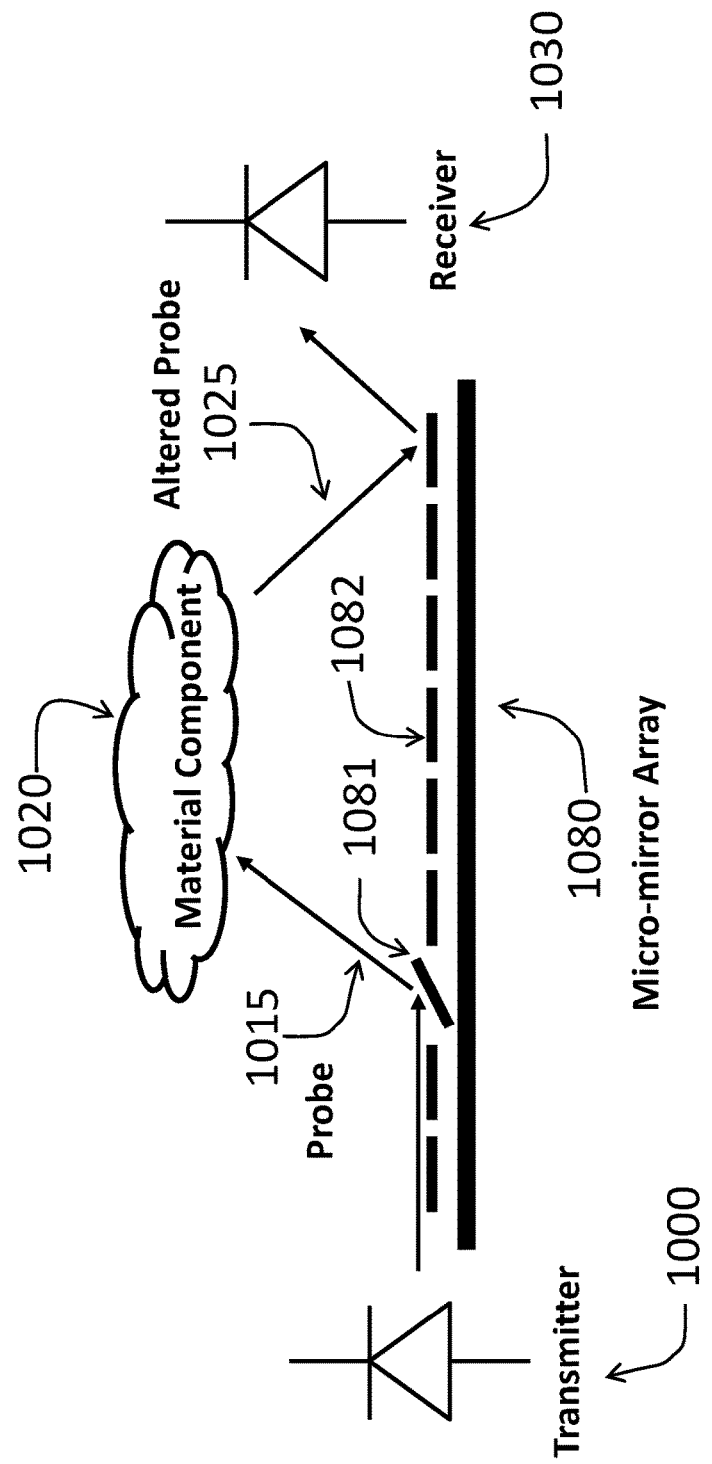
FIG. 10D shows the embodiment of FIG. 10A in a different operational configuration.
Figure 10E:
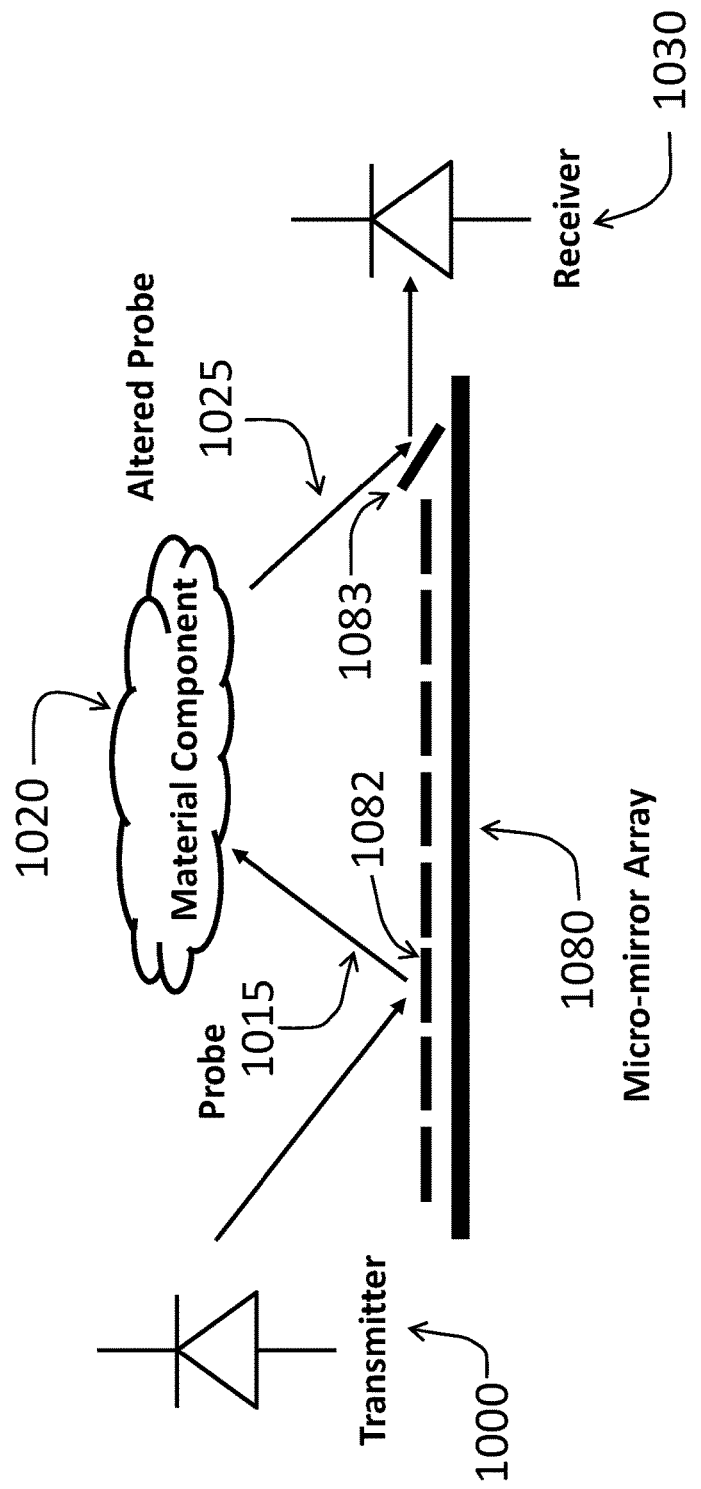
FIG. 10E shows the embodiment of FIG. 10A in another operational configuration.

The paragraphs above have made use of a simplifying assumption, that there is a single point where the probe 1015 reflects from the material component 1020, producing the altered probe 1025. However, many material components of interest do not simply reflect the light, but in addition, absorb, refract, and scatter the light. Therefore, there is not a single ray coming from the light interacting with the material component but a multitude of rays scattered by the material component as it interacts with the light. This understanding leads to other useful alternatives for operating this device. FIG. 10D shows a single tilted mirror 1081 with receiver 1030 receiving light reflected from one or more of the non-tilted mirrors 1082. FIG. 10E shows the complementary operation with transmitted light reflecting off one or more non-tilted mirrors 1082, interacting with the material component, and being scattered back to a tilted mirror 1083 and reflected to the receiver 1030.

Figure 10G:
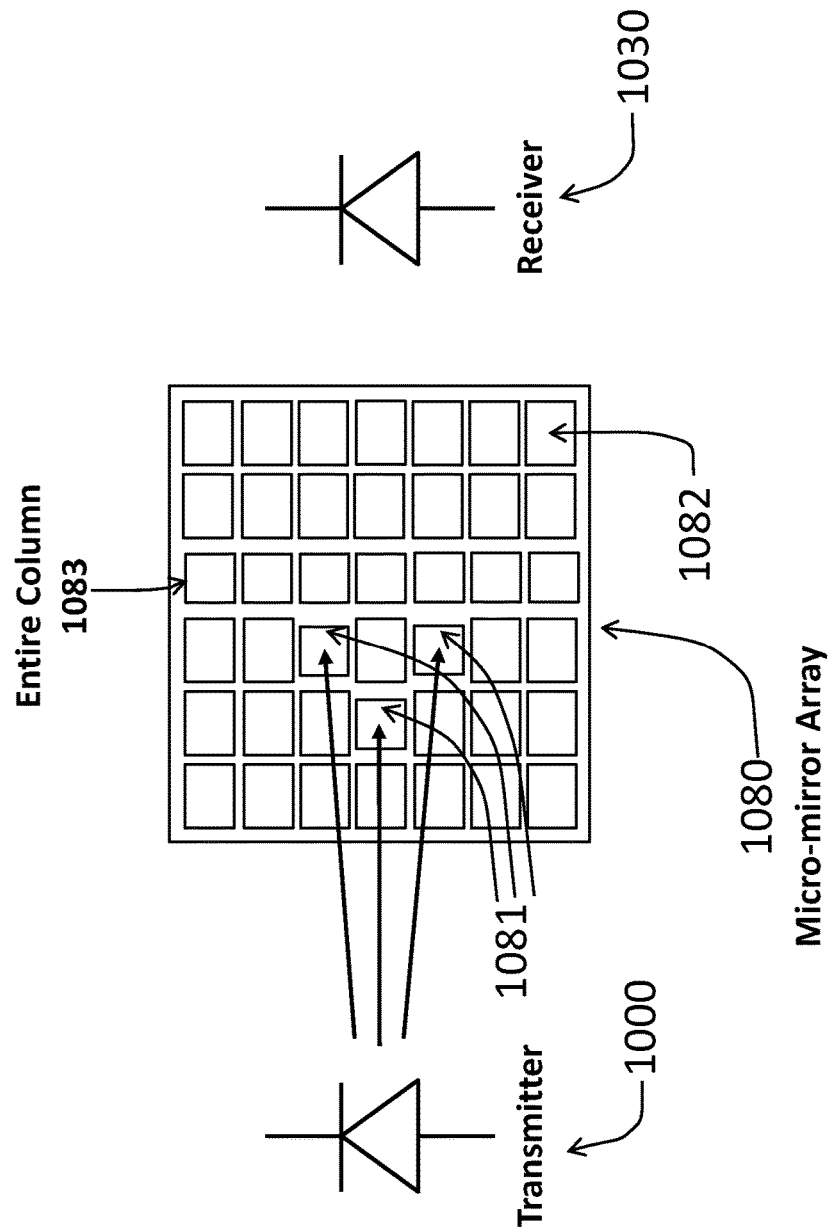
FIG. 10G shows the embodiment of FIG. 10A in a top plan view.

Some material components will diffuse the light. Some of this light will exit the sample at parts of the micro-mirror array that are not intended to be active. To reduce the amount of diffused light reaching the receiver though non-tissue paths a barrier can be introduced. FIG. 10F shows how such a barrier 1040 may be used. Even if the barrier is in contact with the material component, the light may still travel to the receiver as it travels through the material component and exits on the right hand side of the barrier. An alternative barrier technique is shown in FIG. 10G. In this case, a column of micro-mirrors is used as a barrier. By tilting one or more micro-mirrors 1083 in the opposite direction to those micro-mirrors 1081 reflecting the light, then less light is allowed to pass from the left of the micro-mirrors 1083 to the receiver 1030. However, as previously shown, the 1083 micro-mirrors reflect the light to the right toward the receiver.

FIG. 10G shows the second dimension of operation of a two dimensional micro-mirror array. The tilted micro-mirrors 1081 are used to select portions of the transmitted light (probe 1015). In this manner, with mirrors smaller in dimensions than the width of the transmitted wave of light, a wave smaller than that generated by the transmitter is reflected for a probe. The micro-mirrors 1083 tilted in the opposite direction are used to trap light that passes by the micro-micro-mirrors 1081. Another possible use of the light trapping mechanism is to scavenge energy from the light that will not otherwise serve a useful function.

Figure 10H:
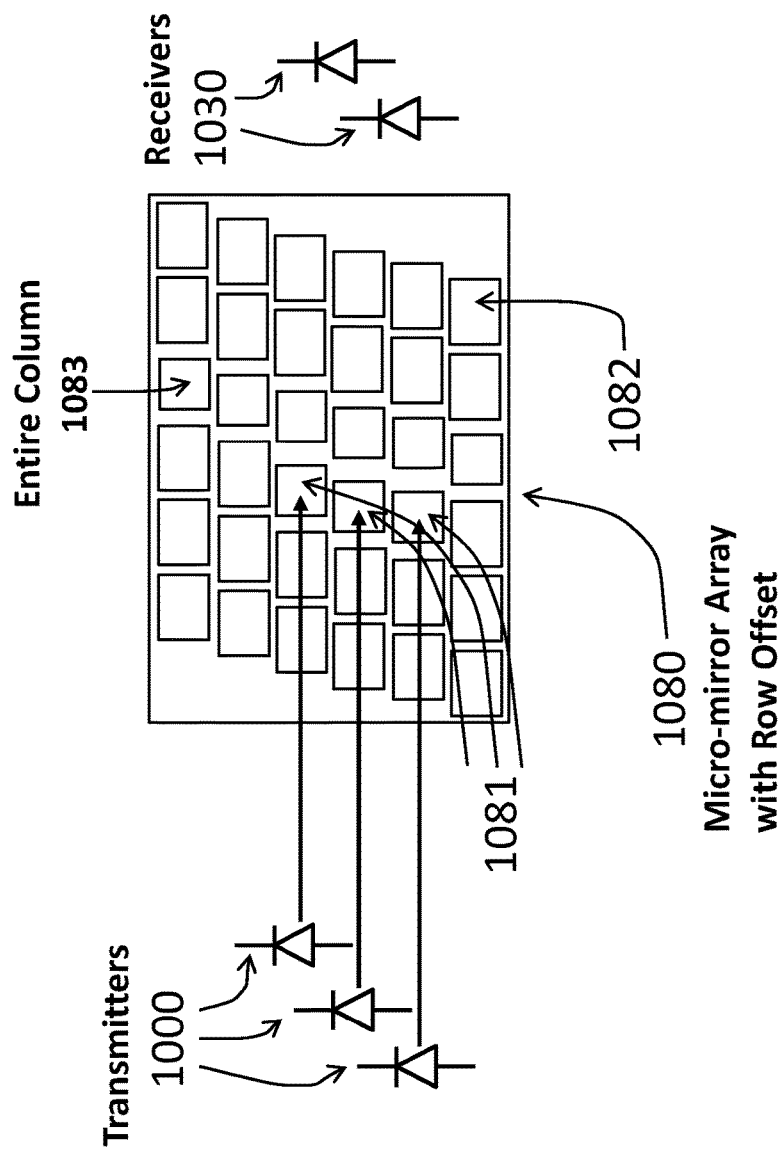
FIG. 10H shows a top plan view of an embodiment related to that of FIG. 10A, in which the micro-mirror array is configured with a with row-to-row offset.

Finer granularity of distances than those between micro-mirrors can be achieved by using staggered rows of micro-mirrors, such as shown in FIG. 10H. In this case, the stagger distance is less than the distance from the centerline of one mirror in a column to the next mirror in the same column. FIG. 10H also introduces multiple transmitters 1000 and multiple receivers 1030. One use of multiple transmitters is to allow multiple wavelengths to be transmitted, and if desired simultaneously. One of the advantages of this invention is that each wavelength can, if desired, have a unique distance to the receiver. Multiple receivers may be used to facilitate the selection of multiple distances from the sample to the receiver. Finally, each receiver can also be dedicated to a particular wavelength, or range of wavelengths, of light. This can be useful to aid in separating signals and in selecting more than one type of receiver, as in ones particularly suited to the wavelengths being transmitted.

FIG. 10I shows a micro-mirror pattern using mirrors with a hexagonal shape. This pattern helps maximize the amount of reflected light by minimizing the amount of light passing between the tilted 1081 mirrors.

Figure 10J:
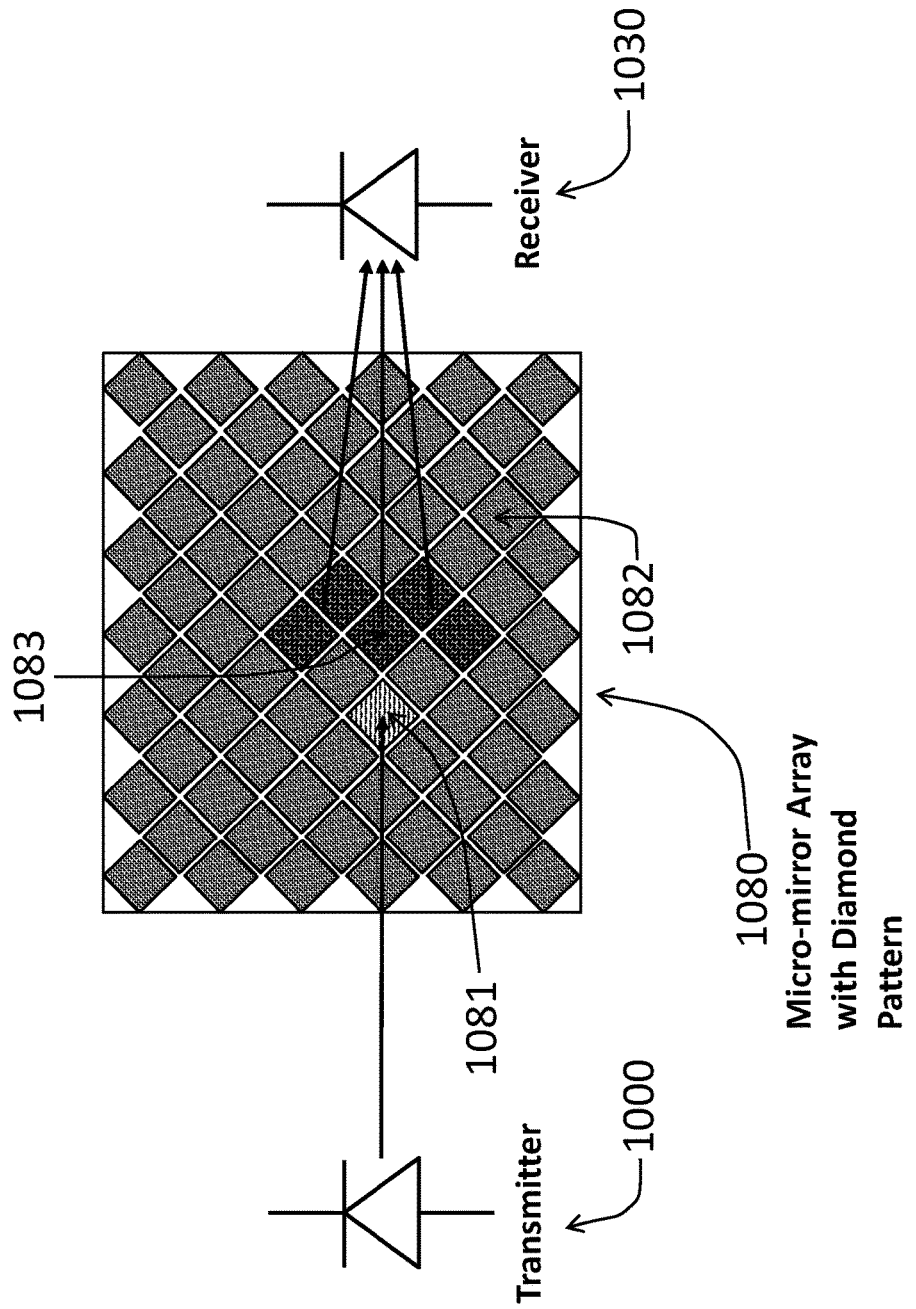
FIG. 10J shows a top plan view of another embodiment of the invention having a micro-mirror array with rectangular mirrors arranged in a diamond pattern.

FIG. 10J shows a micro-mirror array using a diagonal pattern. Micro-mirrors in production today often have the pivot axis across the diagonal.

Figure 10K:
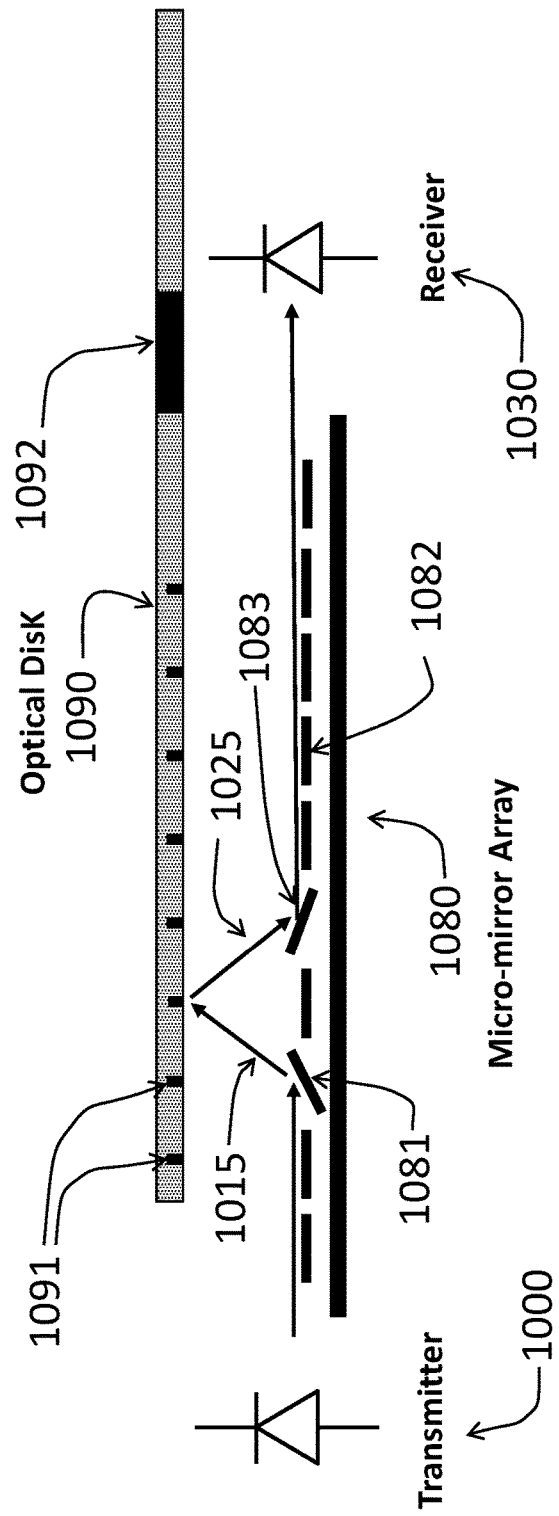
FIG. 10K shows a side plan view of another embodiment of the invention as specifically applied to disk drives.

FIG. 10K illustrates the application of the invention for use in reading or writing an optical disk 1090 (also showing the hole 1092 for the spindle). The tracks 1091 for this example are aligned with a single row of micro-mirrors. Using the micro-mirror arrays illustrated in FIG. 10B allows for all rows in micro-mirror array 1080a to be used as necessary to align the light rays with the tracks on the optical disk 1090. Most, if not all, optical disks currently manufactured use spiral tracks. Several techniques may be used with this invention to facilitate the tracking of spiral tracks. One such technique is a worm drive with servo control, as typically used in optical disk drives. However, in this application much less range of motion is required than in typical optical disk drive laser assemblies. Another technique is to enable tracking through the micro-mirrors by adjusting the angle of tilt for the mirrors both on the transmit and on the receive side. An additional advantage of this invention is with known track-to-track distances, once a track is located, then the mirror positions required to find any other track is known and can be changed rapidly.

In reference to all FIG. 10A-K, each describes an implementation where the angle of the tilted mirrors is constant. There are obvious advantages of allowing multiple angles and even continuously variable angles. For instance, continuously variable angles may be used for sampling continuous locations rather than the discrete locations for mirrors with a single angle.

The use of micro-mirrors in the path of the probe or altered probe may reduce the received signal. This technique can be made more useful in practice by utilizing the various encoding techniques and post-processing techniques described herein.

Sequence Generator and Excitation Sequences

Linear Feedback Shift Register. An excitation sequence generator may be implemented as a programmable linear feedback shift register (LFSR); different settings on the internal registers of the LFSR will produce different excitation sequences. There are several ways of designing the LFSR to generate different patterns, which patterns may be quite long without repetition; and the transistor-level implementation is not complex and will not be a very high-transistor-count circuit. In one embodiment, with reference to FIG. 15A, a shift register 1500 produces a shifted output 1510. This output 1510 is "fed back" to the syndrome logic 1515. The syndrome logic, based on the configuration register 1520 provides the output 1510 to configured elements of the shift register, wherein the output is exclusive-ored with the bit being shifted in to modify that bit value so that it may be stored in the next element of the shift register when triggered by the clock pulse 1505. Optionally, the configuration register 1520 can be written with a new value, said value being supplied from a value source, e.g. but not limited to a processor (not shown) data bus. Toggling the write control signal 1530 will cause the configuration register 1520 to update to the value supplied in the value bus 1525.

Incorporated in this LFSR design is a "start pulse" output signal line 1540, which may be optionally used in the receiver and correlator circuitry to determine the sequence temporal boundaries. The communication of sequence boundaries can optionally be used for automatic gain control in the receiver as described below. It is recognized that the sequence start signal 1540 can be produced in a number of ways. In the pictured embodiment, a pattern matching circuit 1535 is used.

Figure 15A:
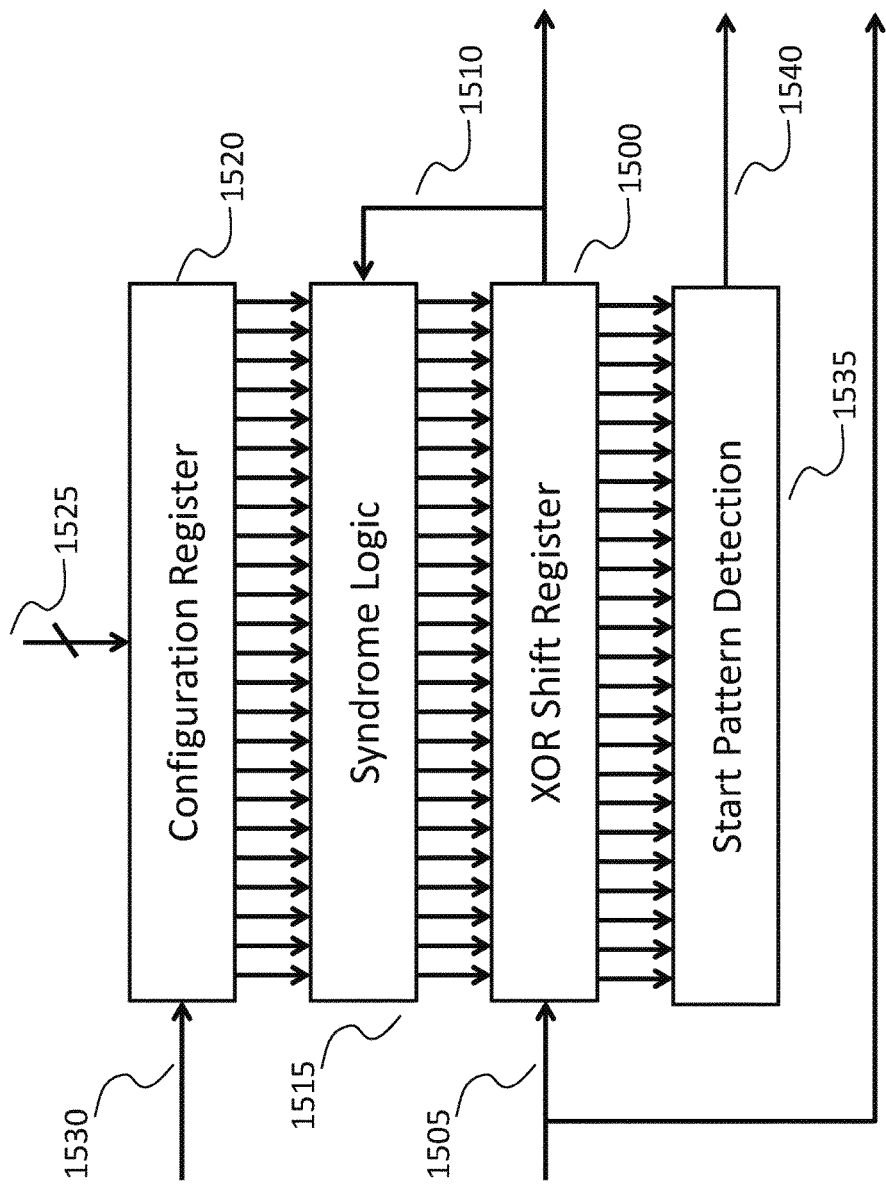
FIG. 15A is a diagram illustrating an embodiment of a linear feedback shift register (LFSR) for use as a source of an excitation sequence.
Figure 15B:
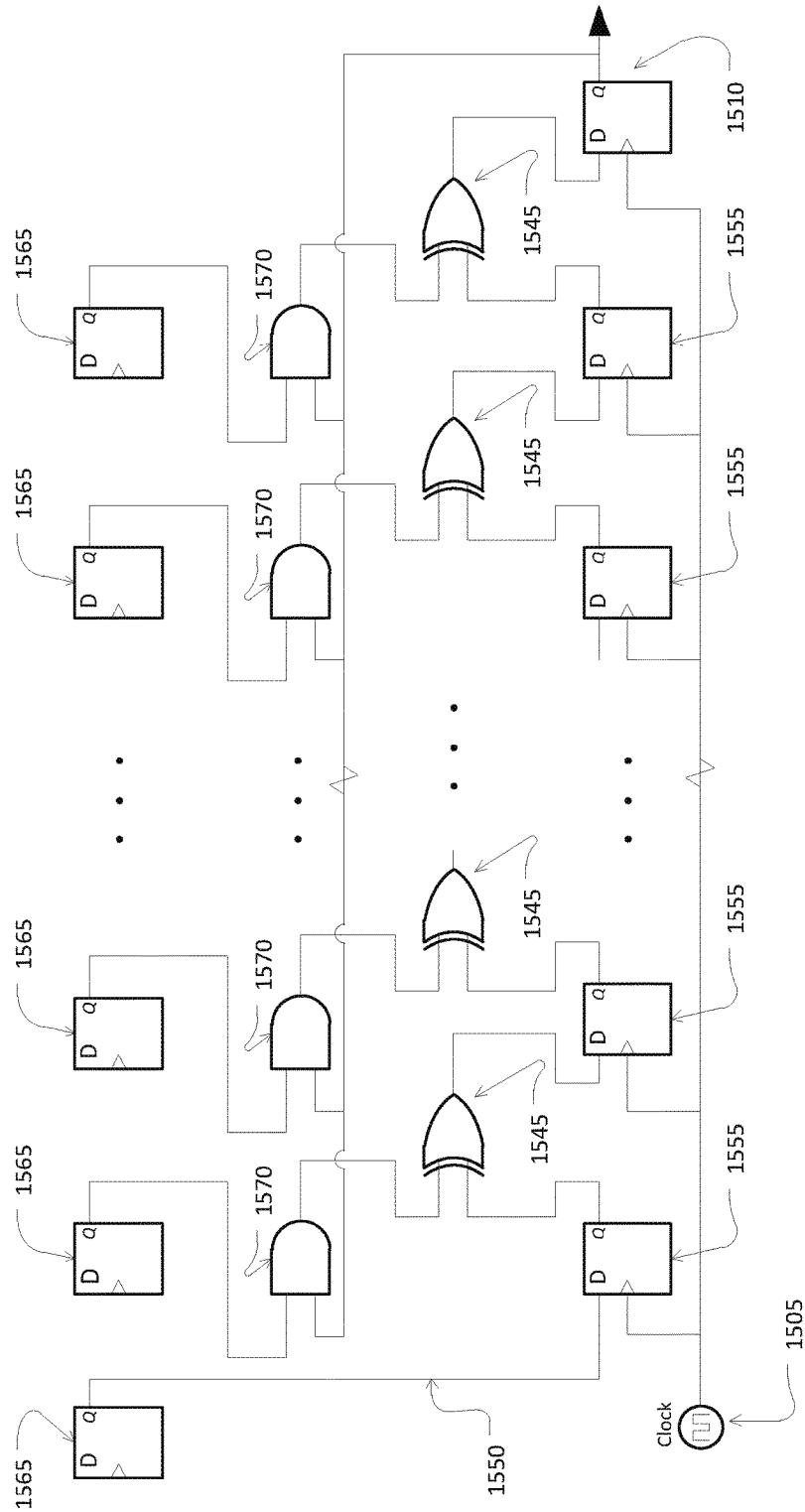
FIG. 15B is diagram illustrating electronic circuitry associated with the LFSR embodiment of FIG. 15A.

With reference to FIG. 15B, the details of an exemplary LFSR are shown with the shift register elements 1555 shown as digital latches, receiving an input and propagating that input to a storage element in the latch and providing the contents of the storage location at the output. The input is propagated to the internal storage location on the rising edge of the digital signal designated clock 1505. The leftmost element in the shift register takes its input from the leftmost element of the configuration register 1565. The logic is arranged in groups corresponding to the logic needed to update each element of the shift register. The collection of one each of a configuration register element 1565, an AND logic gate 1570, an exclusive-or (XOR) logic gate 1545, and a shift register storage latch 1555 comprises the syndrome logic 1515 used to update the shift register each time the input clock 1505 toggles. Each successive (traversing from left to right) shift register element takes its input from the output of an XOR logic gate 1545. The two inputs of the XOR gate 1545 are the previous element of the shift register 1555 and the output of an AND logic gate 1570. The inputs to this AND gate 1570 are the value of the element of the configuration register corresponding to this bit group and the output of the shift register 1510. It is appreciated that this logic, when configured with an appropriate configuration value will provide a deterministic sequence of logic ones and zeros in a repeating pattern. With reference to FIG. 15B, the center of the figure contains four ellipsis patterns, i.e., '. . . ' these patterns are used by those familiar with the convention to indicate the presence of an indefinite number of repetitions of the elements on either side of the ellipsis patterns. This convention of illustrating a larger structure with a smaller number of repeated patterns is used in several of the illustrations including at least FIGS. 15B, 17B, 17E, 18B, and 19.

Noise Based Generation. With reference to FIG. 16, additional embodiments of excitation sequence generation are illustrated. FIG. 16A illustrates the use of a noise generator 1600, such as but not limited to a microphone, a back biased diode junction, a receiver of atmospheric noise, or other time varying process. The output of the noise generator 1600 is fed to a low pass filter 1610. The low pass filter provides an average value reference as one input of a comparator circuit 1620. The other input of the comparator circuit 1620 comes directly from the noise generator 1600. As will be appreciated, the instantaneous value of the noise generator may be at times above the longer-term average provided by the low pass filter 1610, at which time the output 1630 of the comparator 1620 will be driven to the extreme of a logic one. At other times, the instantaneous value of the noise generator will less than the longer-term average, and the output of the comparator 1620 will be driven toward the other extreme, a logic zero. Using this circuit an analog time varying signal can be converted to a binary signal.

Storage based generation. A technique that may be used for the production of a defined excitation sequence is a predetermination of a sequence and the storage of the elements of that sequence in an addressable storage component 1640, as illustrated in FIG. 16B. The excitation sequence can be produced by driving the address lines of the memory device with a counter 1650. Successive memory locations will be presented to the output of the memory, creating the sequence of values comprising the excitation sequence 1630. As a variation, when more than one sequence is needed, as in the embodiments which provide for the concurrent driving of multiple lasers, multiple bit wide memories can be used, with each bit index being used to drive a separate laser. When calibration sequences differ from measurement sequences, having access to multiple sequences can present advantages. In this case, the counters may be used concatenated with configuration registers to cycle through one group of memory addresses, then with a change to the configuration value, to cycle through another group of memory locations.

With reference to FIG. 16C, a processor 1690, connected through a memory interface unit 1670 to a memory unit 1660, fetching instructions from the memory and decoding 1680 and executing those instructions may execute a stored program or algorithm, and by writing to a memory location which is able to output a logic signal 1630, produce the excitation sequence under program control.

The excitation sequence repeats in time over and over again, with optional brief durations between each sequence when no bit transitions are transmitted. Another way to generate this quiet time is to include a fixed set of zeros at the end of the defined excitation sequence. The output from the excitation sequence generator is fed to the laser driver circuitry, which in turn modulates the excitation sequence onto the laser. The laser driver and the light source itself is an analog portion of this embodiment of the measurement device. Either an on-off keying modulation can be used in one embodiment, or in another embodiment the laser light is modulated from bright to dim and back, but does not completely extinguish as long as each instance of the excitation sequence is being transmitted.

Examples of Correlators Useful for Spectrometry

Figure 17A:
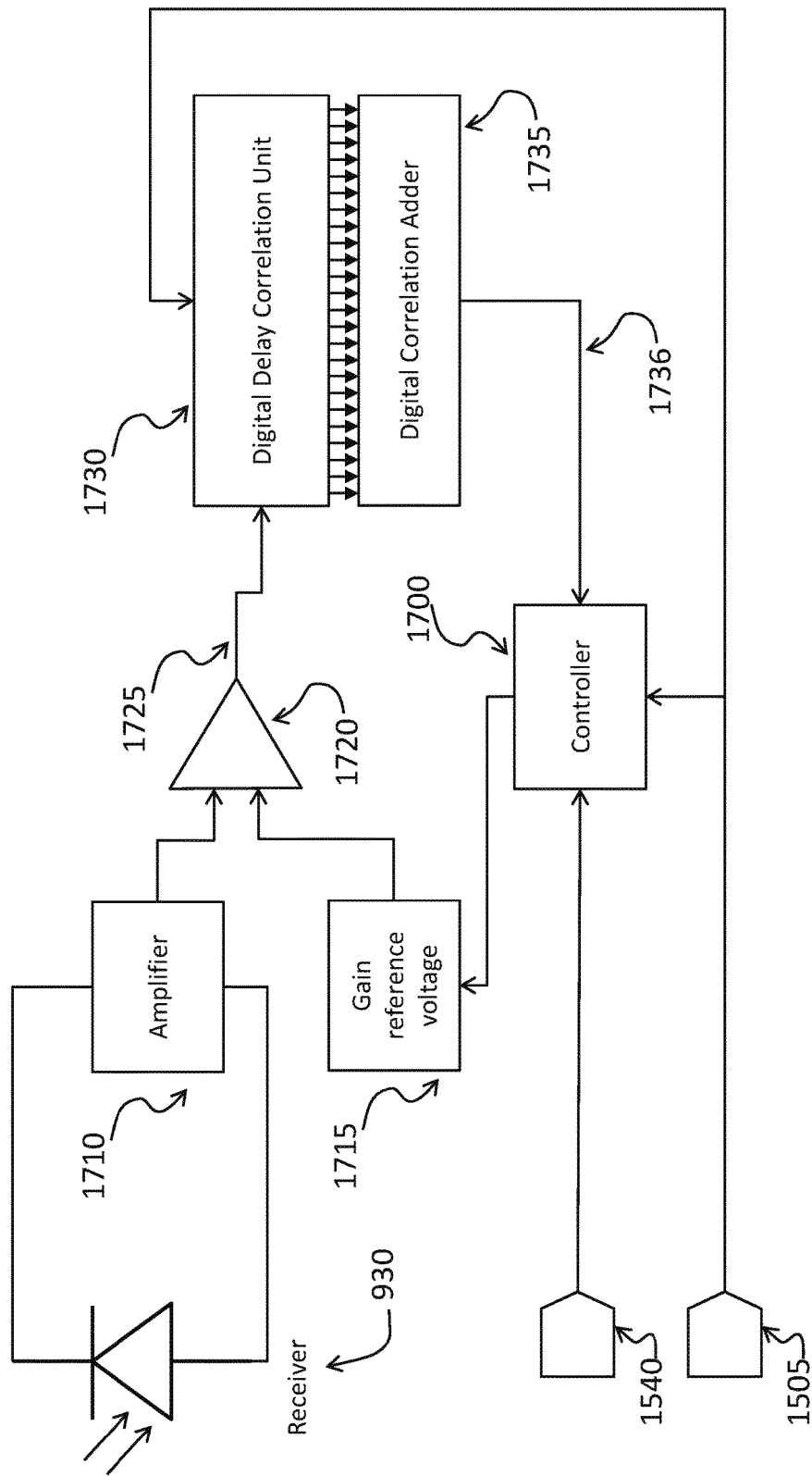
FIG. 17A is a diagram showing a portion of a single bit digital correlator for use in a receiver of an embodiment of the invention.

Binary Digital Correlator for Pulse Oximetry. With reference to FIG. 17A, techniques for producing a digital correlator for use in spectrometry are described. These techniques can also be used in the additional applications described herein. Correlation embodiments that improve SNR significantly may advantageously be implemented in the form of an integrated circuit, thereby allowing the correlator to function as part of a mobile, body-worn unit. In the case of pulse oximetry, which is a relative measure of blood oxygen saturation, not an absolute measure, it is not required to measure the path length of the light through the tissue.

One embodiment of a correlator for spectrometry contains a preponderance of digital circuitry using a binary received signal to detect correlation.

On the receive side of the circuitry, the laser light, after passing through the tissue, impinges on a solid-state photodetector 930 such as a P-I-N(PIN) diode, an avalanche photodiode, or a photomultiplier tube, any of which will convert the optical signal into an analog, time-varying electrical signal. This signal is then fed into an analog amplifier stage 1710, whose amplification factor is modified in a closed-loop fashion as follows: the start pulse 1540 from the excitation sequence generator informs the controller 1700 when the pulse train is to begin; and if by the end of the excitation sequence, as indicated by the next start pulse 1540, the correlator 1730 has not generated a correlation "match" 1736, then for the next receipt of the pulse train, the amplification factor will be increased. This increase will continue in repetitive steps until either the correlator shows a correlation match, or the amplification factor is at its maximum. A threshold detector 1720 on the output of the automatic amplification stage 1710 is needed to convert the analog electronic signals from the photodetector into a binary pulse train, but again this is well-known circuitry.

The correlator digital circuitry 1720 is clocked with the same clock pulse train 1505 that drives the excitation sequence generator.

Figure 17B:
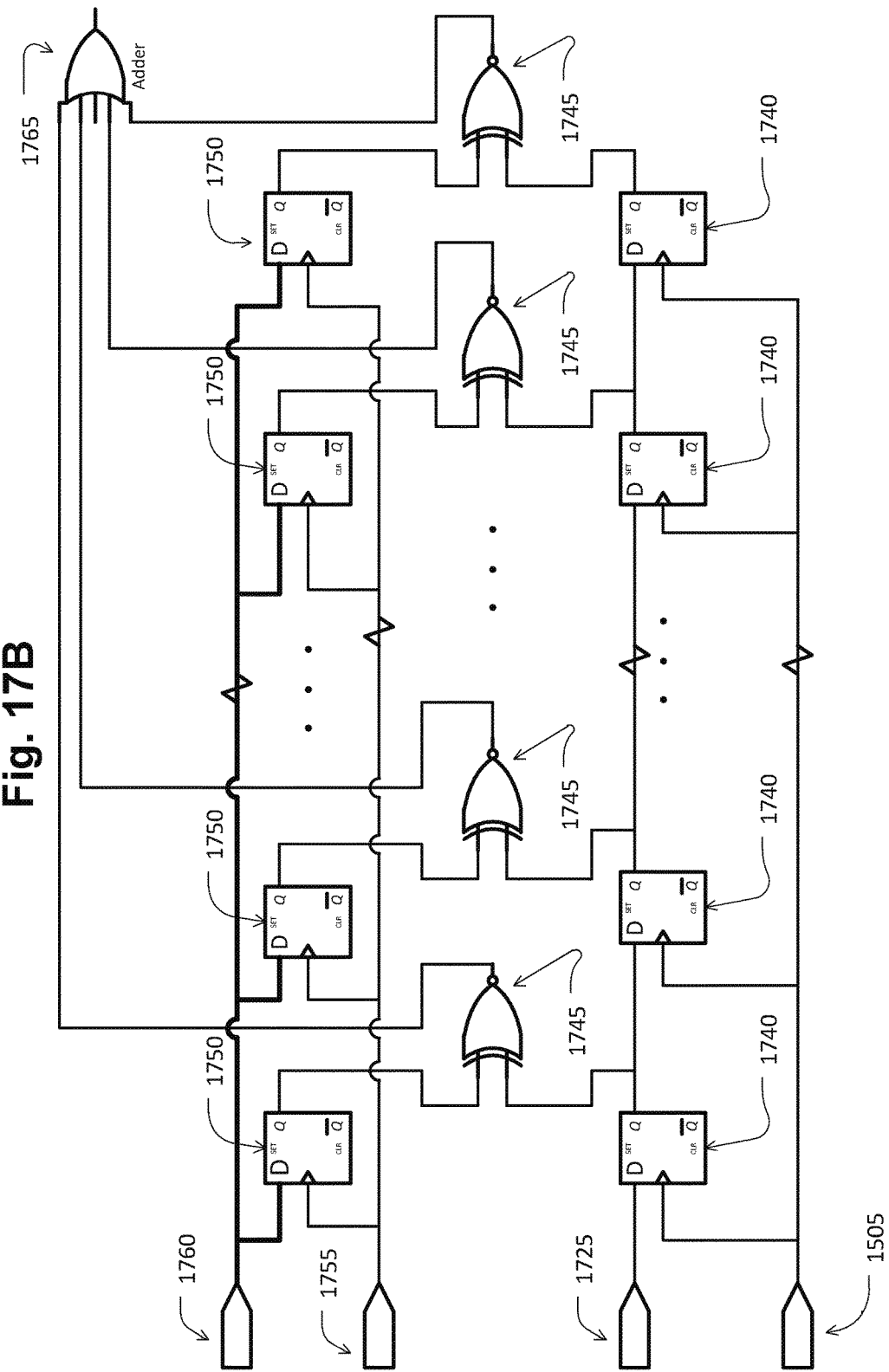
FIG. 17B is a diagram of electronic circuitry associated with the digital correlator of FIG. 17A.

With reference to FIG. 17B, the elements of the digital correlator consist of latches 1750 (grouped in registers) to hold the pre-determined bit pattern of the excitation sequence; a linear train of flip-flops 1740 (latches) through which the pulse train is propagated, clock cycle by clock cycle 1505; a group of XNOR gates 1745 which detect if the propagating bits in the received pulse train match the ones or zeros in the static excitation sequence holding register (one-bits must match one-bits, and zero-bits must match zero-bits, across the entire excitation sequence, for a full match to be identified). The output of each of the XNOR gates is fed to a binary adder 1765, which generates a sum value on each clock pulse. When a full match occurs, the binary adder will generate a large binary output value, which defines that a match occurred, and when in time the match occurred. On average, only half of the bits will match the pattern during each clock cycle. However, during the clock cycle corresponding to the alignment, that is, when a match occurs across all excitation sequence bits simultaneously, the output of the binary adder 1765 will be at a maximum value, the expected magnitude of which is well known and scaled by sample losses.

As used herein, an "XNOR gate" is a two-input one-output circuit with the characteristic that the output will be a one when the inputs match; otherwise, it will be a zero. As used herein, the term "binary adder" is a circuit with N-inputs and $\lceil \log 2(N+1) \rceil$ outputs such that the outputs taken together represent a binary number that is the count of the inputs that are one. An example of the binary adder is a circuit with 10 inputs, $I_0$, through $I_9$, and 4 ($\lceil \log 2(10+1) \rceil$) outputs, $O_0$, $O_1$, $O_2$, and $O_3$. When the inputs, $I_0 \ldots, I_9$ are, for example $\{0, 1, 1, 1, 0, 0, 0, 0, 0, 0\}$, the outputs, $O_0 \ldots, O_3$ would be $\{1, 1, 0, 0\}$ representing the value of three. The same output would be produced with input patterns of, for example $\{0, 0, 0, 1, 1, 1, 0, 0, 0, 0\}$, $\{0, 0, 0, 0, 0, 0, 1, 1, 1\}$, or $\{0, 1, 0, 1, 0, 0, 0, 1, 0, 0\}$.

With reference to FIG. 17A, the input to the correlator is a comparison between the output of the amplifier 1710 and a gain reference voltage 1715. The comparator 1720 compares the two values and, similar to the noise resolving circuit of FIG. 16A, produces a binary output 1735 to feed into the correlator.

With reference to FIG. 17B, the register elements 1750 that hold the reference of the excitation sequence to be compared against, may be updated with new values. The new values are presented by the N-bit data bus 1760, and will be stored in the excitation sequence register bits 1750 when the write pulse 1755 toggles. In this manner, a circuit may be used with multiple reference sequences.

Figure 17C:
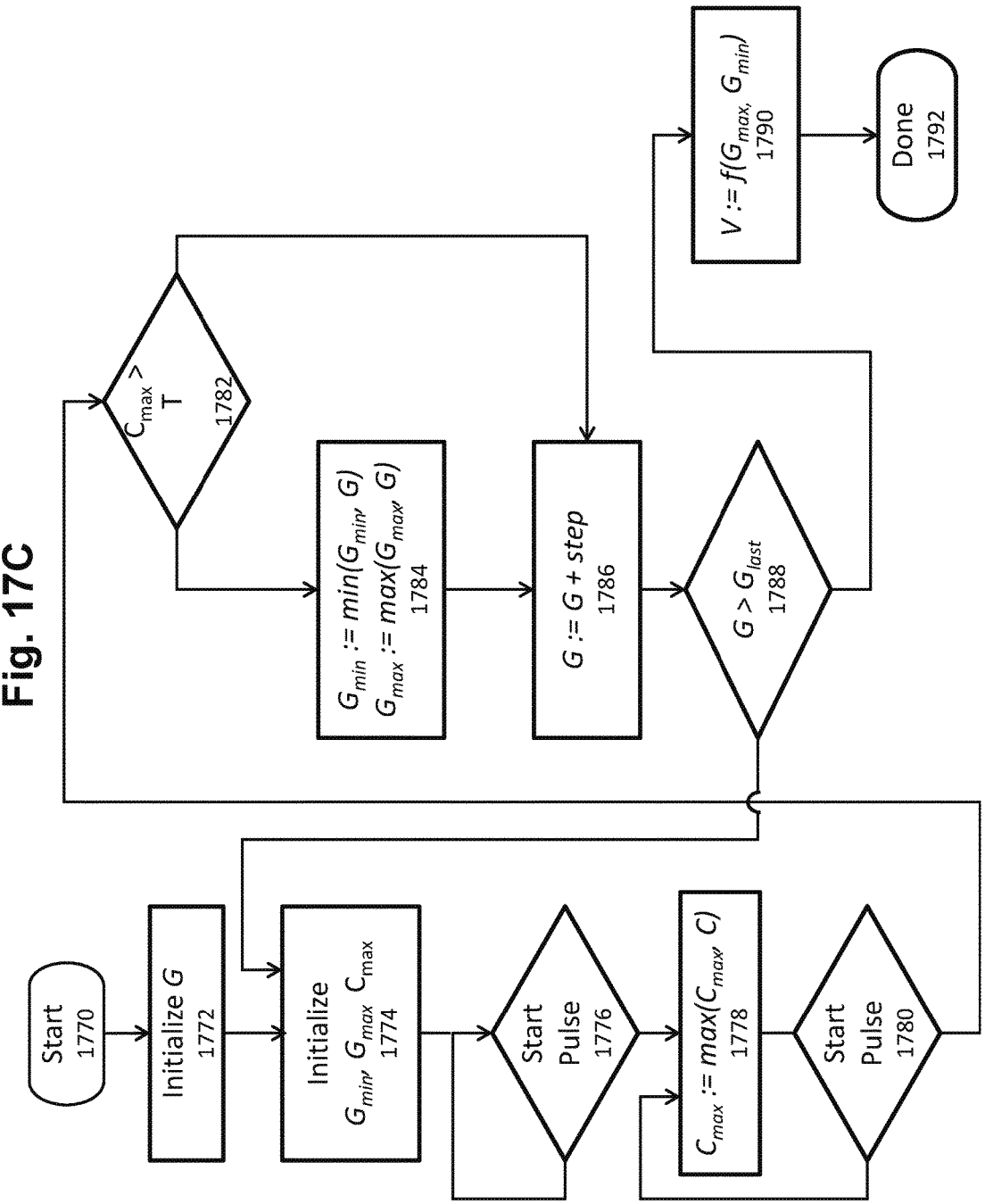
FIG. 17C is a flow chart representing an algorithm for determination of the gain setting of the input to the digital correlator of an embodiment of the invention.

A carefully designed digital correlator, fed from an excitation sequence generator, can detect a laser-generated optical signal deeply buried in noise and degraded due to absorption and scatter of the laser light. The receive-and-process system has a front-end gain control stage whose gain is controlled in steps until the correlator sees the excitation sequence bit stream or until the AGC amplifier reaches an upper limit. The controller 1700 in FIG. 17A will follow the process of FIG. 17C to determine the range over which the signal can be detected. Without loss of generality, but rather to facilitate understanding of the algorithm used, the following variables are used: G is the gain of the amplifier or the voltage of the reference signal used as input to the comparator 1720. C is the count of matching correlation elements. It is the output of the binary adder 1735. $C_{max}$ is the largest value of C observed between two start pulses; therefore, it is the level of highest correlation during one excitation sequence. T is the threshold value of C that is chosen to represent a high likelihood that the transmitted signal has been detected. $G_{min}$ is the smallest value of G for which a value of $C_{max}$>T has been observed. $G_{max}$ is the largest value of G for which a value of $C_{max} \geq T$ has been observed. V is the numerical value of the measured output and is produced by a function $f$, for example but not limited to the average, of the two measured values, $G_{min}$ and $G_{max}$. Following this notation, the algorithm starts 1770 initializing G 1772 to its lowest value and proceeding to initializing $G_{min}$, $G_{max}$, and $C_{max}$ 1774 to maximum, minimum, and minimum values respectively. Once initialized, the algorithm waits for a start pulse 1776. After a start pulse has occurred, the algorithm observes the value of C, recording the maximum value of the value of C observed before the next start pulse 1780 is observed.

After the start pulse 1780 is observed, $C_{max}$ is compared to the threshold T 1782. If $C_{max}$>T, then $G_{min}$ and $G_{max}$ are updated with $G_{min}$:=min($G_{min}$, G) and $G_{max}$:=max($G_{max}$, G) 1784. G is then increased by a step 1786, and then tested against the last value for G. 1788. If G is not greater than the last value of G, the process continues from 1774. If the last value of G has been evaluated, then the algorithm calculates V as a function of $G_{min}$ and $G_{max}$ 1790, and ends 1792.

The value V of the detected signal can be used to determine the value of the parameters to be measured, by, for instance but not limited to, a matrix multiplication of the measured values and a reference matrix. The matrix multiplication can be performed by means well understood using an electronic processor. Additionally, with reference to FIG. 19, a set of measured values can be fed as binary-coded input 1900 values into an array of multiplier circuits 1920, with outputs 1930, which feed to adders 1940, one for each output 1950 corresponding to a calculated property. Using structures of this form or similar compositions, a fixed circuit can be composed in a non-programmable structure to calculate the numerical value of a property to be measured. The removal of separate non-linearities can also be performed, by at least one of table lookup, range rescaling, limit alerts, and gain adjustment techniques as described related to FIG. 17A at element 1900. This conversion element is usefully included when the range of use of the inputs exercise non-linearities in the measurement path.

Figure 19:
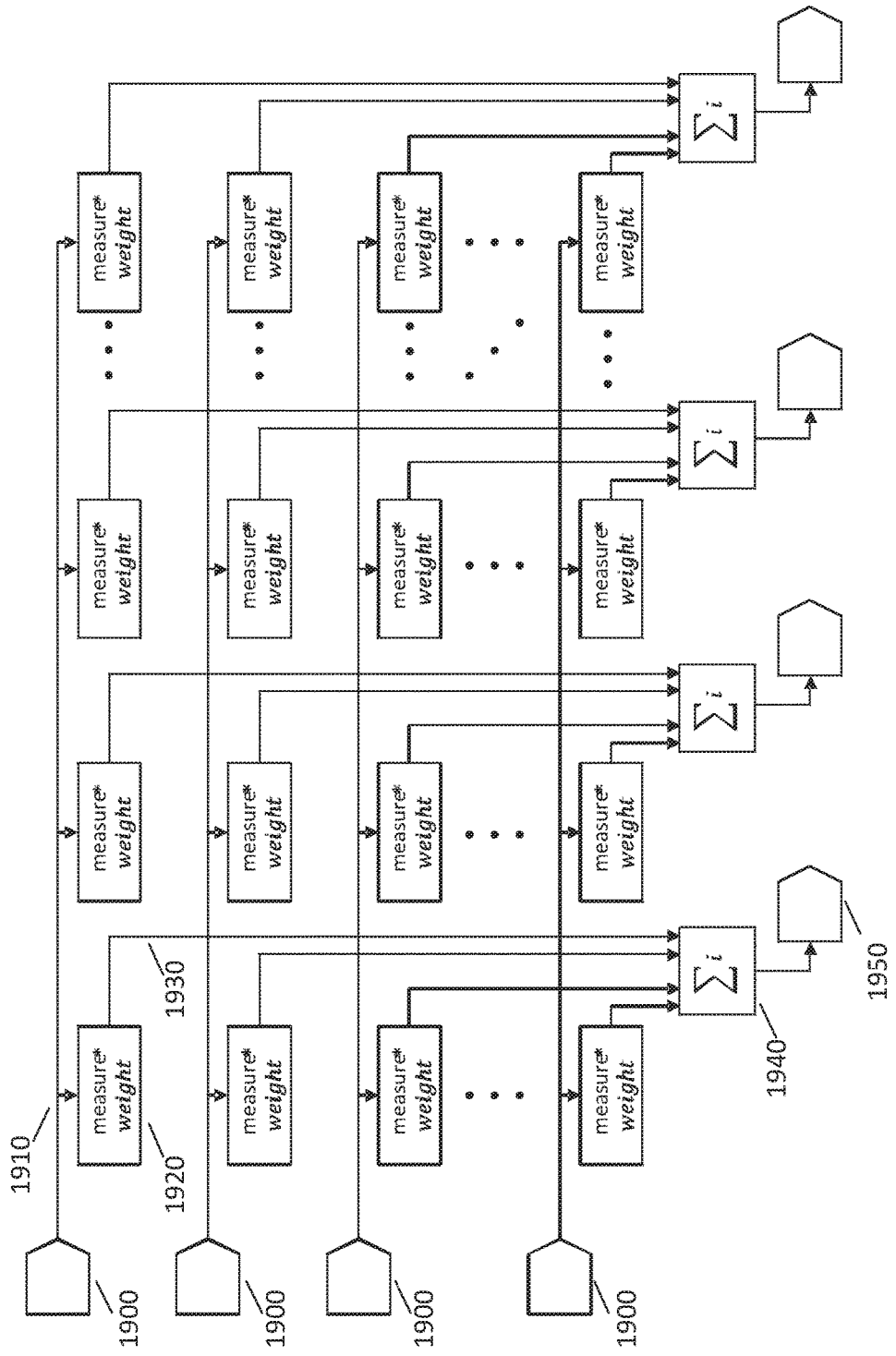
FIG. 19 is a diagram depicting an embodiment of a non-programmable processing element for producing numeric measured property values.

In order to quantify the results, the attenuation of the received signal should be initially measured. Such measurement includes transmitting an excitation sequence, receiving the attenuated sequence, and correlating the received values in time. A device, such as that shown in FIG. 11, is used for such a purpose. Once the attenuation of the received signal is derived, then equations 37c and 37d, for instance, can be used to calculate the concentration of a property in the material component. The apparatus shown in FIG. 19 is an appropriate circuit for performing such mathematical operations assuming the measure times the weighting coefficient and the summation are stateful operations (i.e., values from prior time slices are available to perform calculations). The "weights" in these calculations refer to wave properties such as the optical paths (or traversed distances) and extinction coefficients. Other fixed circuits, such as systolic arrays would also be appropriate to perform such calculations. Depending on real-time constraints and speed of processing, programmable processors such as those used for digital-signal-processing (DSP) or even general-purpose processors may also perform the necessary calculations.

In addition to equations 37c and 37d, it is understood that the introduction of bias and noise (see equation 8) to the calculations is typically required to attain quantifiable (versus relative or qualitative) results. Calibration operations, for example, are one means of deriving the values to be used for bias and noise.

The method to correlate a received signal with a transmitted signal provides for determining the delay in time between the two and thereby the delay from transmitting to receiving is a known quantity. Additionally, connections from the transmitters to the receiver, such as the connection 965 in FIGS. 9B and 9C, may be used for synchronization. As a result, the delta in time between signals received from two or more transmitters is also a known quantity and the signals can thereby be correlated in time.

Figure 17D:
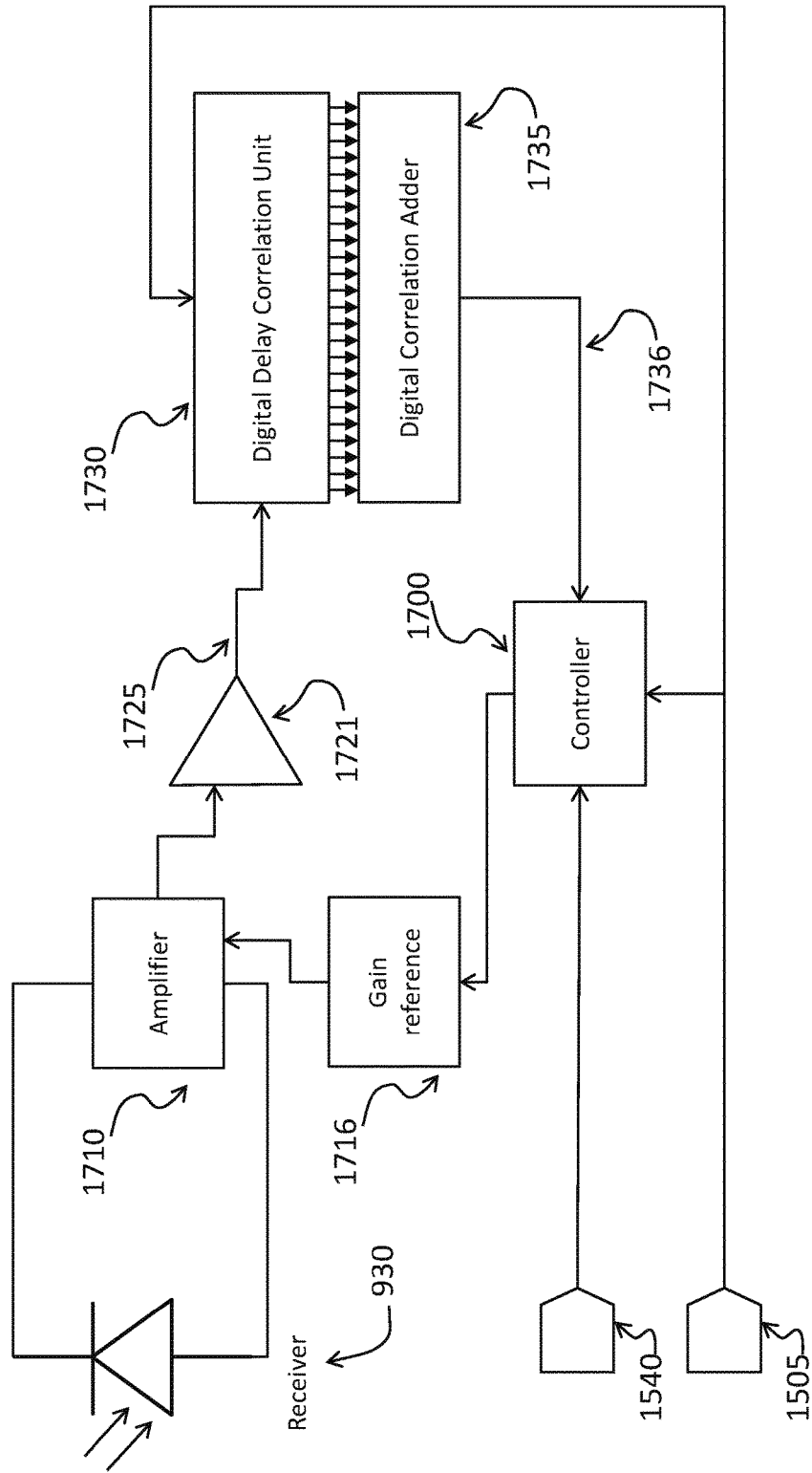
FIG. 17D is a diagram representing an N-bit digital correlator for use with a receiver of an embodiment of the invention.

N-bit Digital Correlator. While very applicable to a pulse oximeter (and providing for compact and low power implementation, and thus so advantageous in use), the embodiment described above with a binary comparison has given up much of the processing SNR gain made possible by the use of long excitation sequences. This is due to the single point of discrimination between ones and zeros at the comparator 1720. For many spectrometry applications, providing additional signal discrimination is useful. With reference to alternative FIG. 17D, similar to FIG. 17A with two significant changes, an N-bit digital correlator is shown. The comparator 1720 has been replaced with an N-bit analog to digital converter (ADC) 1721. The amplifier now optionally takes an input for gain from the gain reference block 1716.

Figure 17E:
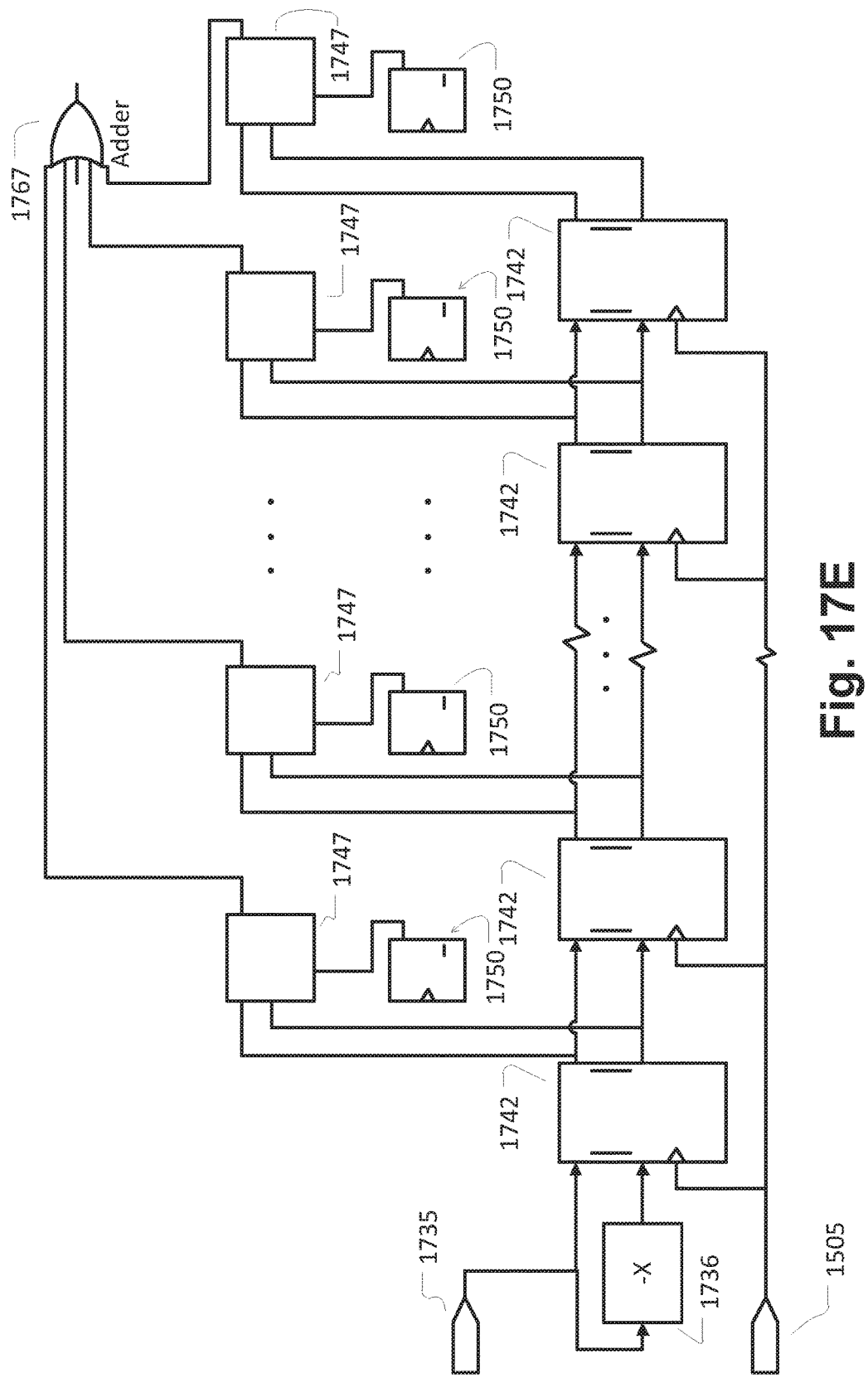
FIG. 17E is a diagram of electronic circuitry associated with the N-bit digital correlator of FIG. 17D.

With reference to FIG. 17E, the N-bit wide output of the ADC 1721 is used as input 1735 to the first 2 times N-bit wide delay line register 1742. The input is fed to N of the bits of the register 1742; the input 1735 is also fed to a negation block 1736. The output of the negation block 1736 feeds the other N bits of the delay line register. Based on the clock pulses 1505, the values in one delay line register 1742 feed the next register such that a value from one point in time will pass from one register to the next and on to the end with a step made during each clock pulse.

Responsive to the excitation sequence register bits 1750, N bits of the output of the delay line registers are chosen by each multiplexor 1747. The excitation sequence register bit set to one will select the time-delayed value of the ADC, a zero bit in the excitation sequence register bit will select the negated time-delayed value. In any given time cycle, the outputs of all of the multiplexers will be added together at 1767 to create the output for the controller. If the excitation sequence stored is M bits long, then the sum of the outputs 1747 will be $\log_2$ (M)+N bits wide if no bits from the least significant end of the numeric bus are dropped.

It is appreciated that, without loss of generality, the negation block 1736 can be placed in the data path after each delay line register 1742, and the delay line register can then have a collapsed width of N-bits rather than 2-N bits. Additionally other rearrangements of the topology of operations that accomplish the same goals can be applied. This principle is demonstrated below in the analog embodiments and in the hybrid embodiment.

Analog Delay Line Correlator-A. If it is desired to carry out quantitative spectrometry, a measure of the optical path length of the radiation in the tissue is needed. Since, in, for example, making measurements of samples of the human body the path length can be as short as 2-3 cm, and since light will travel in a turbid medium at perhaps 0.2-0.3 times the speed of light in a vacuum (or on the order of 200-500 ps/inch), very fine time resolution, in the range of 5-10 ps, is needed to resolve the optical path length with sufficient accuracy to be useful (see the discussion elsewhere in this document as to why a measure of optical path length yields an absolute-reading oximetry value rather than a relative value). Several embodiments of a receive-and-correlation processing chain have been identified, as described herein.

Figure 18A:
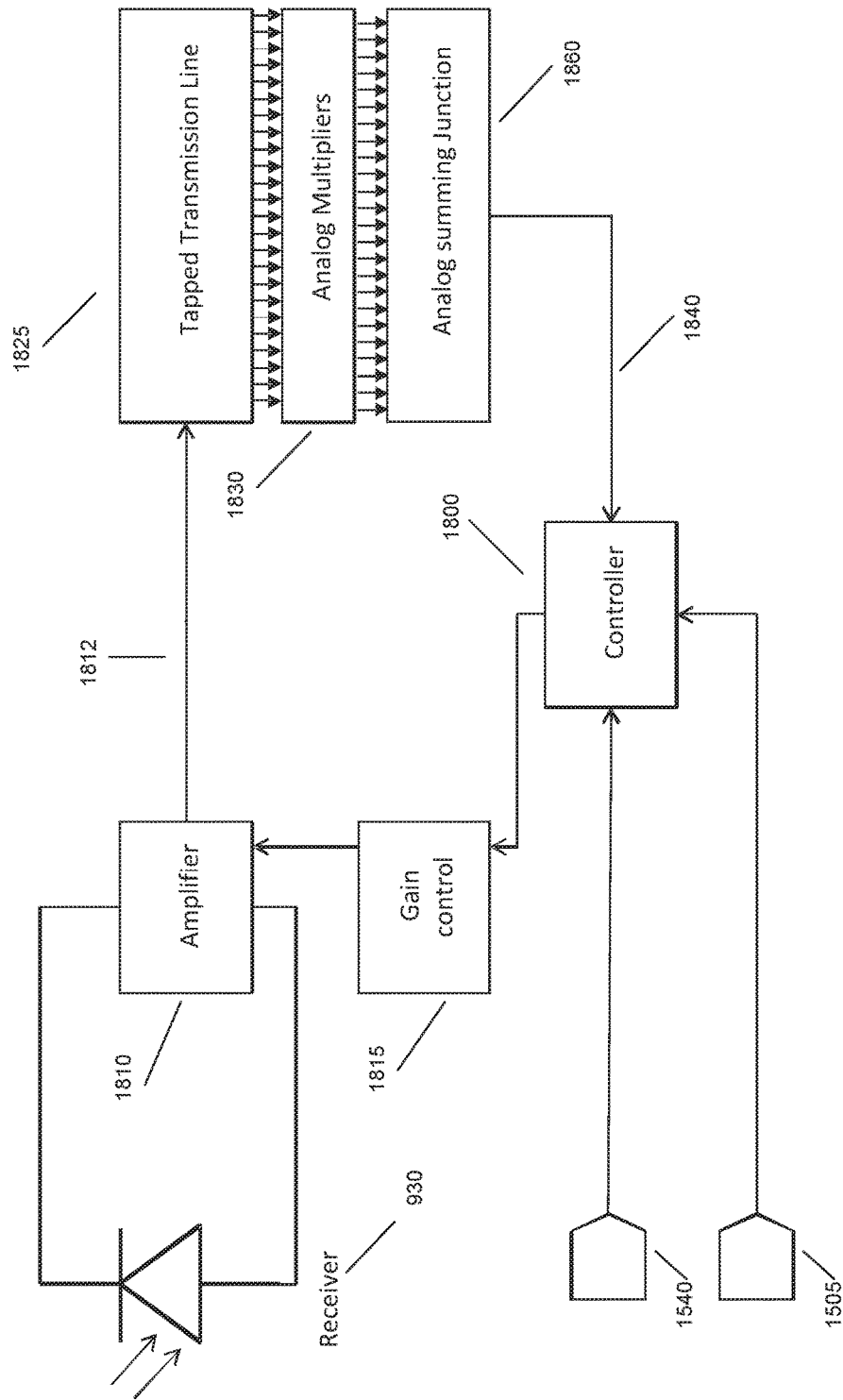
FIG. 18A is a diagram of a system employing an analog delay line as part of the correlator.
Figure 18B:
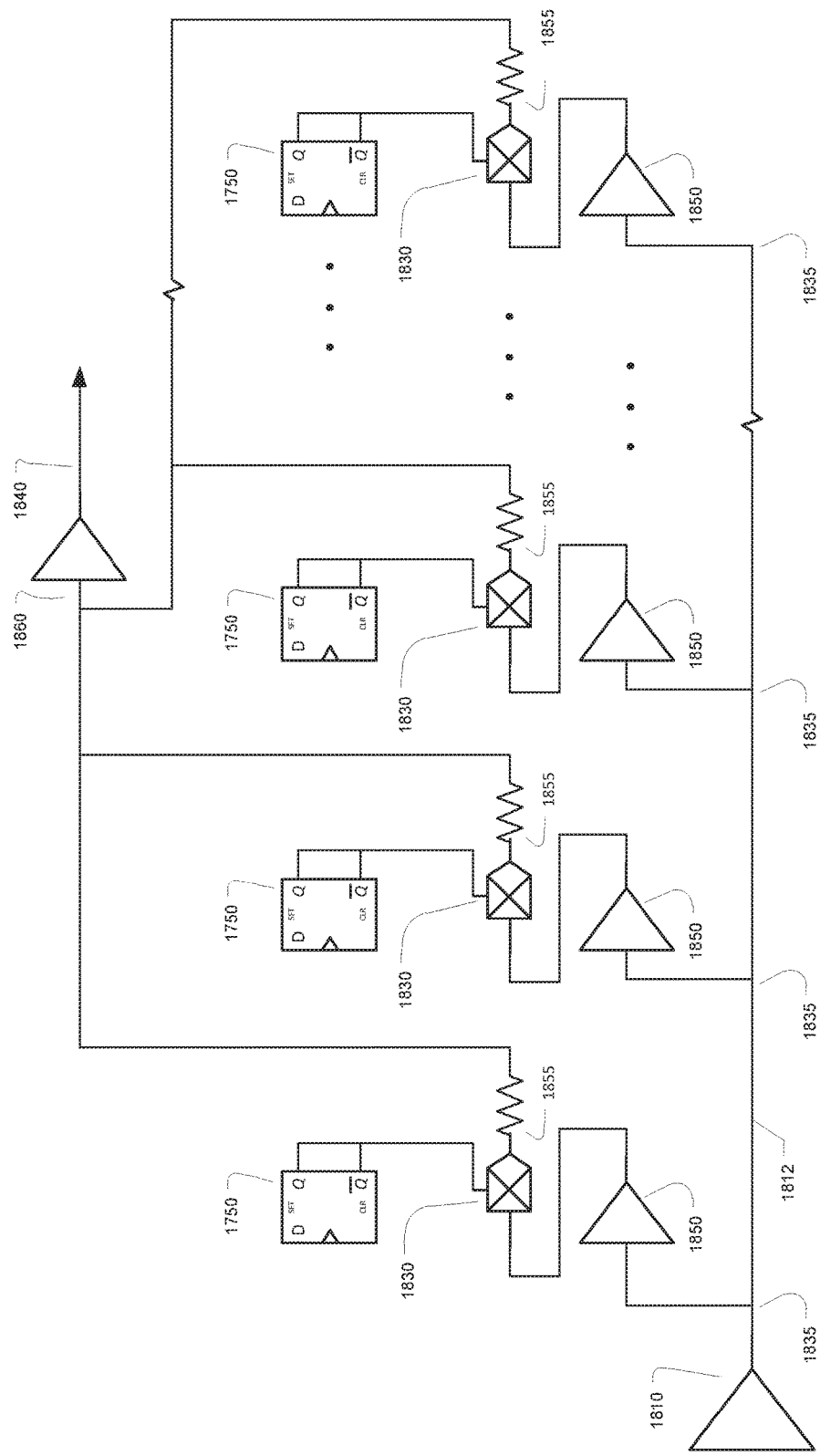
FIG. 18B is a diagram representing electronic circuitry of the analog delay line of FIG. 18A.

With reference to FIG. 18A and FIG. 18B, the embodiments are based on the concept of a traveling-wave amplifier, a concept that has been known and practiced at least since the 1950s for various high-power amplifiers, e.g., satellite communications systems, but has not been applied in either the context (spectrometry) nor in the structure (varying the inputs to the various sub-elements in two distinct ways) as described herein. The design of the traveling wave amplifier is herein altered considerably, to such an extent that the design is only "akin" to a traveling wave amplifier, but is not actually one. In a classical traveling wave amplifier, the analog input signal is propagated, or "travels," along a transmission line that is "tapped" at regular intervals, with the "tap" feeding the inputs of a successive chain of discrete amplifiers. As the analog signal propagates along the "feed" transmission line, the voltage variations of the input wave are used to drive the input of each successive amplifier, which in turn injects a "slug" of current into a second "output" transmission line. Thus, the signal in the output transmission line is amplified by the individual amplifiers through the superposition principle, such that at the end of the output transmission line a strongly amplified copy of the input signal emerges. This is the explanation of a conventional traveling wave amplifier. Regarding the present invention, the design changes to the traditional amplifier are described below, which novel modifications make the concept work as an "analog correlator," in contradistinction to the "digital correlator" described previously. The need for this design is driven by a requirement for a high level of timing accuracy with respect to the occurrence of the excitation sequence pattern at the receive chain, in comparison to when the excitation sequence was transmitted, that will yield a measure of optical path length in the tissue.

A correlator based on analog signal processing can be developed as a modification to, and extension of, a traveling wave amplifier. With reference to FIG. 18A, the optical pulse train is converted by an amplifier 1810 to a time-varying analog signal 1812 representing the optical pulse train, which is then propagated down an input transmission line 1825, which in turn is "tapped" at regular intervals, with the time-varying voltages at each "tap" fed into one input of an analog amplifier 1830. The analog amplifier in combination with the excitation sequence register bit 1750 and the multiplier 1830 implements the same circuit function as in the digital correlator, i.e., XNOR 1745 or multiplexor 1750. The time-varying output current from each analog multiplier 1855 is fed into a current summing junction 1860, and the output of the current summing junction 1840 will only have a maximum nonzero value if the stored and propagating excitation sequence codes line up one-for-one at some point as the excitation sequence pattern propagates down the input transmission line. In the embodiment shown in FIG. 18A, the controller 1800 provides input to the gain control 1815 of the amplifier 1810. The second input to the multiplier is the excitation sequence register bit 1750.

With reference to FIG. 18B, the incoming analog excitation sequence pulse train amplified 1810 and allowed to propagate down the input transmission line 1812 (as described above). As each pulse in the excitation sequence passes an amplifier 1850 and multiplier 1830, that amplifier generates a slug of current that is fed by the multiplier output into a current summing junction, optionally through a resistor 1855, or into one of a set of current summing junctions. This choice is a practical question of the particular technology used for implementation. If the summing junction has a large dynamic range, then fewer summing junctions will be needed and fewer cascade steps will be required. The summing junction sums all of the current slugs from every amplifier along the chain. Each amplifier/multiplier along the input transmission line in effect replicates in analog form the XNOR gate structure described for the digital correlator, such that matching "ones" and "zeros" between the stored pattern bits and the propagating excitation sequence bits statistically line up, zero-to-zero, and one-to-one. It is appreciated that the amplifier and multiplier shown can be combined in a variety of technologies using techniques known in the field.

Conversely, a one in the stored pattern aligned with a zero in the propagating wavefront, or a zero in the stored pattern aligned with a one in the propagating wavefront, will produce uncorrelated output amplitude from a given amplifier, contributing positive or negative contributions to the summing junction. On an instantaneous basis, the output from the summing junction will be higher or lower depending on how many zero-bits line up between the stored reference and the propagating waveform, and how many one-bits line up in the same manner. Since this is an analog circuit, the maximum output from the summing junction will only occur when the propagating code bits line up with the stored code bits, at which time the output from the summing junction will be maximum.

Optical path length and hence propagation time is very important in the absolute reading oximeter, since optical path length enables the quantitative calculation of oxygen saturation. To achieve the time resolution needed for path lengths of only a few cm, time resolutions in the 10-20 ps range need to be achieved. In one embodiment, to accomplish this resolution, we use a reference length of electrical transmission line on the oximeter circuit board (such as, but not limited to, a length of stripline or microstrip), which contains both the lasers at one end, and the photodetector and analysis circuitry on the other end, designed with a known propagation delay; this is the "gold standard" delay. We then compare the gold standard delay with the measured delay from decoding the excitation sequence at the receiver end.

In the first embodiment of this reference approach, an electrical "start pulse" 1540 from FIG. 15A is generated by the same circuitry that drives the laser, and propagates down the reference delay line to the processing circuitry; the rising edge of the start pulse at the processing circuitry is used as a time reference against which the output of the analog correlator circuitry is compared. Because the propagation delay along the known length of the reference delay line is made short by controlling the material from which the circuit board is manufactured, the rising edge of the start pulse creates a "time zero" point in the analog correlator circuitry, such that the output of the analog correlator is with reference to the rising edge of the start pulse; and since the time duration of the delay line is known, the time difference between the arrival of the start pulse and the output of the correlator can be added to the known duration of the delay line. This then yields an accurate measurement of the actual optical path delay, and hence optical path length.

The analog correlator circuitry must employ very "fast" transistors, in the sense that they must exhibit very fast output rise times when exposed to very fast edge rates of an incoming signal. If the transistors cannot maintain the fast input rise times (and in fact if the rise times of the excitation sequence pulses are not rapid as well), then highly accurate time resolution of the system will be impossible to achieve. Fortunately, very fast rise time transistors are available from several modern integrated circuit technologies.

The analog correlator receives a "start pulse" which is transmitted down a reference delay line on the oximeter circuit board. Since the time delay of the reference delay line can be created at printed circuit board fabrication time and subsequently measured accurately with laboratory equipment, the delay is well characterized and can be arranged to be shorter (or longer) than the approximate optical path delay through the tissue. The start pulse is used to initiate the operation of the analog correlator, and then the identification time from the correlator can be added to the known delay time of the reference delay line. With the total propagation time of the optical path known, the physical path length can be determined accurately, which in turn can be employed in the oximetry equations to yield absolute oxygen saturation values. The correlator implementation must employ very fast transistors to preserve the fast excitation sequence pulse rise times. It is understood that several different implementations are feasible, one example of which is the operation of a very fast "clocked counter", which is "started" by the arrival of the reference signal from the delay line, and "stopped" by the pulse output of the correlator, such that the number of "counts" in the counter, when it is stopped, yields a direct time measure of the propagation delay of the probe light through the medium being measured.

As a beneficial enhancement of the analog correlator, rather than transmitting the start pulse, a duplicate of the analog correlator is feed directly from the excitation sequence generator. The two analog correlator circuits are operated in parallel. One of the correlator circuits processes the analog optical-to-electrical pulse train as described above. The second correlator processes the electrical excitation sequence pulse train that has arrived down the reference delay line. The excitation sequence holding registers in both correlators are loaded with the same excitation sequence pulse train. Thus, if a match occurs in one correlator, a match will occur in the other correlator as well. However, the two correlators will detect the match at slightly different times, because the propagation delay in the circuit board material can be designed to be shorter than the propagation of the optical signal in tissue. Thus, the measured delay in the reference line can be added to the difference in detection times between the two analog correlators, to create an estimate of the propagation delay, and hence the optical path length, in the tissue.

If it turns out that the optical path lengths at different wavelengths are substantially different from one another, a "training" cycle may be used for each wavelength. That is, before beginning an actual measurement cycle, it may be necessary for each wavelength to be "path length-calibrated" by passing the start pulse down the reference delay line while each individual VCSEL is transmitting its unique excitation sequence code; when all VCSELs have done so, and the individual path lengths have been measured and stored in the circuitry, then all VCSELs can begin transmitting for the purpose of making the material component species measurements.

Hybrid Correlator. With reference to FIG. 11, an embodiment is shown for determining the amplitude of the one or more wavelengths used to enable the comparison of the transmission and absorption of one or more single-wavelength light sources as the source illuminates a measurement subject. FIG. 11 presents the block structure of a mixed signal mechanism that can be used to collect this measurement. By adjusting the variable delay line 1160, the mechanism shown is able to take a sequence of measurements; each measurement corresponds to a particular delay of light through the measurement subject.

A coded data stream (zeros and ones) from the excitation sequence generator 1100 is used by the driver 1110 to modulate a light source 1120, in the preferred embodiment a VCSEL. The VCSEL is coupled to the measurement subject 1130 (the light shines on the skin), and a sensor 1140 (e.g. but not limited to a photo detector) detects the light and its output is amplified 1150, producing a time varying analog signal. The correlation function 955 is performed by multiplying this time varying signal 1170 by a time delayed version of the coded data stream. This multiplied signal is summed 1180 and the result captured at the output 1190 and processed in combination with other values produced by other time delays and the result of correlation with the excitation sequences used to modulate optional additional wavelengths of light.

The coded data stream takes two paths to the output; one is a simple time delay through the variable delay line 1160, and the other is an optical path through the material to be measured. The two paths are combined at the multiplier 1170. The multiplier 1170 is configured such that the 1's of the excitation sequence from the delay line 1160 cause the multiplier 1170 to pass the analog signal from the amplifier 1150 to the summing amplifier 1180. Alternately, 0's from the delay line cause the multiplier to invert the sign of the analog signal from the amplifier 1150 before passing that signal to the summing amplifier 1180. The result of this multiplication will be that the output 1190 of the summing amplifier 1180 will have the correlated parts of the analog signal amplified, and the uncorrelated parts of the analog signal will average over time toward zero.

Figure 12:
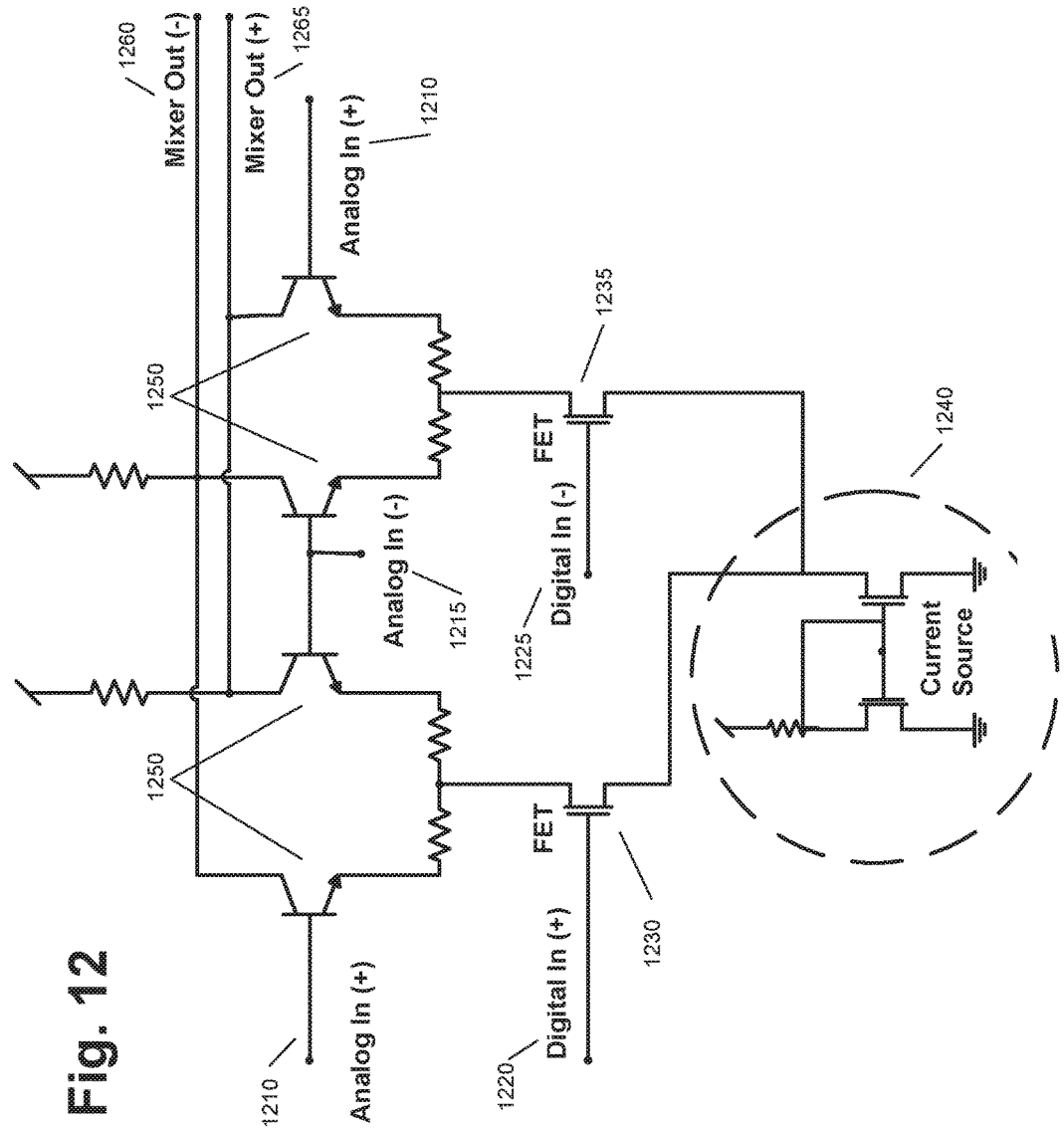
FIG. 12 is a diagram illustrating an analog and digital input mixer circuit suitable for use in the system shown in FIG. 11.

Referring to FIG. 12, a representative circuit to perform this multiplication is illustrated. A Gilbert cell multiplier using a combination of FETs 1230, 1235 and bipolar transistors 1250 for the digital/analog mixing is shown, with a differential analog input 1210, 1215, a digital input 1220 and the compliment of the digital input 1225, working together to produce, at the output 1260, 1265, a piecewise version or inverted version of the analog input.

The multiplier is configured so that 1's from the delay line will cause the multiplier to pass the analog signal from the amplifier to the summing amplifier, and 0's from the delay line will invert the sign of the analog signal from the amplifier before passing that signal to the summing amplifier.

It is useful, for comparison purposes, to produce a ratio of the correlated response of the system to a reference. Two references may be provided by versions of this invention. Using the switch to pass the signal or to ground the input of the VCSEL Driver circuit, when the switch is grounding the input, measurements may be taken while the VCSEL is driven at a constant brightness. Also usefully, the VCSEL Driver can be driven with a different excitation sequence input than the one used at the multiplier. This approach will drive the VCSEL with a time varying signal, but one that is not correlated to the detection circuit. This in turn will produce an output at the summing amplifier corresponding to noise reduced by the processing gain of the excitation sequence correlation.

When multiple values for the delay are used, one per measurement period, multiple measurements can be taken. The set of specific delay values used, combined with the corresponding measured output of the summing amplifier, provide a set of points that can be used to characterize the measurement subject. The impulse response of the optical leg of the measurement system can be roughly described as answering the question, "When a bundle of photons are released into the sample at time zero, how long does it take for them to reach the sensor?" While each photon takes a particular path through the sample, and emerges at only one time, there is a probability density function that can be used to predict the aggregate energy of the collection of photons at each of the likely transit times through the sample. Referring to FIG. 13, an example of this impulse response is shown. There is a ballistic transport delay associated with the geometric path length from time zero to the time the first photons appear at the sensor. No photons can reach the sensor before this minimum transit delay. There is a spike 1330 at the time associated with straight-line transit from emitter to sensor. The height of this spike relative to the rest of the energy observed is characteristic of the material sample and the coupling to the material. If the material is a homogeneous diffusor, the observed impulse appears as pictured, with paths distributed about a mean. For this example, a gamma-like distribution was chosen to represent the tissue response. Generally, however, the tissue response may be represented by a different distribution.

While plotting the impulse response is not a necessary step in evaluating the measurement subject, a plot of the values collected can show the correspondence between those values with the characteristic impulse response (i.e., point spread function) of the measurement subject.

As shown in FIG. 14, if the impulse response of the material is similar to that shown in FIG. 13, the measured points corresponding to the various delay line settings will lie upon the impulse response.

Based on the multiple relatively orthogonal coding sequences described elsewhere, the sensor output can be processed simultaneously by multiple mixers to produce the measurement value for each input wavelength. Being able to run these measurements simultaneously can advantageously eliminate motion-based inaccuracies when comparing multiple wavelengths.

In a heterogeneous measurement sample, the impulse response may not be a simple Gamma function. The longer the delay, the deeper the penetration of the photons into a sample. Because the makeup of the sample may vary with depth, obtaining the relative absorption of multiple wavelengths over a range of depths provides an advantage in characterizing the measurement sample.

Multiple mixers/correlators, each fed with the time delayed excitation sequence input of a reference from a VCSEL driver input, can be run simultaneously to obtain ratios between wavelength extinction coefficients, thereby providing for material sample characterization. As shown in FIG. 14, where two impulse responses are shown, notionally for two different wavelengths, $A_1$ is the signal level measured for Wavelength 1 at delay A, and $A_2$ is the signal level measured for Wavelength 2 at delay A. In a similar fashion, $B_1$ and $B_2$ correspond to delay B, and $C_1$ and $C_2$ correspond to delay C. The two curves composed of the varied delays are not simply scaled versions of each other, but rather $$\frac{A_1}{B_1} \ne \frac{A_2}{B_2} \ne \frac{A_3}{B_3}. \tag{48}$$

The result of this is that the various component concentrations can be calculated to vary by path length.

Multiple mixers, each fed with a time delayed excitation sequence used as the input of a different VCSEL driver, can be run simultaneously to obtain ratios between wavelength extinction coefficients, with the delay used in the correlation providing multiple ratios, each corresponding to a notional "depth" in the measurement sample. This provides a set of selectable sites for measuring the variation of multiple properties.

Figure 20A:
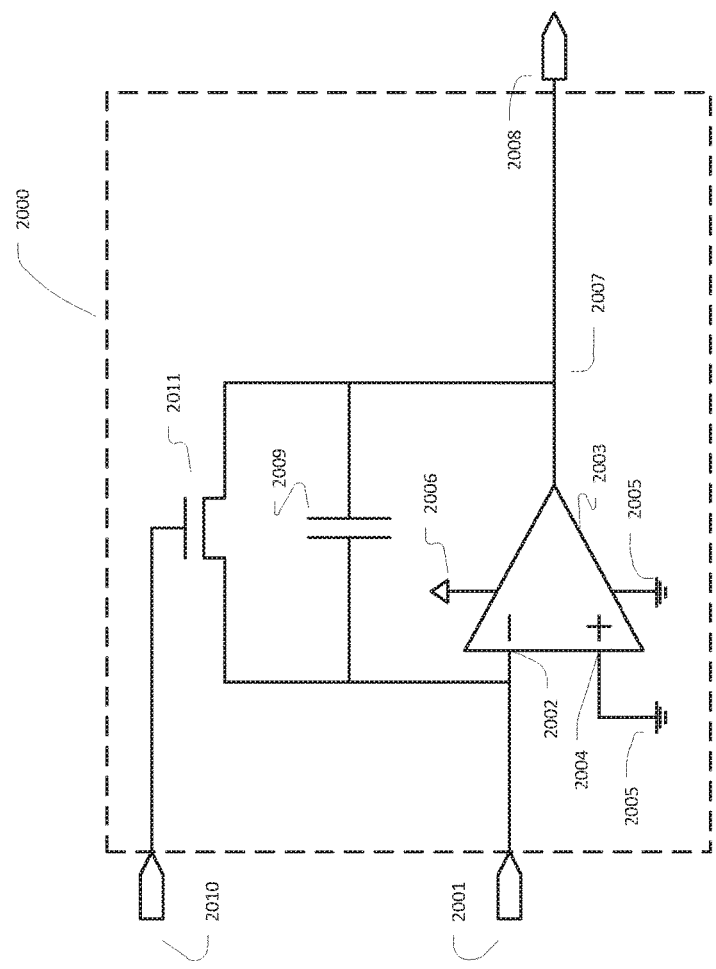
FIG. 20A is a diagram schematically illustrating an example resettable analog integrating amplifier.

Analog Delay Correlator-B. With reference to FIG. 20A, a resettable integrating amplifier 2000, alternately called a summing amplifier 1180 is shown as a schematic representation of an example implementation. The function of this component is to, with equal weight over time, collect the analog signal level of its input 2001, and provide the integrated value over time as output 2008. This integrated value is $$\text{Output}_{2008} = \int_{T_0}^{T_{RESET}} \text{Input}_{2001} dT. \tag{46}$$

The circuit is created using an operational amplifier 2003, connected to power 2006 and ground 2005 sources to provide energy for operation. Operational amplifiers have two inputs, an inverting input 2002 and a non-inverting input 2004. The input 2001 is connected to the inverting input 2002 of the operational amplifier 2003. The output of the operational amplifier 2007 feeds both the output 2008 of the integrating amplifier subsystem system 2000 as well as terminals on the feedback capacitor 2009 and the source/drain of reset field effect transistor (FET) 2011. The other terminal of the feedback capacitor 2009 and the drain/source of reset field effect transistor (FET) 2011 are connected to the inverting input 2002 of the operational amplifier 2003. When the RESET pin 2010 is not asserted, the feedback capacitor isolates the operational amplifier input from the output and stores an integrating charge, providing the integrating function over time. When the reset input 2010 is asserted, the FET 2011 conducts allowing the feedback capacitor 2009 to quickly discharge. The output 2007 of the operational amplifier 2003 and both terminals of the feedback capacitor, take on the instantaneous voltage level of the input terminal 2001. The integrating amplifier subsystem 2000 is used in the schematic in FIG. 20B as part of the analog delay correlator-B.

In this circuit, differentiated from the solution described related to FIGS. 18A and 18B, rather than having a series of delays 1812 in the analog received signal 1810, instead, in this implementation, the input signal 2016 is replicated with balanced connections that provide the same delay 2015 and is fed simultaneously to each buffer 2020 such that a timing-identical copy of the input 2016 is presented to each multiplier 2025. Said multipliers may be implemented as the example Gilbert mixer of FIG. 12 with buffer 2020 output as the analog input 1210 in mixer circuit 2025. Other mixers and multipliers known in the art may be used. The digital input of the multiplier 2025 is derived from the reference signal which is a precisely time imaged version of the signal produced by the excitation sequence series of pulses. This signal is the input at buffer 2030, and is distributed to each of a multiplicity of multipliers through controllable time delay elements 2040. In the figure, these time delay elements are shown connected in cascade form. The inputs to the time delay elements can alternately be connected in parallel or a combination of parallel and cascade. The advantage of using the cascaded delay for the excitation sequence is that the signal is a binary full swing signal that can be regenerated at each delay stage without injecting any additional noise into the signal derived at the output of the multiplier 2026. The excitation sequence series of pulses serving as reference for each group of elements is time delayed such that it corresponds to a desired point in the impulse response for each group. The result of this series or collection of measurements is what is represented in the impulse response graphs shown in FIGS. 8C, D and E, FIG. 13, FIG. 14, FIGS. 24A and B, and FIG. 28. The production of this value is performed for a single time point along the full impulse response curve by the circuit illustrated in FIG. 11, based on the setting of the variable delay line.

Each multiplier output 2026 is the input to the resettable integrating amplifier 2000. The output of the integrating amplifier 2050 provides the input to the analog to digital converter (A/D) 2055. The reset input 2010 and the sample input indicated by the clock triangle on the analog to digital converter 2055 are operated to sample the extracted correlated signal level, convert the value to digital form 2060, and latch the value in the output register 2070, responsive to a clock signal feed to the data latch 2070. The value latched in register 2070 is a surrogate for the inverse of the attenuation, that is, it is the received signal strength. The value latched in the register may be read and averaged over time to provide more precision of measurement, as the noise from the quantification, the noise for the system, and if the excitation sequence is sufficiently long, the correlation noise continues to be reduced. For this reason, an implementation of the present invention uses an A/D with fewer bits of precision than are achieved in the end, and very long excitation sequences, sampling the received signal strength multiple times during the course of the excitation sequence, thereby increasing the available SNR beyond the range of the A/D. The full correlator subsystem 2075 can be incorporated into the larger system shown in FIG. 21.

Figure 20B:
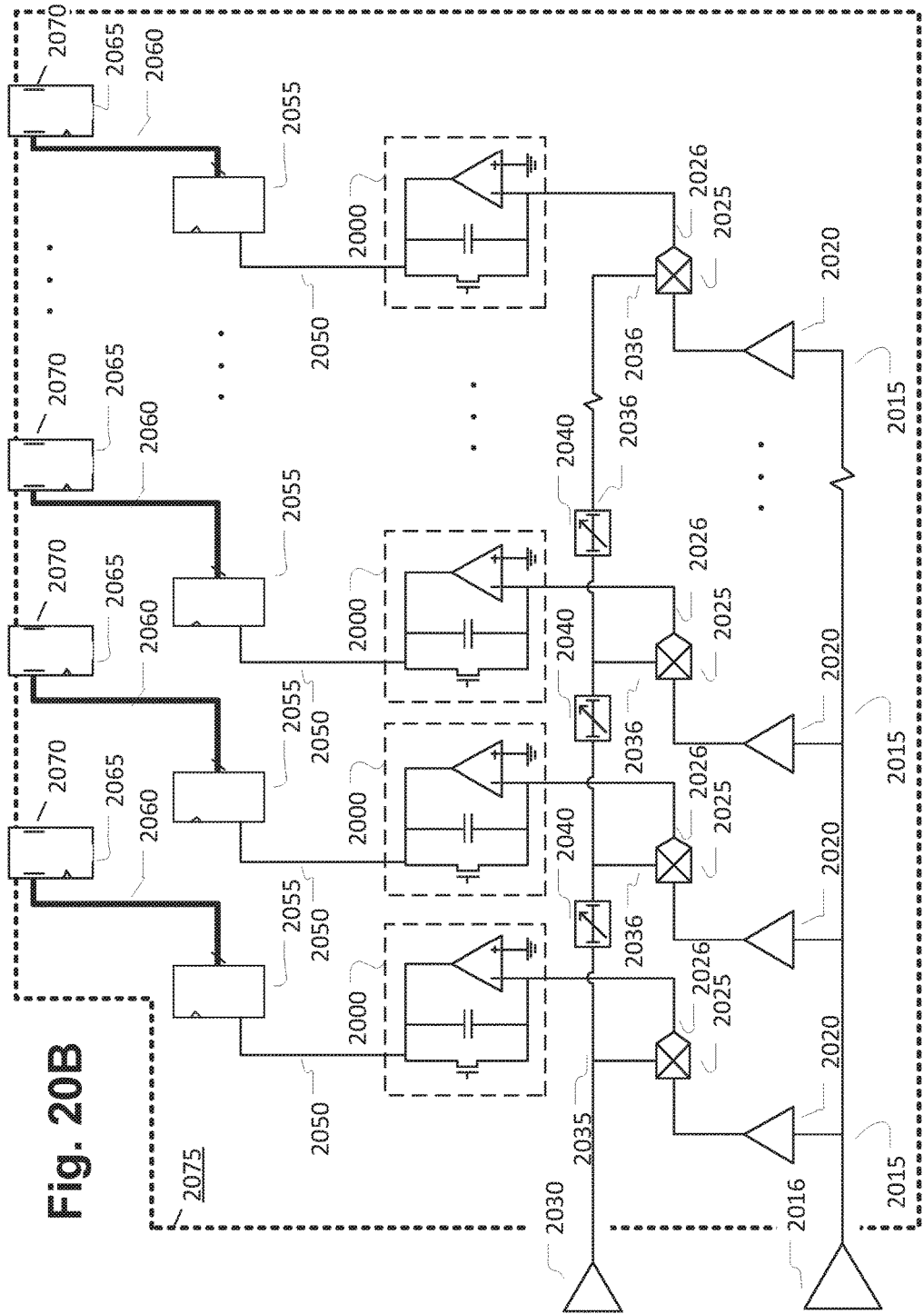
FIG. 20B is a diagram schematically illustrating a traveling-wave-like parallel implementation to produce key values of the impulse response in output registers.

Referring to FIG. 20C, the relative timing of the control signals that are used to compose the apparatus of FIG. 20B into a system are described. The control signals include the integrator reset input 2010, the A/D sample clock on latches 2055, and the data register latch clock of 2070. These are shown in the relative timing diagram of FIG. 20C. The timing traces from top to bottom are the A/D sample clock 2056 and the data register latch clock 2071, and the excitation sequence repetition period are shown. Using time as the x-axis, the positive going edge of the control signal is designated as the time that the event is triggered. The width of the triggering pulse is dependent on the particular technology chosen. Following design practice that include validation of set-up and hold times is required and assumed. The "S" curves, for example, the one going from the pulse on timing arc 2056 to the pulse on timing arc 2071, are used to indicate that the trigger as the beginning of the arrow must be complete before the next event, the trigger at the end of the arrow. For example, the A/D sample 2056 must be complete before the integrating amplifier 2011 is reset, or the data at the output of the A/D is latched 2071. The data at the output of the A/D must be latched 2071, before the integrating amplifier 2011 is reset. In one embodiment, the sequence of triggering multiple channels of attenuation measurement are concurrent, and are triggered from the transmitter indicating the start and end of excitation sequences of known and complete statistics 2080, that is, that the signal is balanced such that the 'chip' to 'chip' interference in the impulse response accumulation is canceled out. Time period 2081 encompasses the sequence needed to capture data from the correlating subsystem. This sequence is repeated during the period indicated by 2083. In the intervening time represented by the ellipsis of 2082, this sequence can be repeated many times to improve the accuracy of the measurements. The full duration of the measurement, including the repetitions of 2082, are advantageously encompassed by a set of excitation sequences that do not repeat over the period 2084 plus the period 2085.

System Composed of Multiple Correlators

Figure 21:
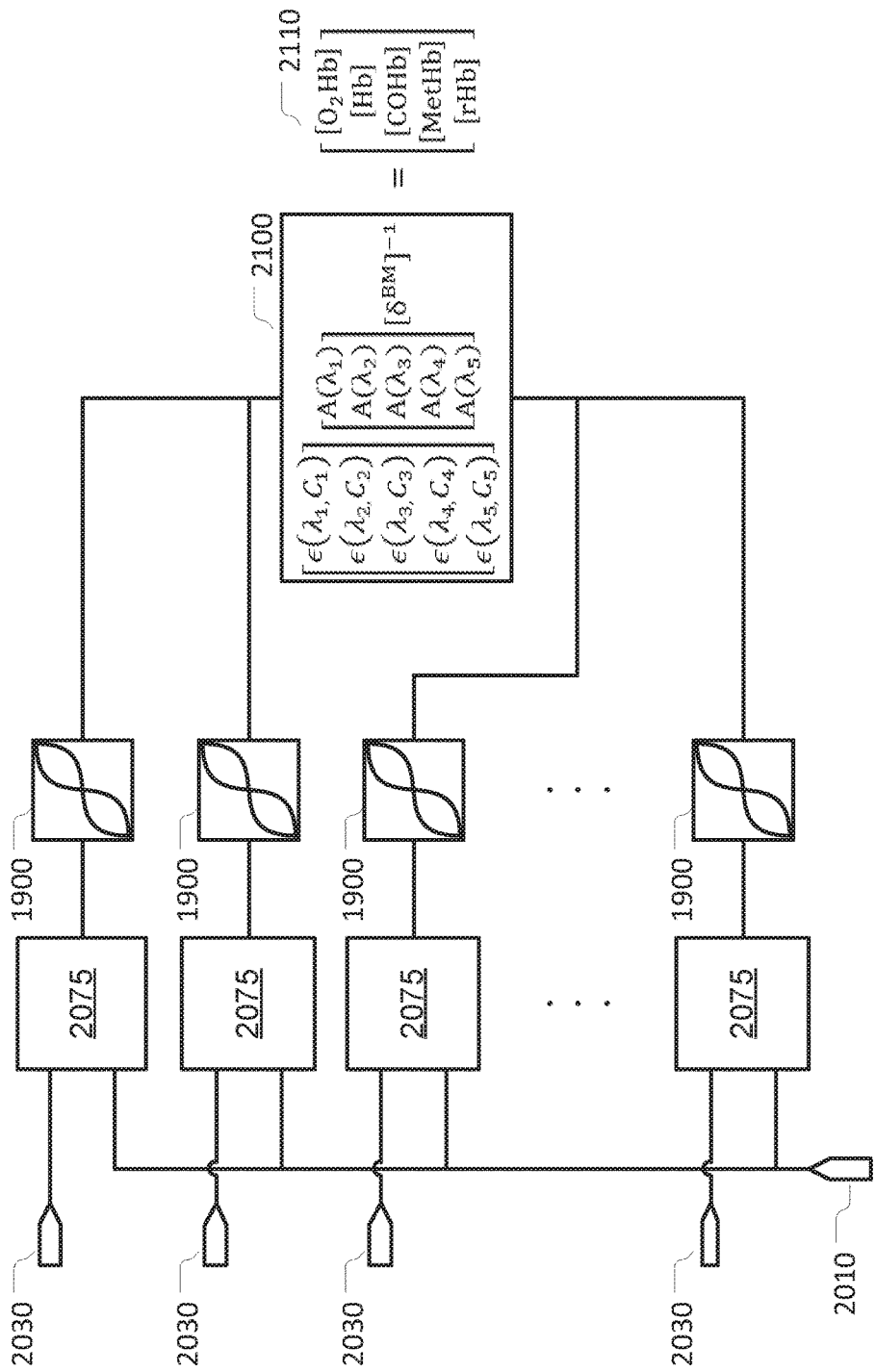
FIG. 21 is a diagram of a system for determining the concentration of material components based on the received signal stream and time accurate representations of the various excitation sequences.

With reference to FIG. 21, in one embodiment, a collection of the correlators 2075 is arrayed sharing the received signal 2016. Each sub-system however has the excitation sequence reference corresponding to the propagation amplitude that it will quantify. The inputs 2030 each are unique for the correlating subsystem 2075. As described in FIG. 19, the output of the correlator may have residual non-linearities. Element 1900 in this figure provides a digital mapping function to restore relative linearity to the collection of $A(\lambda_i)$ to the matrix system 2100. The result is an output of the concentration levels of the material components 2120 for which the system has been designed.

Multi-Dimensional Measurements

The techniques disclosed herein are not strictly limited to single-point or one-dimensional measurements. Rather, by altering the modulation scheme, additional information about the measurement as a function of tissue depth and distance between the light source and the detector is possible, thereby resulting in a two-dimensional measurement. Extending this concept by employing a grid or array of emitters and detectors can provide truly 3D measurements of tissue characteristics. Acquiring results of the measurements at different points in time (e.g. through the heart cycle or as a function of an appropriate signal-modulation scheme), adds a temporal component to the measurement, in turn resulting in a 4D measurement (three spatial dimensions and time). Carrying the measurement at multiple wavelengths provides an additional fifth, spectral dimension. The extension from one dimensional physiological monitoring to five dimensions of monitoring greatly enhances the capabilities and reach of embodiments of the invention presented in this disclosure. Applications of the disclosed embodiments include important and still unresolved clinical problems such as, e.g., oral cancers that can be identified when stimulated with light having appropriately chosen spectrum, or abnormal protein buildup in utero that can be noninvasively monitored by means of optical techniques.

Embodiments of the present invention provide a method for transmitting, receiving, and quantifying two or more concurrent signals. The method includes transmitting a first signal in response to a first excitation sequence, at a first wavelength and from a first location while transmitting a second signal concurrent to the transmission of said first signal, in response to a second excitation sequence, at a second wavelength and from a second location. The method additionally includes receiving the transmitted signals as an aggregated signal; and processing the aggregated signal by correlating it with a time-controlled representation of the first excitation sequence and, additionally or in the alternative, by correlating the aggregated signal with a time-controlled representation of the second excitation sequence. The quantified result(s) of each of the first and second correlations provides measure(s) of, for example, attenuation and scattering of the first and second signals through the media of propagation. The media may include, for example, at least one of turbid media, molecular dye, an organism, and similar spectrally distinguishable material.

A system of the invention is then used to determine media-characterizing property values based on relative and absolute results of the magnitude of the received signal components (such as variations over time). The media-characterizing parameters include, for example, hemoglobin analyte concentrations, blood glucose level, blood protein level, blood lipid level, total body water, central blood volume, heart rate, heart rate variation, concentration of a fluorescent biomolecule, and concentration of a fluorescent dye.

Useful variations of the composition of the excitation sequences include time periods of silence, possibly with the arrangement of the silent periods such that a received signal can be calibrated in the absence of any other system excitation, the repeating duration of the various excitation sequences may be different, the excitation sequences may beneficially comprise codes substantially balanced in duration between maximum and minimum energy, the excitation codes may be based on pseudo-random repeating sequences, the excitation sequences can be based on actual random processes, the excitation sequences can be produced from stored sequences. The excitation sequences of the multiple channels are beneficially relatively orthogonal, that is, the long-term correlation of one of the excitation signals with another excitation signal will not be substantially different from correlation to the background noise of the system. If the excitation sequences are produced with a repeating pattern, it may be beneficial to provide a longer baseline for noise reduction by using different pattern lengths or durations. Durations that are relatively prime one to another will produce longer independent sequences, thereby reducing any cross-induced noise from the received and correlated result. If an excitation sequence is produced digitally by a clocked process, that is, the sequence can be represented by a sequence comprising a fixed set of levels, with the output level changing at time periods which are a multiple of a clock signal on a fixed time base, the changes in level of the excitation sequence can be separated in time by at least the nominal impulse response time of the sample being measured; however with the mixing and correlation techniques described herein, the time period separating changes in level of the excitation sequence can also be substantially shorter than the nominal impulse response time of the sample being measured and still provide accurate quantification of properties of the sample being measured.

The transmitter or the receiver, or both may be juxtaposed to a sample to be characterized; said sample altering the signal between the transmitter and the receiver. The signal in transit may be altered by at least one of turbid media, molecular dye, an organism, and similar spectrally distinguishable material. The time-controlled representation of the excitation sequence may be produced responsive to the excitation sequence passed through a variable delay element. This method may be used in a system where the receive processing includes scanning the delay or adjusting the delay element over an interval—thereby providing a representation of the impulse response of the intervening material. The delay element can also be set at a determined delay to correspond to the measurement of interest. The setting of the delay elements can be accomplished in a manner that synchronizes the delay used for each correlation process, or the time-controlled delays of the multiple correlation processes may be scanned or set independent from each other. Alternately, an array of similarly constructed multipliers and integrators can be connected, each to a varied delay of the excitation signal. In this case, multiple values of the impulse response can be produced concurrently. The transmitting device may usefully be, for example, an antenna, a laser, a VCSEL, an LED, or similar device. The detector of the receiver may usefully be, for example, an antenna, a PIN diode, an avalanche photo diode, a photo multiplier tube, or similar device. The correlator may usefully include, for example, a mixer followed by a summing amplifier, followed by an analog to digital converter; a set of delay elements interconnected with a representation of the excitation sequences, a low-pass filter, an analog-to-digital converter, and a threshold detector and counter; analog delay line correlator; or similar circuits. The logical unit for processing the aggregated signal correlator may usefully include, for example, a programmable device, a device programmed with software, a fixed (non-programmable) logic unit, an analog circuit element, or combination of such elements.

Embodiments of the present invention may include an apparatus comprising: two or more transmitters, each transmitting its signal in response to an excitation sequence, at a unique wavelength or from a distinct location; said transmission being made at times concurrent to the one or more other transmitters. Said apparatus also comprising a receiver for receiving some or all transmitted signals as an aggregated signal; and a logical unit for processing the received aggregated signal, whereas: a distinct correlator is used for quantifying the received portion responsive to each transmitted signal; said aggregated signal is correlated with a time-controlled copy of the excitation sequence to generate a data sequence; and the data sequence is quantified uniquely corresponding to the transmitted signal of interest. The time-controlled representation of the excitation sequence can alternately be produced by passing the original excitation sequence through a calibrated time delay element, such as tapped delay line or other similar technique, or it may be created independently at the receiver, based on a calibration pulse received from the transmitter assembly.

Making Use of the Fine-Grained Impulse Response

Making use of the fine-grained impulse response provides increased fidelity of measurement in several systems. In addition to the multi-transmitter, multi-receiver, and micro-mirror-based localization control techniques, an embodiment of the current invention includes using information about the time delay (and hence radiation path length) contained in the fine-grained impulse response to increase the precision of spatial localization of the sample's features that are being characterized. Data processing based on the fine-grained impulse response can increase the contrast of the details of interest contained in the received data of the impulse response. This contrast increase, as described below, uses the fine-grained detail of the impulse response to narrow the analysis to the areas or regimes of interest in the sample. The improved fidelity provides greater precision of measurement, and, with appropriate calibration, greater accuracy. The greater accuracy, in turn, facilitates making finer distinctions between material components and/or their properties.

Making use of optimized choice of wavelengths of operation of the spectrometric device, as discussed above, improves the propagation of variance in the calculations that determine material properties Z (see 2110 in FIG. 21) based on the results of the amplitude measurements (see 2070 in FIG. 20B).

According to the idea of the invention, the analysis of data representing the measurement of a parameter characterizing the tissue (for example, a concentration of a particular species such as oxygenated hemoglobin, or glucose, or specific protein, or a physiological parameter such as aortic pressure) is performed in such a fashion as to dynamically and spatially localize a portion of the tissue to which such data pertains. Such spatial localization is achieved by analyzing portions of a curve that represents the parameter of interest and that is obtained by accounting of the impulse response of the tissue. Specifically, and in further reference to FIGS. 8C and 8D, while different portions of an impulse response curve of the tissue are associated with different paths that the EMW is taking from the transmitter through the tissue to reach the receiver, the impulse response curve integrated over the area of the tissue through which the EMW propagated is associated with the averaged over the tissue cross-section path length for the EMW (which is, of course, wavelength specific).

Figure 24A:
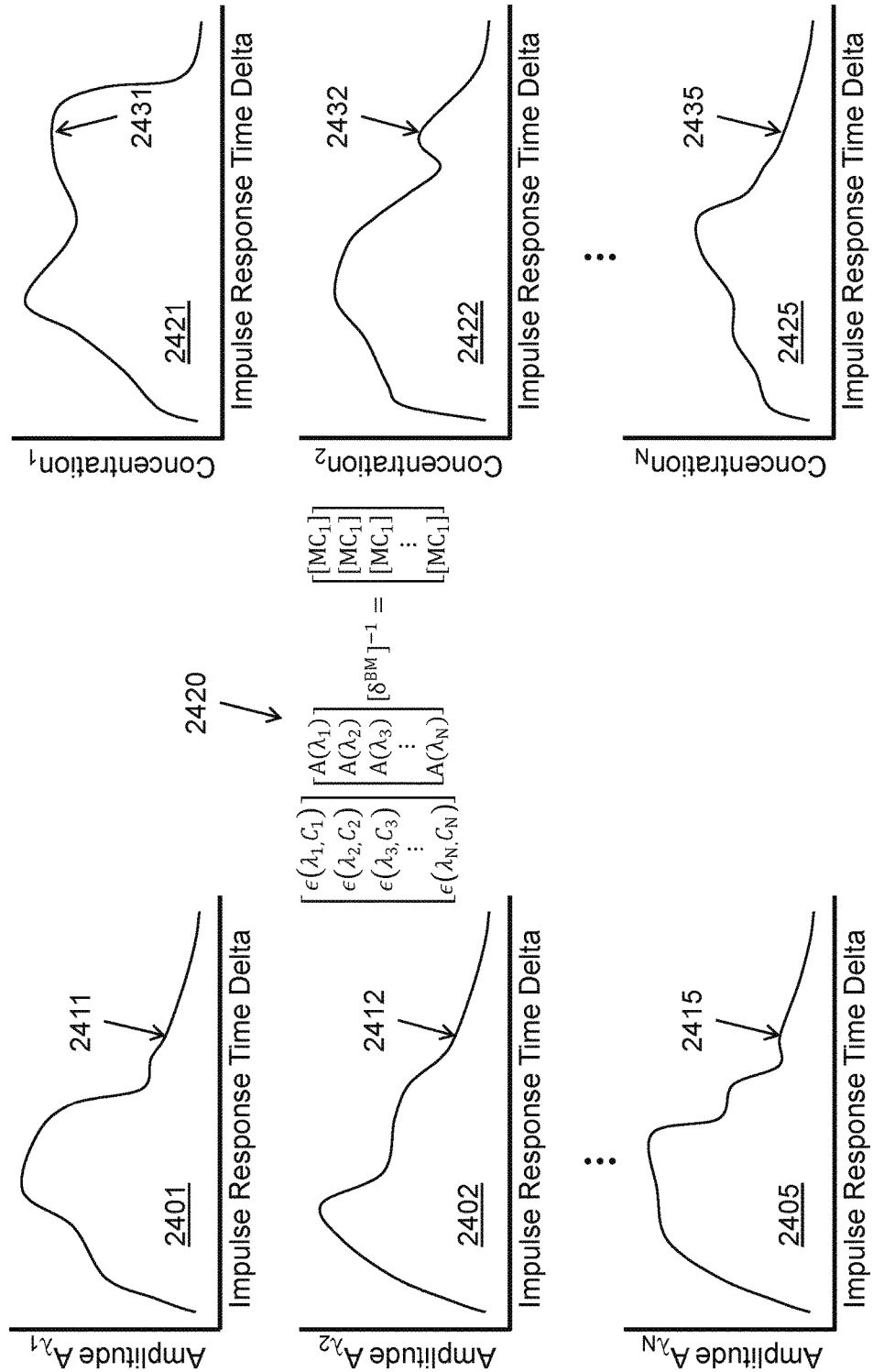
FIG. 24A is a diagram showing the elements used to calculate the impulse response of material properties of a sample from the measured received amplitude of transmitted excitation sequence trains of pulses from differing wavelengths and locations.

The tissue is excited by an impulse of the EMWs (at multiple wavelengths) by at least one transmitter and the impulse response of the tissue is measured, by at least one receiver, in terms of a chosen optical characteristic (e.g., absorption, scattering, optical anisotropy). Referring to Eq. (37c), such measurement produces the wavelength-dependent wavefront parameter denoted as $[A(\lambda_i)]$. Using the pre-determined characteristics such as the molar extinction coefficients $[\epsilon(\lambda_i, C_i)]$ and estimating the path-lengths $[\delta^{Ci}]$ of the EMWs through the tissue, the concentrations $[MC(\lambda_i)]$ of the species (material components) are then calculated based on the measured impulse response curves. FIG. 24A illustrates an example of the method of the invention. As shown, the use of the impulse response of the tissue sample (that is determined based on data representing attenuation of the signal transmitted through the sample) is made. The three graphs on the left (2401, 2402, and 2405) represent impulse response curves corresponding to time-dependent amplitudes of the signal as received at the detector and associated with a particular wavelength and/or location of a transmitter with respect to the sample. The amplitudes 2401, 2402, 2405 are associated with the respectively corresponding unique excitation sequence series of pulses used at the transmitter, and are recorded as a function of time lapsed after the moment of transmission of the corresponding signal. That is, the abscissa on each of the graphs represents the duration of time that a particular signal takes to propagate from the transmitter to the receiver. If the amplitude of the output generated by a correlator of the system is the result of a single pulse, then the single pulse must have enough energy to distribute over the time period and be measurable in a statistically repeatable manner. In an embodiment of the invention, many pulses are aggregated together by one of a variety of correlation circuits described above. However, other techniques could be used as long as the polarity of a pulse in a series transmitted pulses is normalized (in the examples above by multipliers, multiplexors, or exclusive-OR gates), and the time-delay corresponding to each pulse is normalized based on the transmission time to allow for correlation among different pulses from the series. This time-delay is directly related to the length of the path of propagation of a pulse and indirectly related to the transit speed. The value shown in the extinction curves of, for example, FIG. 3C, is in the units of (1/[concentration*distance]), meaning that to determine the concentration takes a distance factor (nominally the delta delay) and an attenuation, or received power/transmitted power. In further reference to curves 2401, 2402, and 2405, values of amplitude at a chosen "impulse-response delta time" for the respectively corresponding decoded excitation sequences $(\lambda i)$ 2411, 2412, and 2415 are used in a data processing step corresponding to the operation shown as 2420 (see Eq. 37C).

The output from the system of the invention at each time step is a series of values representing material component concentrations. These values, when aggregated together in a time-dependent fashion, are shown by the graphs 2421, 2422, and 2425 of FIG. 24A that represent, respectively, impulse responses for component concentration 1, component concentration 2, and component concentration N. The ellipses are used in FIG. 24A to indicate that the data collection and corresponding measurements are performed at multiple wavelengths in a similar fashion.

When referring to $\lambda i$ (with respect to data), the cohort referenced included both those correlated impulse responses that are differentiated by wavelength, and those correlated impulse responses that are differentiated by transmitter or receiver location. All of these various $\lambda i$'s are each extracted from the received signal by correlating them a time-controlled representation of the source excitation sequence of pulse.

A further improvement made possible by the fine-grained impulse response data is the potential to adjust the linear combination of the $\lambda i$'s impulse responses based on the diffusion-varied speed of propagation that is dependent on wavelength. This property of the sample material was discussed above in reference to the optimal selection of wavelengths of operation of the spectrometric device. If this information is available, then it can be used by modifying the process described in FIG. 24A by appropriately time-shifting the samples taken from the impulse response based on wavelength—for each particular analyte—when creating the instantaneous material property of the impulse response.

Figure 24B:
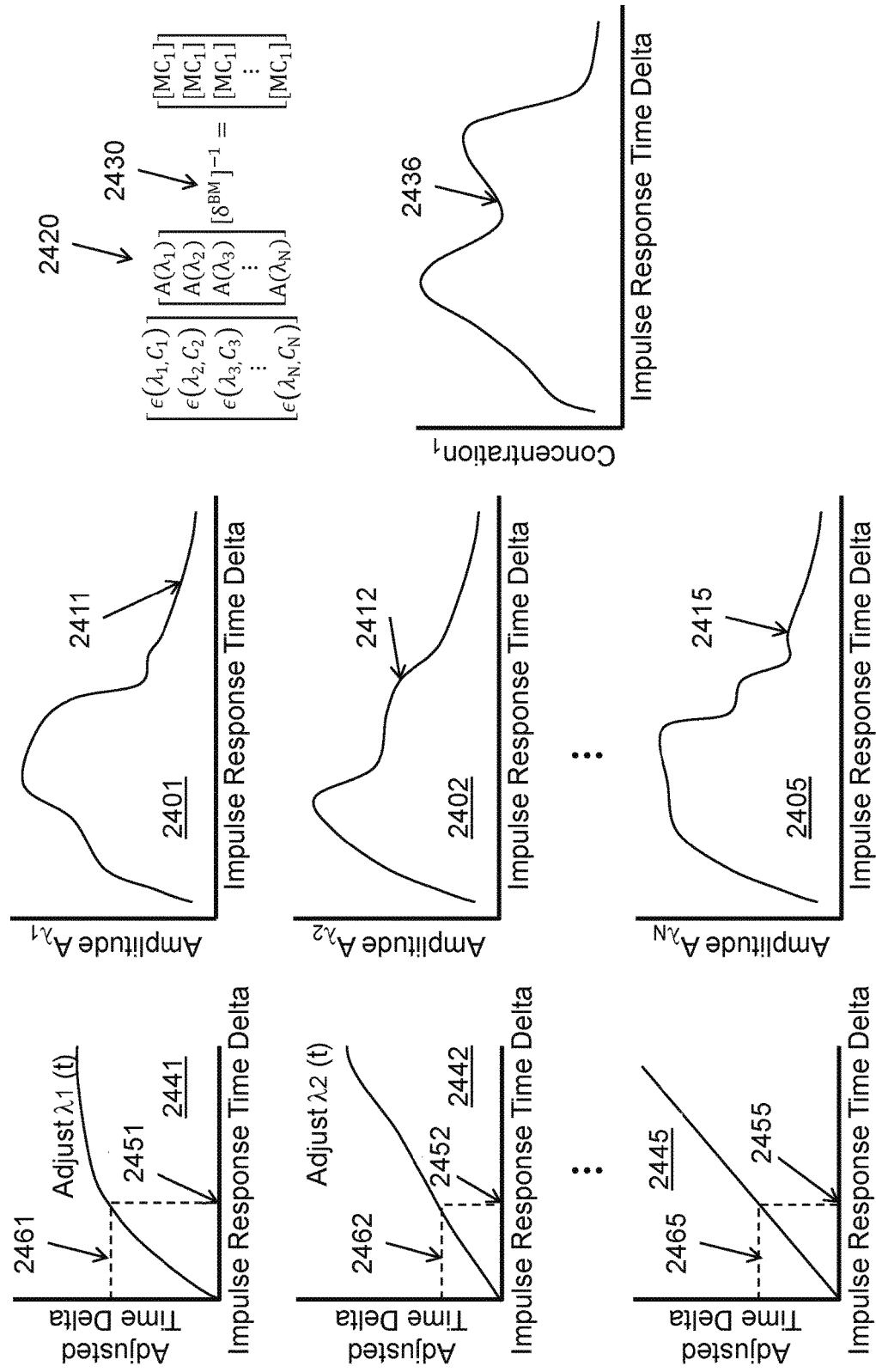
FIG. 24B is a diagram illustrating one method of the invention for introducing material component, path length, and wavelength based adjustments to the calculations of the impulse response material properties of a sample from the measured received amplitude of transmitted excitation sequence trains of pulses from differing wavelengths and locations.

For example, and referring to FIG. 24B, graph 2441 represents the time shift appropriate for wavelength $\lambda_1$ specific to material component 1. The desired time-parameter 2436, representing the "impulse response time delta" in the concentration of material component 1 output, is used as index 2451 on graph 2441, to produce an adjusted time delta 2461. The adjusted time delta is used to index 2411 on graph 2401 to provide input to the matrix calculation 2420.

In a similar manner, graphs 2442 . . . 2445 represent the time shift appropriate for wavelengths $\lambda\_2$ . . . $\lambda\_N$ specific to the material component 1. The desired concentration output impulse response time delta 2436 is used as indices 2452 . . . 2455 on graphs 2442 . . . 2445, to produce the adjusted time deltas 2462 . . . 2465. These adjusted time deltas are used to index 2412 . . . 2415 on graphs 2402 . . . 2405 to provide inputs to the matrix calculation 2420.

Although this has been illustrated as a simple time shift, it will be appreciated that the input could also be a function of the wavelength impulse response, taking into account more points, and providing for the possibility of weighted summation, interpolations, and other similar methods of choosing the input to the matrix operation 2420. Additionally it is noted that the term $[\delta^{BM}]^{-1}$, labeled as 2430 in FIG. 24B, is used to account for the path length of each particular data sample. As discussed above, this may be a scaling for the increased extinction experienced by the path; it may as well be augmented by gained knowledge of the heterogeneous makeup of the sample. This knowledge may be gained, for example, from the sampled-measurement of the sample with the use of the micro-mirror array described above, from results of external/independent analysis using the micro-mirrors in combination to provide feedback, optimizing signal transmitted or received by modifying level, frequency of chips, and excitation sequence characteristics, providing a larger field of view, increasing the effective density of transmitters and receivers, and techniques described above. All information is contained in the signal from a single transmitter and receiver with or without a mirror or mirrors in place. Additional useful information is gained by increasing the number of transmitters and receivers or by increasing their effective density as can be done with the micro-mirror array described earlier.

The Use of Embodiment(s) for Determination of Beat-To-Beat Cardiac Stroke Volume and Cardiac Output The magnitude of cardiac output in cardiac-compromised patients (e.g., those with damaged heart valves, or those who has a heart attack or coronary artery disease, or who have been heavy smokers, etc.) is a critical measure of health and illness. The units of cardiac output are "liters per minute" of blood pumped by the heart. At a finer granularity, cardiac output is composed of the individual amounts of blood pumped during each heartbeat, referred to as "beat-to-beat stroke volume," where the "stroke" is one heartbeat or contraction of the heart's left ventricle. In the early days, before the onset of hospital-based ultrasound systems, there was no reliable way of measuring beat-to-beat stroke volume; an X-ray based technique could measure stroke volume, but only a few medical centers had the capability, and a cardiac catheterization laboratory and staff were required (performing a highly skilled procedure). Modern ultrasound systems can estimate beat-to-beat stroke volume if used by a highly trained ultrasonographer. Although this is a costly test, the cost is less than the cost of a cardiac catheterization laboratory.

In *Continuous Determination of Beat-to-Beat Stroke Volume From Aortic Pressure Pulses in the Dog*, Circulation Research, 39(1):15-24, July 1976, Bourgeois, M. J., B. K. Gilbert, G. von Bernuth, and E. H. Wood proposed a method for calculating a beat-to-beat stroke volume (and hence cardiac output) based on the beat-to-beat pulse pressure wave in the central thoracic aorta. The proposed method raised at least two questions. First, according to the method, the aortic pressure pulse wave had to be measured with a catheter inserted through a femoral artery and advanced into the aorta. Such a procedure requires the availability of specialized hospital environment. Second, to be of clinical value, the calculations had to be carried out on a beat-by-beat basis, in "real time," which was beyond even the mainframe computers at the time of the research reported in the manuscript. Accordingly, the proposed method was never implemented in general clinical practice.

Non-trivial extensions to the work of Bourgeouis et al. that make use of the oximetry aspects of the system herein described can be used to provide accurate non-invasive measurement of the beat-to-beat stroke volume of a measurement subject. The described spectrometer provides measurement of the near-instantaneous changes in blood component concentration between the transmitter and receiver of the sensors; the waveform of this information is used as a "surrogate" waveform for the aortic pressure pulse contour. The quality of this surrogate waveform is further improved where a subset of the material component concentration curve is selected from the spacing and depth region of the sample, which provides a maximum variation or the oxygen bearing components, rather than the variation of the oxygen-depleted components. This selection of the source for the saturation waveform provides for measurement of the arterial rather than venous variation. Choosing a source corresponding to an artery (not a vein) close to the skin surface provides a better surrogate for the aortic pressure pulse: the arterial pressure pulse is a "damped" version of the aortic behavior, since the peripheral artery is fed from the aorta. Using this local resolution capability and the selection criteria, the system computes beat-to-beat cardiac stroke volume, and hence cardiac output, in real time, in the patient's free-living environment. The resulting information provides benefit to cardiologists treating patients whose cardiac function is compromised. Further, the use of multiple sites of interrogation (i.e., multiple photo detectors) time-locked together, with or without the previously described excitation sequence encoding, would allow the detection of variations in blood flow and cardiac output associated with cardiovascular state, e.g. hypovolemia detection. Any changes in the values of these variables then may be predictive of deterioration or instability of cardiovascular state.

What is provided by the present invention is the ability to identify and/or localize the ideal measurement site, to measure instantaneous changes in oxygen saturation and to create a surrogate aortic pressure pulse waveform, and thus calculate cardiac stroke volume and cardiac output.

Properties that are beneficially measured using the optimized selection of wavelength, the introduction of challenges to the sample, and the use of selected possibly relatively orthogonal selected transmitter excitation sequences include, but are not limited to the various hemoglobin analyte concentrations and time based variation described, as well as blood glucose level, blood protein level, blood lipid level, total body water, central blood volume, concentration of fluorescent biomolecules or dyes, respiratory tidal volume, beat-to-beat cardiac stroke volume, and beat-to-beat cardiac stroke volume variation.

Based on the multiple relatively orthogonal coding sequences described elsewhere, the sensor output can be processed simultaneously by multiple correlators to produce the measurement value for each input wavelength. Being able to run these measurements simultaneously can advantageously eliminate motion-based inaccuracies when comparing multiple wavelengths.

Challenge Based Measurements

Material properties of interest, characterizing the tissue, include physiological parameters some of which (for example, central blood volume or total amount of water in the tissue) cannot be measured directly. Diagnostic techniques, developed to measure such physiological parameters indirectly are based on the dilution of "tracers" introduced into the blood and tissue. For example, tracers are injected into an artery or vein, administered orally, or inhaled (in a form of, for example, small quantities of a gas such as carbon monoxide), and the blood sample is subsequently analyzed to quantify the percent of the tracer therein. The tracers are selected to facilitate their detection through various in vitro (laboratory) or in vivo (in the humans) means, but in this context, spectrometrically. Some tracers that have been used include carbon monoxide, and fluorescent dyes, several of which are available from commercial sources and have been or are being tested for safe clinical application in patients. Depending on the tracer used, and the accuracy of measurements, various physiological variables can be measured.

Other material properties of interest are associated with various physiological analytes or metabolites. A subset of these metabolites are those chemical derivatives that are formed in vivo through normal biochemical processes in response to the administered drug (as described above) that has been metabolized (i.e., broken down or degraded through in vivo biochemical processes). A chemical substance is a material component with uniform properties. Given the uniform properties, a chemical substance may be analyzed spectrometrically to determine its unique spectral signature. Using techniques described elsewhere in this application, specific EM wavelength(s) are chosen to best identify the metabolite that is associated with the drug of interest. In this manner, the metabolite is used as a "tracer".

Figure 22:
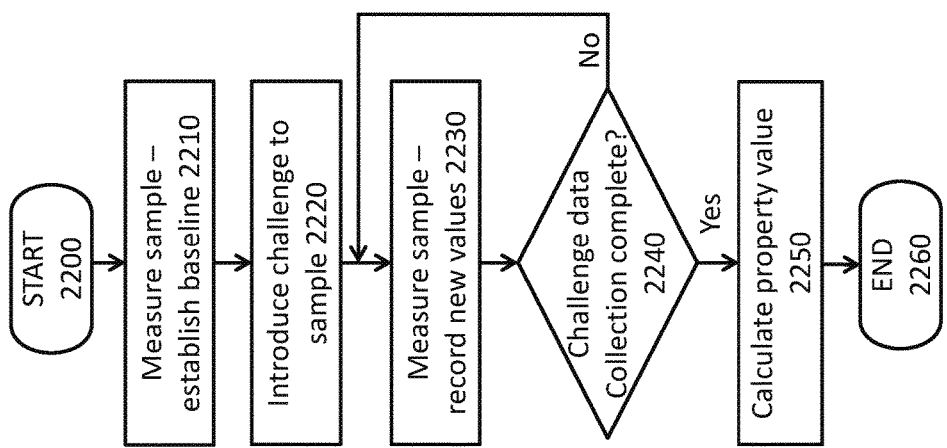
FIG. 22 is a flowchart showing the process for using a challenge to measure a property of a material component.

For the purposes of this disclosure, the term "challenge" is used to represent a substance introduced into a material (e.g., blood) to later be measured as a proxy for a parameter associated with the material (e.g., blood volume or drug uptake). Examples of challenges include but are not limited to trace gases and drugs. Some drugs could be detected directly and/or through their associated metabolite(s). Given a challenge, the process used in analysis of the material parameter is illustrated in the flowchart of FIG. 22. The process starts at steps 2200 and 2210, with a baseline measurement of the sample. Once the baseline of a sample characteristic is established, the challenge is introduced (e.g., through injection, inhalation, or oral introduction) at step 2220 and the so-modified sample is then measured to acquire representative data at step 2230. This process of data collection continues until sufficient (as measured by an externally defined rule) data are gathered, at step 2240, to allow for the calculation of the property value of interest at step 2250. At this point the process is completed (END 2260).

The techniques used to-date to quantify the properties, of a material component of a sample, that are caused by a challenge, have varying degrees of accuracy, invasiveness, and, at times, undesired side effects. What is required in clinical applications is a means to measure such quantities with sufficient accuracy for clinical requirements, non-invasively, and with minimal side effects to the patient. The techniques for selection of optimal EM wavelengths, transmitting the waveform(s), receiving the waveform(s) after interacting with the sample, and quantifying the result that have been described elsewhere in this application are as applicable to the challenge-based process as they are to the detection of other properties.

As an instance of the challenge-based property measurement technique that is improved in substantial and non-obvious ways, the measurement of total blood volume can be augmented with the additional accuracy provided by the invention to change the use case. Support of measurement of the change in blood volume over time would be of significant benefit in the triage of care. Carbon monoxide (CO) is used as a detectable tracer for the measurement of total blood volume, because it binds preferentially over oxygen to hemoglobin.

Figure 23:
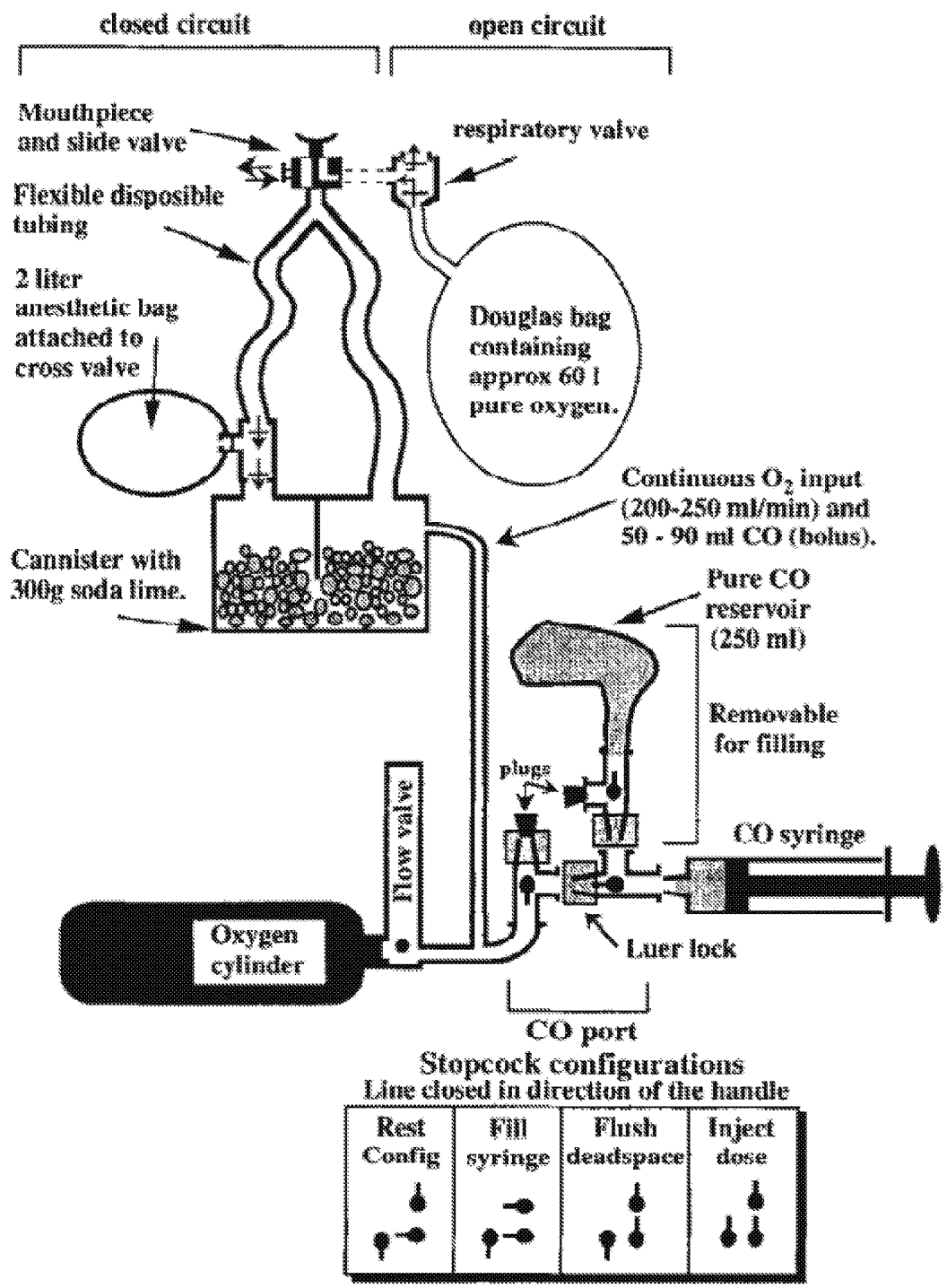
FIG. 23 is a diagram illustrating a common high quality technique for introducing a measured amount of carbon monoxide to a human subject.

Burge and Skinner, in "Determination of hemoglobin mass and blood volume with CO: evaluation and application of a method," *Journal of Applied Physiology*, vol. 79, pp. 623-631, Aug. 1, 1995, described measuring total blood volume by introducing a measured aliquot of CO to a subject, with carboxyhemoglobin concentration measures before and 10 minutes after the administration of the aliquot. Their method used the apparatus illustrated in their report, and illustrated here in FIG. 23. In C. J. Gore, W. G. Hopkins, and C. M. Burge, "Errors of measurement for blood volume parameters: a meta-analysis," *Journal of Applied Physiology*, vol. 99, pp. 1745-1758, Nov. 1, 2005, the effectiveness of the technique compared to other techniques was demonstrated with a meta-analysis of several studies. The accuracy of the technique is in the range of 0.8%, but achieving such accuracy requires the introduction of CO in the amount sufficient to raise the percentage of hemoglobin bound to CO by (or on the order of) 6.5 percentage points. As the dangerous limit of CO concentration in blood is $\leq 15\%$, and the half-life time of CO in blood varies from 50 minutes with pure oxygen to 2-8 hours in normal subjects, it is understood that the use of multiple detectable aliquots is not possible within a short time period using the current technology. According to Gore 2005, the two reasons behind using such a large aliquot are, first, delivering a smaller amount may be subject to delivery quantity error, and second, that current external reading blood gas monitors provide precision only to 0.1%.

With the increased precision offered by the methods and systems of the present invention, a much smaller aliquot can be used to provide usable and reliable results. Using aliquots low enough such that regular administration of CO aliquots is safe over a period of time provides, for example, an effective monitor for central blood volume without compromising the health of the subject Given the rate of rapid rate of dispersion of CO through the system, it would be possible to present additional aliquots as often as every 10 minutes, provided the incremental detection is sufficiently sensitive.

Fluorescence

Local anesthesia is, in many cases, a superior means of pain control in avoiding the side effects of narcotic pain medication. Nerve blocks are commonly used for postoperative pain control as well as the primary anesthetic when the avoidance of general anesthesia is desired. The use of local anesthesia in this application renders an area insensitive to pain without affecting consciousness, speeding the detection of complications and patient recovery. However, when performing a nerve block, relatively large drug doses can be required to inhibit the nerve conduction to the surgical site. By way of example, the required injection volumes are often in the range of 20-40 cc. Unfortunately, as little as 1 cc of local anesthesia injected into an artery can cause seizure, and large intravascular local anesthesia injection will block the conduction system of the heart, possibly leading to cardiac arrest and death. Symptoms evidencing the onset of toxic anesthesia contamination include numbness of the tongue, lightheadedness and visual and auditory disturbances, and can occur at concentrations below 7.5 mcg/ml. Approximately 5 in 10,000 surgeries report severe complications caused by intravascular local anesthesia, but thousands of regional blocks are done every day.

There are very few tools available to anesthesiologists to protect patients from this problem. One known method involves an epinephrine marked 'test dose' of local anesthesia. During injection, doctors watch for an increase in heart rate or blood pressure indicating an inadvertent intravascular injection. Unfortunately, this method is very unreliable. Patients taking beta-blockers or wearing a pacemaker may be unresponsive to epinephrine. Children often have blocks done under general anesthesia that alters the body's response to adrenaline and makes it difficult to determine if the local anesthesia is intravascular. An epinephrine marker during an epidural can cause complications by decreasing blood flow to the fetus in pregnant women. There remains, therefore, a continuing need for improved systems and methods for providing accurate and early warning of intravascular local anesthesia.

One embodiment of the invention is a method for operating a spectrometer to monitor a patient receiving local anesthetic marked with dye that absorbs infrared light. This method includes: (1) applying light pulses to a patient that is receiving (or has received) anesthetic marked with fluorescing dye; (2) detecting the light emitted by the patient and providing an output representative of the light detected; (3) processing the output to derive information representative of the presence of dye-marked anesthetic; and (4) displaying the information representative of the presence of the dye-marked anesthetic as a function of the information representative of the fluorescence.

Figure 28:
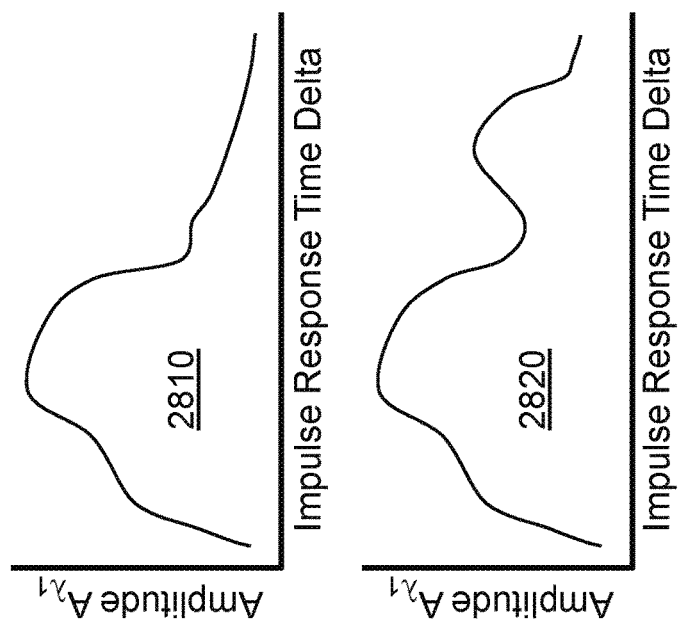
FIG. 28 is a set of graphs showing an example impulse response without the presence of a fluorescing dye and with the presence of a fluorescing dye in the measurement sample.

It is appreciated that results of applying such method that has been enhanced by using the mechanisms described above in producing the impulse response are advantageous. Due to the delaying nature of the fluorescing activity, the impulse response curve for any of the wavelengths that trigger the fluorescence will have extended tails. FIG. 28 illustrates the impulse response of the tissue without the fluorescent dye (curve 2810) and with the presence of the fluorescent dye (curve 2820). The use of the method for operating a spectrometer that utilizes the impulse response approach is advantageous over a peak or bulk correlation in that it increases the sensitivity of the measurement.

Localization

Referring to FIG. 1C, an improved measurement of a cardiac stroke volume can be enabled based on an embodiment of the invention. FIG. 1A shows an embodiment with the sensor 160 juxtaposed to the finger. This is often referred to as a peripheral measurement and is appropriate for many uses. However, when considering a measurement of the cardiac activity, the measurement of the pulse wave at the finger is strongly affected by the impedance of the circulatory system. The waveform of the pulse wave (when measured at location 140) closely resembles, in shape, the curve 2530 of FIG. 25 discussed below, with potentially undetermined noise additionally present in the heart-centric measurements. Therefore, it is advantageous to ensure alternate placement of the spectrometric device onto the body. FIG. 1B shows the sensor placed closer to the heart, as compared with FIG. 1A.

FIG. 1C includes a sketched side view of the human head, neck, shoulders, and a portion of the arterial circulation system 190. The neck 193, just at the shoulder joint, provides proximity to at least one major artery, the carotid artery 191. A sensor 145 in this illustration is an instance configured to monitor closely the concentration characteristics due to the blood flow in the carotid artery 191. When elements of an implementation of the invention are taken together (including at least the transmitter(s) 110, and the receiver(s) 130, 131, and 132) the spectrometric system is referred to, collectively, as the sensor 145.

Figure 25:
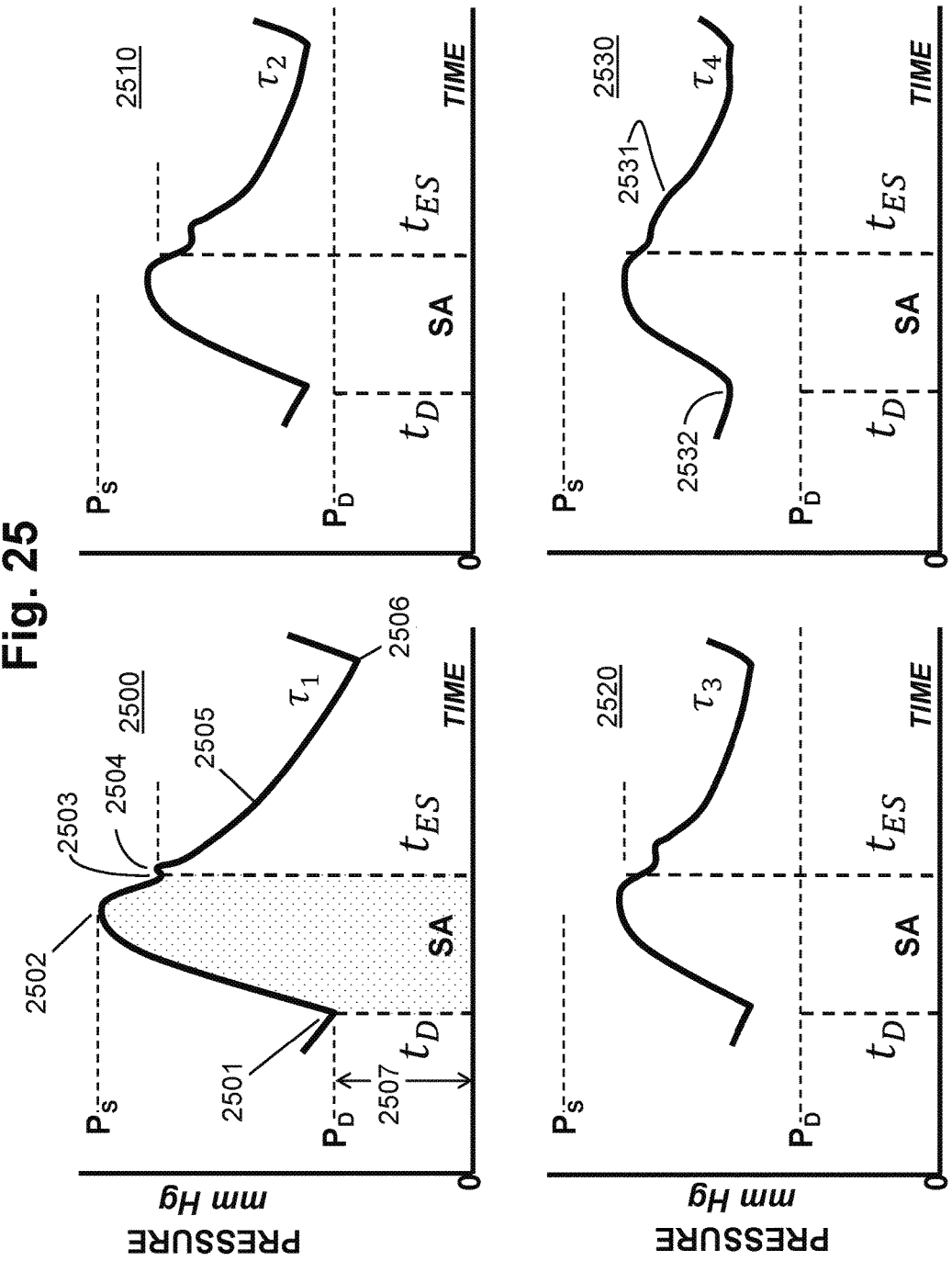
FIG. 25 is a set of graphs illustrating example pressure profiles from different measurement locations responsive to heart beat variation.

Referring to FIG. 25, the graphs 2500, 2510, 2520, and 2530 illustrate variation of blood pressure in a blood vessel over time. Systole is the portion of the complete cardiac cycle when the left ventricle is ejecting blood into the ascending aorta through the aortic valve. Diastole is that portion of the cardiac cycle when the ventricle is being refilled by the left atrium, the aortic valve is closed, no blood is flowing into the aorta from the left ventricle; however, during diastole, blood continues to flow from the aorta into the arterial vasculature and then into the arterioles and capillaries deep in the body tissues. During the systole, blood is also flowing into the peripheral arteries as noted above; but the primary effect is the partial refilling of the aorta by the left ventricle.

Referring to graph 2500, the point at (time=$t_D$, pressure=$P_D$) represents the minimum pressure at the end of diastole 2501, just as the systolic ejection phase begins, as measure at a location point specified with respect to the heart. The systole continues, achieving a peak pressure $P_S$ at 2502. As the left ventricular contraction ends and the aortic valve closes, the aortic pressure begins to decrease to a local minimum at 2503, followed by a slight pressure increase at 2504 (referred to as the incisura or dichrotic notch). The dichrotic notch is caused by a pulse wave reflection traversing the ascending aorta, the aortic arch, and the descending thoracic aorta as the aortic valve closes. At the time following the appearance of the dichrotic notch at 2505 in FIG. 25, the aortic valve is completely closed, and the aortic pressure decreases as blood drains out of the aortic, which functions as an elastic reservoir to maintain as much pressure in the arterial tree as possible. It has been shown (in *Continuous Determination of Beat-to-Beat Stroke Volume From Aortic Pressure Pulses in the Dog, Circulation Research,* 39(1): 15-24, July 1976, Bourgeois, M. J., B. K. Gilbert, G. von Bernuth, and E. H. Wood) that the phase 2505 can be characterized by an exponential decay with time constant $\tau$. This time constant, which can be determined during the diastolic portion of each cardiac cycle, is used in the calculation of beat volume. The beat illustrated ends at 2506 with the beginning of the next cardiac systole as the aortic valve reopens.

As the pressure wave is measured at additional points across the body that are located progressively farther from the heart than the point at which the pressure wave graph 2500 has been measured, the corresponding time-dependent pulse waves (shown as 2510, 2520, and 2530) weaken due to impedance of the circulatory system. The peaks of the corresponding pulse-waves are generally reduced, the steady-state pressure increases, and the exponential decay portions of the curves are also affected. In graph 2530 (acquired from the measurement taken at a point that is the farthest from the heart among those discussed), for example, reflections of the pulse wave can be seen as 2531, and a smoothed delay at the beginning of the systole can be seen as 2532. It is understood that these graphs represent decay and broadening of a pulse wave corresponding to a healthy and unobstructed circulatory system, and are used to illustrate the operational advantages of placement of the sensor as close to the central aorta as feasible.

Figure 26:
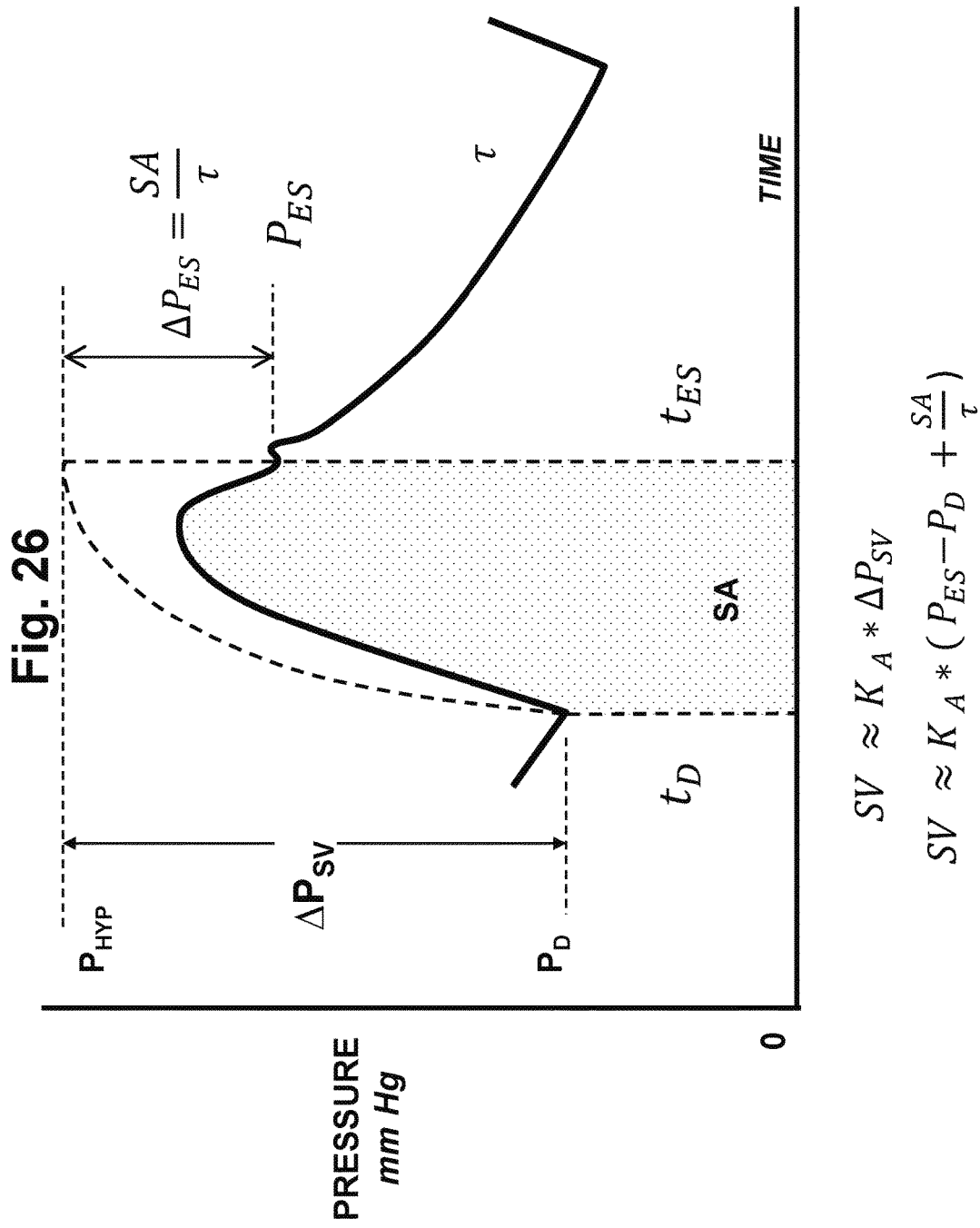
FIG. 26 is a graph illustrating the basis of a method for determining stroke volume and blood flow volume.

Bourgeois et al. proposed a method for calculating a beat-to-beat stroke volume (and hence the cardiac output) from measurements of and subsequent calculations based on the beat-to-beat pulse pressure wave in the central aorta. The chart of FIG. 26 (corresponding to FIG. 1 of Bourgeouis et al.) illustrates the "method for determination of individual beat-to-beat stroke volume from aortic pressure pulses". The solid curve represents a normal pressure pulse from the central thoracic aorta. The dashed curve above the systolic portion of the pressure pulse represents the hypothetical aortic pressure contour, resulting in a pressure increment, $\Delta P_{ES}$, which would occur if all peripheral vessels were to be closed during systole, thereby preventing systolic drainage. The pressure equivalent to the diastolic drainage in the steady state case is ($P_{ES}-P_D$). The pressure equivalent to the total stroke volume, $\Delta P_{SV}$, is the sum of these values. $K_A$ is a proportionality factor." (quoted from the Bourgeouis et al.)

To calculate the stroke volume (SV), the following operations are performed:

$$SV = K_A \Delta P_{SV} \qquad (50)$$

$$SV = K_A [(P_{ES} - P_D) + \Delta P_{ES}] \qquad (51)$$

$$SV = K_A \left[(P_{ES} - P_D) + \frac{SA}{\tau}\right] \qquad (52)$$

As discussed earlier, the time constant $\tau$ can be calculated after measurements are obtained. The other constant, $K_A$, requires a calibration phase followed by the desired measurements if absolute readings of cardiac stroke volume are required, or can remain as a constant if only relative changes in stroke volume over time are desired. The pressure values are then obtained from the measurement.

Regarding $K_A$, Bourgeois 1976 used only a single calibration "based on the first indicator-dilution measurement of cardiac output performed at the beginning of an experiment" for a set of experiments. This "was used for all subsequent determinations of stroke volume." The results of the measurements demonstrated "the relative invariability of the $K_A$ value" over the durations and under the conditions of the experiment. The invariability "is implied by the numerical similarity of the standard deviations calculated from the entire set of data measured during short experiments as well as from those of extended duration." Therefore, a single $K_A$ derivation prior to measurement is adequate to produce sufficient accuracy for many applications requiring absolute readings of cardiac stroke volume.

Additionally, as the arterial pulse is propagating, at higher pressure the arterial cross section increases slightly (depending on the elasticity of the aortic wall and the strength of the ventricular contraction). The increase of the arterial cross section facilitates, in turn, the transmission of the EMW that traverses the sample, through the characteristic oxyhemoglobin. Because the impulse response is measured with such fine grain (see FIG. 8E), an attendant increase in attenuation overall will be measured that corresponds to the vessel expansion. As a result, there will be an increase in the width of that portion of the impulse response that is caused by the material component that contributes a larger percentage to the optical path (between the optical source and the detector) during systole than that during diastole. In the present example, such material components if blood. Accordingly, both the peak concentration of the impulse response and the area under the curve of the impulse response will increase. The increase of the aorta in width is, of course, dependent on the elasticity of the arterial walls; such elasticity is estimated from the rate of rise between the points 2501 and 2502 of the graph 2500 of FIG. 25. Accentuating the contribution from the portions of the step function that vary with changes in effective optical path length throughout the cardiac cycle improves the measurement as a surrogate for pressure.

Accordingly, the oximetry system of the invention enables the identification of the optimal site or location for measurement of instantaneous changes in oxygen saturation and creation of a surrogate aortic pressure pulse waveform, based on which the calculation of the cardiac stroke volume and cardiac output is carried out. Similarly, other pulse waveforms may be measured throughout the body.

Measurements are not restricted to the aforementioned physiological variables. Other physiological variables can be measured using similar techniques. With the increased sampling frequencies, the transit time and therefore also the velocity of blood may be estimated in real-time.

Figure 8E:
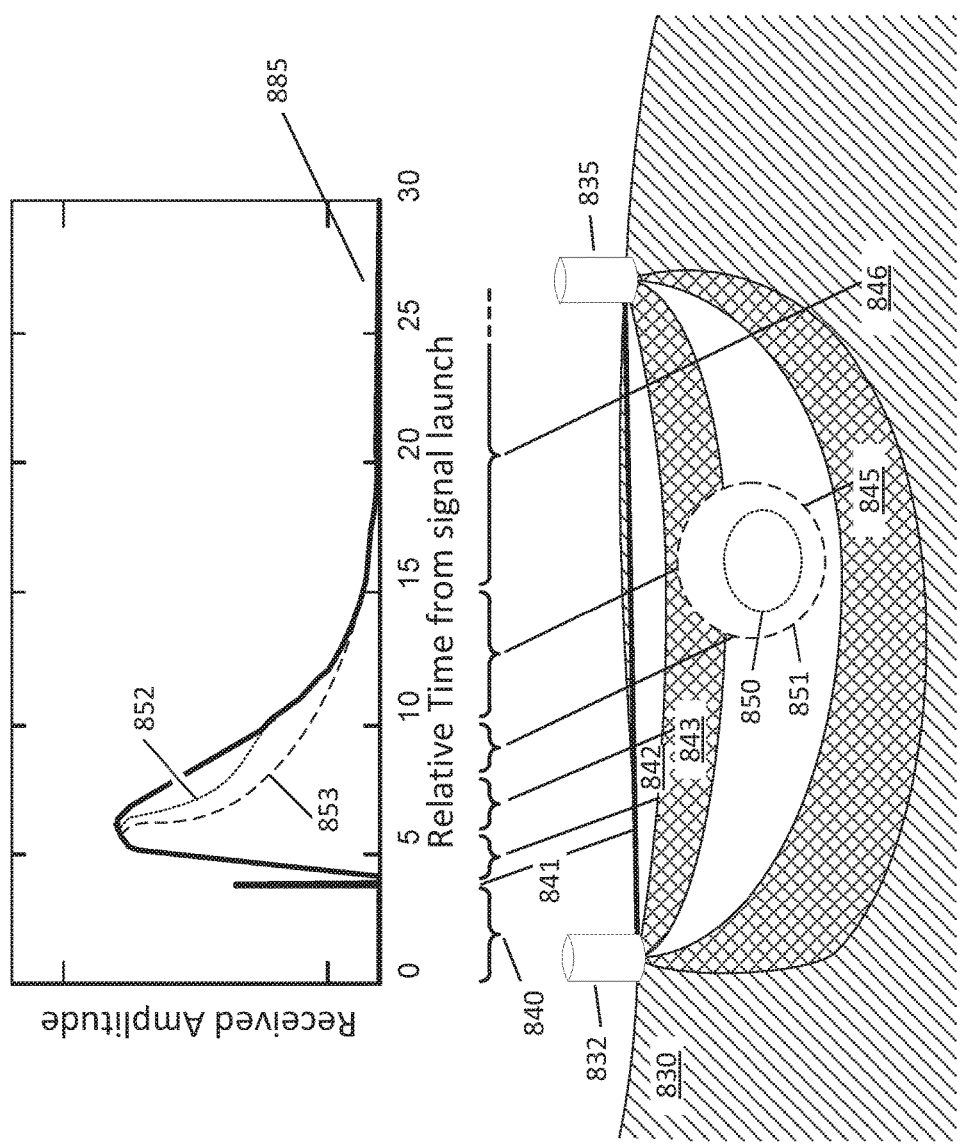
FIG. 8E is a modification of the diagram of FIG. 8D relating changes in the impulse response graph from FIG. 8C to the changing diameter of a heterogeneous object in the example cross section.

The shape of individual returned signals (see FIG. 8D) can be used to measure additional information regarding the central aortic vessels, e.g., their elasticity. This analysis of the shape and change of shape of blood vessels is illustrated in FIG. 8E that shows a blood vessel both constricted, 850, and dilated, 851. The constricted vessel 850 is outlined with a fine dashed line and the dilated vessel 851 is outlined with a course dashed line. The time-dependent amplitude of the signal returned by the constricted vessel 850 is shown in the graph as line 852 and for the dilated vessel 851 as line 853. The primary observation from this figure is that the size of the vessel influences both the width of the curve representing the detected signal and the area under the curve. From this graph it can be seen that the determination of the change of size a blood-vessel and its elasticity is enabled, according to an embodiment of the invention, by measurement of the shape of the waveform of the impulse response of the blood-vessel.

As was alluded to before, and according to one embodiment of the invention, the fundamental instrumentation block includes a "transceiver pair" formed by a transmitter and a single detector. The impulse response is derived for such a transceiver pair. At minimum, when the transmitter operates at a single wavelength, the derivation of this impulse response enables the estimation of the average, wavelength-specific path length light travels through the tissue. (This corresponds to the centroid of the true impulse response, i.e. calibration.) In addition, the fundamental optical properties of the tissue can be extracted including the scattering, absorption, and anisotropy of the tissue. These data represent data collected at a point in time at a single wavelength. Once additional data is collected, in a similar fashion, as a function of time, the changes of the physiological or optical parameter of the tissue with time can be determined (e.g., a change of the pulse pressure wave, see for example FIG. 26). One additional result is the ability to characterize changes in the underlying tissue as a function of time and physiology (see for example, FIG. 8E). According to an embodiment of the invention, the parameter characterizing the tissue is spatially localized when such parameter, determined based on the measured impulse response of the tissue, is coarsely spatially mapped to the tissue with the use of predetermined or tabulated frequency dependent attenuation characteristics (see FIG. 8D).

Extending the measurement further by employing multiple wavelengths of light, determining the spectrally-dependent impulse response of the tissue, and determination of the spectral dependence of the parameter characterizing the tissue enables, for example, the estimation of concentration of as many species as there are wavelengths in the EMW propagating between the transmitter and the receiver of the pair, at one point in time. Extending the determination of the spectral dependence of the tissue parameter by carrying out multiple measurements separated in time, enables spatial localization of the parameter. (see FIG. 8D)

The next logical extension of the method providing for spatial localization of the tissue parameter is the use of a single transmitter and multiple receivers, spaced from the transmitter in different ways. For each new transceiver pair all previous steps occur. The localization of the tissue parameter determined based on multiple overlapping or spatially shifted impulse responses results in increased density of sampling in FIG. 8D, and enables the formation of an image of the underlying tissue that references specific anatomical structures of interest. Yet the next fundamental extension of the method is the derivation of spatial distribution of the tissue parameter(s) based on impulse responses determined at multiple transceiver pairs at multiple wavelengths of operation and multiple separations, enabling a comprehensive spatially dense map of tissue parameters estimated through time and space.

Referring again to FIGS. 8D and 24 A, it is appreciated that different portions of a given material characteristic curve (such as curve representing concentration of a material component or a physiological parameter derived, in accordance with the embodiments of the invention, based on the measured or determined impulse response curve) are associated with spatially-different portions of the tissue through which the EMWs propagated from the transmitter to the receiver. Put differently, the spatial location of a region of the tissue is coded in both the measured impulse response curve and the material parameter curve calculated based on such impulse response curve. By analyzing different portions of the calculated material parameter curve, such parameter can be spatially mapped across the tissue (and, therefore, localized to a given portion of the tissue). In this case, the conclusion about the value of the sought-after parameter characterizing the tissue is made on a dynamically localized spatial basis. For example, by considering the front portions of the concentration curves 2421, 2422, through 2425 of FIG. 24A, the concentrations of respectively corresponding material species are defined in the regions of tissue that has delayed the EMW by the least amount, while the tail portions of the curves 2421, 2422 through 2425 contain information of the corresponding concentration values related to the portions of the tissue that have delayed the EMW the most. The integrated over time impulse response curve and the corresponding integrated concentration curve would be associated with a spatially-averaged-over-the-tissue concentration of the given material parameter.

Figure 27:
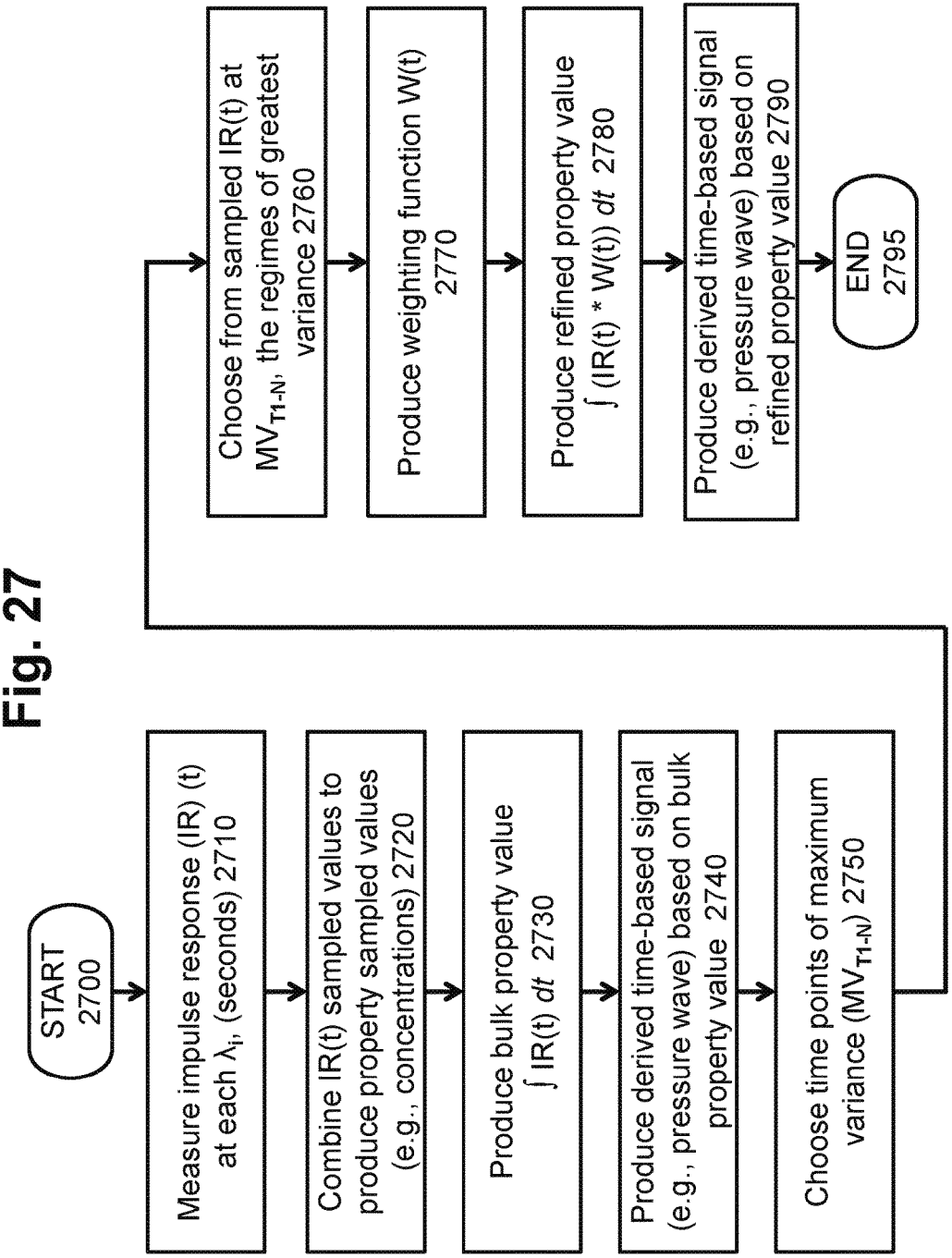
FIG. 27 is a flow diagram illustrating the steps of a technique for improving the sensitivity of measurement of time changing material properties in a heterogeneous structure.

In reference to FIG. 27, an embodiment of the invention directed to the measurements of the sample that are spatially localized to the region of the sample that with the use of the impulse responses is initiated at step 2700; the impulse response (IR) (t) is measured for each of multiple wavelengths $\lambda i$ and at each time point of interest for generating a time-derived sequence, at step 2710. An example of a time-derived signal would be deriving the contour of a pressure wave surrogate from a sequence of samples $[S_{T1}, \ldots, S_{TN}]$ with each $S_T$ is conceptually composed of the integral $\int IR_{T_x}(t)dt$ of a particular measurement $IR_{T_x}(t)$ of the impulse response based at time Tx. (The resulting time-derived sequence would nominally resemble the form represented by the graph 2500 of FIG. 25).

The next step is to combine the impulse response (t) with the sampled $\lambda_i$ values to determine impulse response values (t) representing a property of the material component of interest.

From so-determined impulse response (t) sampled values, a value representing the bulk property is formed, at step 2730, by summing the values of the individual samples 2720. Then, the derived time-based sequence is formed at 2740. This sequence, corresponding to, for example, a pressure wave surrogate, is based on the bulk, not localized, averaged over the tissue cross-section property value 2730. The result may be similar to, for example, the graph 2500 of FIG. 25. Using that graph representation as an illustration, the process would proceed to identify time points of interest ($MVT_{1-N}$) at step 2750. In this case, if the details of the local maximum of the measured curve are of interest, the data values corresponding to the points on the curve 2500 of FIG. 25 and labeled as 2501, 2502, 2503, 2504, and 2506 are likely the points of interest that could be identified as inflection points of the time-derived property value. If, on the other hand, achieving precision in time is the goal, then the local cohort of data surrounding these points of interest can be chosen.

Once the specific points in time are chosen, analysis of the data can be conducted to determine the impulse response delay time values that exhibit the highest variance, or stated alternately, those that provide the greatest contrast between the areas of the derived time-based property of interest 2760. This can also be described as choosing, at step 2760, the regimes of larger cross variance from the sampled impulse responses at $MVT_{1-N}$. From so obtained information, produce a weighting function W(t) over the impulse response time range at step 2770. Using the weighting function together with the impulse response (t) values, a refined property value can be determined as $\int IR(t)*W(t) dt$, at step 2780. Finally, a refined derived time-based signal (such as the refined pressure wave) can be determined based on the refined property value, at step 2790. This completes the process of producing the weighting function.

The weighting function, once determined, can be reused for subsequent measurements. Many events will cause a need to recalculate the weighting function, including, but not limited to motion of the sample.

Implementations of the invention can employ a processor controlled by instructions stored in a tangible memory to perform the steps of operation of the system described above. The memory may be random access memory (RAM), read-only memory (ROM), flash memory or any other memory, or combination thereof, suitable for storing control software or other instructions and data. In an alternative embodiment, the disclosed system and method may be implemented as a computer program product for use with a computer system. Such implementation includes a series of computer instructions fixed either on a tangible non-transitory medium, such as a computer readable medium (for example, a diskette, CD-ROM, ROM, or fixed disk) or transmittable to a computer system, via an interface device (such as a communications adapter connected to a network over a medium). Some of the functions performed during the execution of the method of the invention have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. In addition, while the invention may be embodied in software such as program code, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention has been described through the above-presented examples of embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

What is claimed is:

1. A method for measurement of a beat-to-beat cardiac stroke volume variation of a living body with a spectrometric system that includes at least one transmitter and at least one receiver, the method comprising:
   disposing the at least one transmitter on a surface of a region-of-interest (ROI) of the body, the ROI including a peripheral artery, and placing the at least one receiver on the body;
   performing an oximetry measurement to acquire, with a data-processing circuitry of the spectrometric system, a time-dependent output from the at least one receiver caused by the at least one transmitter's emission of at least one electromagnetic wave (EMW) at at least one corresponding wavelength,
   wherein the time-dependent output represents time-dependent changes of a concentration of oxygen in arterial blood of the peripheral artery, of the ROI, determined along a path from the at least one transmitter to the at least one receiver, said path defined by a gradient of the concentration of oxygen in said arterial blood;

from the time-dependent output, creating a waveform that is a surrogate for a pulse pressure in an aorta; and from changes in the waveform, identified as a function of time, determining the beat-to-beat cardiac stroke volume variation.

2. The method according to claim 1, wherein the determining the beat-to-beat cardiac stroke volume variation includes determining the beat-to-beat cardiac stroke volume based on the surrogate for the pulse pressure in the aorta, said surrogate representing a pulse of changes in the concentration of oxygen in the arterial blood.

3. The method according to claim 1, further comprising changing at least one of locations of the at least one transmitter and the at least one receiver to spatially localize said disposing and said placing by determining impulse responses of the ROI for at least one transceiver pair at multiple wavelengths, the impulse responses being associated with emission of the at least one EMW by the at least one transmitter, the transceiver pair being a pair formed by the at least one transmitter and the at least one receiver.

4. The method according to claim 3, wherein the determining an impulse response, from the impulse responses, includes determining the impulse response of the ROI based on a time-dependent characteristic of the at least one transceiver pair, wherein the at least one pair is identified at the data-processing circuitry of the system by a respectively corresponding excitation sequence series of pulses produced by the at least one transmitter, a first excitation sequence series of pulses at a first wavelength being orthogonal to a second excitation sequence series of pulses at a second wavelength.

5. The method according to claim 1, wherein the performing the oximetry measurement comprises acquiring an output representing an optical property that includes at least one of wavelength-dependent scattering, absorption, and anisotropy of said arterial blood.

6. The method according to claim 1, wherein the determining the beat-to-beat cardiac stroke volume includes determining changes of the concentration of oxygen along a path that is different from a path assumed by the use of Beer-Lambert's law.

7. The method according to claim 1, further comprising determining a change of a size of the peripheral artery as a function of time during at least a systolic portion of an arterial pulse based on said concentration of oxygen.

8. The method according to claim 1, further comprising:
sampling a curve representing the time-dependent output as a function of time to obtain values of the concentration of oxygen at sampled points in time, and forming a weighting function by calculating variance values among the values of the concentration of oxygen at the sampled points in time, the weighting function being defined by said variance values as a function of time.

9. The method according to claim 8, further comprising:
modifying a wavelength-dependent material parameter characterizing the sample based on (i) the computed impulse response that has been weighted by the weighting function and (ii) the reference data.

10. The method according to claim 1, further comprising:
at different wavelengths, modulating respectively-corresponding EMWs emitted by the at least one transmitter with first and second excitation sequences produced at the at least one transmitter, the first and second excitation sequences being orthogonal to one another.

11. The method according to claim 1, further comprising forming a spatial map of the determined concentration of oxygen across a cross-section of the ROI located between the at least one transmitter and the at least one receiver based on different portions of a curve representing said output as a function of time.

12. The method according to claim 1, further comprising adding a chemical substance to the living body, and wherein said performing includes determining a change in at least one wavelength-dependent material parameter caused by said adding.

13. The method according to claim 1, further comprising generating emission of said at least one transmitter as electromagnetic pulses in a defined excitation sequence and transmitting said pulses through a delay line with multiple delay taps to enhance a determination of a change in the concentration and to reduce a cost of the determining of the beat-to-beat cardiac stroke volume variation.

14. The method according to claim 1, further comprising enhancing localization of the determining the beat-to-beat cardiac stroke volume variation based on:

repositioning at least one transceiver pair along a surface of the ROI to a plurality of positions;

determining an impulse response of the ROI corresponding to each of the plurality of positions of the at least one transceiver pair to form a plurality of impulse responses and expressing the impulse responses from the plurality of impulse responses as impulse response curves; and identifying a position, of the at least one transceiver pair, at which a respectively-corresponding impulse response curve exhibits the highest variance among variances of the plurality of impulse response curves, wherein the at least one transceiver pair is a pair formed by the at least one transmitter and the at least one receiver.

15. The method according to claim 1, further comprising:
determining a change of a length of an effective passage of light from the at least one transmitter to the at least one receiver through the peripheral artery as a function of time during at least a systolic portion of an arterial pulse based on said concentration of oxygen.

* * * * *

UNITED STATES PATENT AND TRADEMARK OFFICE
CERTIFICATE OF CORRECTION

PATENT NO. : 10,260,947 B2
APPLICATION NO. : 16/056214
DATED : April 16, 2019
INVENTOR(S) : Clifton R. Haider et al.

It is certified that error appears in the above-identified patent and that said Letters Patent is hereby corrected as shown below:

In the Specification

Column 63, Line 67, "(t)" should be --(t) $\lambda_i$--.

Signed and Sealed this
Tenth Day of September, 2019

Andrei Iancu
*Director of the United States Patent and Trademark Office*